US008372809B2

(12) United States Patent
Unemori et al.

(10) Patent No.: US 8,372,809 B2
(45) Date of Patent: *Feb. 12, 2013

(54) METHOD OF TREATING DYSPNEA ASSOCIATED WITH ACUTE HEART FAILURE

(75) Inventors: Elaine Unemori, Oakland, CA (US); Sam L Teichman, Alamo, CA (US); Gad Cotter, Chapel Hill, NC (US); Dennis R Stewart, Los Gatos, CA (US); Martha J Whitehouse, San Mateo, CA (US)

(73) Assignee: Corthera, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/242,012

(22) Filed: Sep. 23, 2011

(65) Prior Publication Data

US 2012/0040902 A1    Feb. 16, 2012

Related U.S. Application Data

(63) Continuation of application No. 12/467,214, filed on May 15, 2009, now Pat. No. 8,053,411.

(60) Provisional application No. 61/164,333, filed on Mar. 27, 2009, provisional application No. 61/201,240, filed on Dec. 8, 2008, provisional application No. 61/190,545, filed on Aug. 28, 2008, provisional application No. 61/127,889, filed on May 16, 2008.

(51) Int. Cl.
 *A61K 38/22* (2006.01)
 *C07K 14/64* (2006.01)
 *A61P 9/00* (2006.01)
 *A61P 9/10* (2006.01)
 *A61P 11/00* (2006.01)

(52) U.S. Cl. .................. 514/12.7; 514/12.1; 514/16.4; 530/300

(58) Field of Classification Search .................. None
See application file for complete search history.

(56) References Cited

U.S. PATENT DOCUMENTS

| | | | |
|---|---|---|---|
| 5,023,321 A | 6/1991 | Hudson et al. | |
| 5,166,191 A | 11/1992 | Cronin et al. | |
| 5,478,807 A | 12/1995 | Cronin et al. | |
| 5,759,807 A | 6/1998 | Breece et al. | |
| 5,811,395 A | 9/1998 | Schwabe et al. | |
| 5,952,296 A | 9/1999 | Bigazzi | |
| 6,211,147 B1 | 4/2001 | Unemori | |
| 6,723,702 B2 | 4/2004 | Conrad et al. | |
| 6,780,836 B2 | 8/2004 | Unemori | |
| 2004/0192606 A1 | 9/2004 | Unemori | |
| 2004/0266685 A1 | 12/2004 | Conrad et al. | |
| 2005/0113286 A1 | 5/2005 | Schreiner et al. | |
| 2005/0238639 A1 | 10/2005 | Conrad et al. | |
| 2006/0264367 A1 | 11/2006 | Samuel et al. | |
| 2007/0202080 A1 | 8/2007 | Yun et al. | |
| 2008/0077025 A1 | 3/2008 | Delgado-Herrera et al. | |

FOREIGN PATENT DOCUMENTS

| | | |
|---|---|---|
| WO | WO-02/40500 A2 | 3/1993 |
| WO | WO-93/03755 A2 | 3/1993 |
| WO | WO-2009/007848 A2 | 1/2009 |
| WO | WO-2009/140657 A2 | 11/2009 |

OTHER PUBLICATIONS

Adams et al. (Am Heart J 149: 209-216, 2005).*
Albert et al., "Evidence-Based Practice for Acute Decompensated Heart Failure", Critical Care Nurse, 24(6): 14-29 (2004).
Allen and O'Connor, "Management of Acute Decompensated Heart Failure", CMAJ, 176(6):797-805 (2007).
Balion et al, "Physiological Pathological, Pharmacological, Biochemical and Hematological Factors Affecting BNP and NP-proBNP", Clinical Biochemistry, 41:231-239 (2006).
Bani et al, "Relaxin Counteracts Asthma-Like Reaction Induced by Inhaled Antigen in Sensitized Guinea Pigs", Endocrinology, 138:1909-1915 (1997).
Bani, "Relaxin: A Pleiotropic Hormone", General Pharmacology, 28(1):13-22 (1997).
Bathgate et al, "Receptors for Relaxin Family Peptides", Ann NY Acad Sci, 1041:61-76 (2005).
Belziti et al, "Worsening Renal Function in Patients Admitted with Acute Decompensated Heart Failure Incidence, Risk Factors and Prognostic Implications", Reference Rev. Esp. Cardiol, 63(3):294-302 (2010).
Bullesbach et al, "Total Synthesis of Human Relaxin and Human Relaxin Derivative by Solid-Phase Peptide Systhesis and Site-Directed Chain Combination", The Journal of Biological Chemistry, 266(17):10754-10761 (1991).
Chen et al, "Pharmacological Characterization of Relaxin-3/INSL7 Receptors GPCR135 and GPCR142 from Different Mammalian Species", The Journal of Pharmacology and Experimental Therapeutics 312(1):83-95 (2005).
Conrad and Novak, "Emerging Role of Relaxin in Renal and Cardiovascular Function", Am. J. Physiol. Integr. Comp. Physiol., 287:R250-R261 (2004).
Conrad et al, "Relaxin Modifies Systemic Arterial Resistance and Compliance in Conscious Nonpregnant Rats", Endocrinology, 145:3289-3296 (2004).
Cotter et al. "The Pathophysiology of Acute Heart Failure—It it All About Fluid Accumlation?", American Heart Journal, 155(1):9-18 (2008).
Debrah et al. "Effects of Relaxin on Systemic Arterial Hemodynamics and Mechanical Properties in Conscious Rats: Sex Dependency and Dos Response", J. Appl. Physiol., 98:1013-1020 (2005).
Debrah et al, "Relaxin Increases Cardiac Output and Reduces Systemic Arterial Load in Hypertensive Rates", Hypertension, 46:745-750 (2005).

(Continued)

*Primary Examiner* — Bridget E Bunner
*Assistant Examiner* — Fozia Hamud
(74) *Attorney, Agent, or Firm* — Lisa Matovcik

(57) ABSTRACT

The disclosure pertains to methods of reducing decompensation through acute intervention including in subjects afflicted with acute decompensated heart failure. Particularly, the disclosure provides methods for treating acute cardiac decompensation by administering a pharmaceutically effective amount of relaxin.

16 Claims, 23 Drawing Sheets

OTHER PUBLICATIONS

Debrah et al, "Relaxing is Essential for Systemic Vasodilation and Increased Global Arterial Compliance During Early Pregnancy in Conscious Rats", Endocrinology, 147:5126-5131 (2006).
Dschietzig et al, "The Pregnancy Hormone Relaxin is a Player in Human Heart Failure", FASEB Journal, 15:2187-2195 (2001).
Dschietzig et al, "Relaxin: A Pregnancy Hormone as Central Player of Body Fluid and Circulation Homeostasis", Cellular and Molecular Life Sciences, 80(4):688-700 (2003).
Dschietzig et al, "A Pilot Safety and Dose-Finding Trial of Intravenous Recombinant Human Relaxin (rhRix) in Compensated Congestive Heart Failure", Eur. Heart J. 28(abstract supplement) 387 (2007).
Dschietzig et al, "Intravenous Recombinant Human Relaxin in Compensated Heart Failure: A Safety, Tolerability, and Pharmacodynamic Trial", J. Cardiac Fail., 15:182-190 (2009).
Dschietzig et al, "First Clinical Experience with Intravenous Recombinant Human Relaxin in Compensated Heart Failure", Ann. NY Acad. Sci., 1160(1):387-392; 2009.
Edouard et al, "Venous and Arterial Behavior During Normal Pregnancy", Am. J. Physiol. Heart Circ. Physiol., 274:H1605-H1612 (1998).
Fisher et al, "N-Terminal pro B Type Natriuretic Peptide, but not the New Putative Cardiac Hormone Relaxin, Predicts Prognosis in Patients with Chronic Heart Failure", Heart. 89:879-881 (2003).
Francis et al, "Acute Decompensate Heart Failure: The Cardiorenal Syndrome", Cleveland Clinic Journal of Medicine, 73(2):1-13 (2006).
Garibay-Tupas et al, "Regulation of the Human Relaxin Genes H1 and H2 by Steroid Hormones", Molecular and Cellular Endocrinology, 219:115-125 (2004).
Gheorghiade and Filippatos, "Reassessing Treatment of Acute Heart Failure Syndromes", Eur. Heart J. Supplements, 7(Suppl.B):B13-B19 (2005).
Gheorghiade and Zannad, "Modern Management of Acute Heart Failure Syndromes. Eur. Heart J. Supplements", 7(Suppl.B):B3-B7 (2005).
Gheorghiade et al, "Systolic Blood Pressure ad Admission, Clinical Characteristics, and Outcomes in Patients Hospitalized with Acute Heart Failure", JAMA, 296:2217-2226 (2006).
Hernandez and Granger, "Advancing Care of Acute Heart Failure— No Time to Relax", Lancet, 373:1401-1402 (Epub. Mar. 28, 2009).
Hershberger et al, "Care Processes and Clinical Outcomes of Continuous Outpatient Support with Inotropes (COSI) in Patients with Refractory Endstage Heart Failure"Journal of Cardiac Failure, 9(3):180-187 (2003).
Heywood, "The Cardiorenal Syndrom: Lessons from the ADHERE Database and Treatment Options", Heart Fail. Rev., 9:195-201 (2004).
Hunt et al. "ACC/AHA 2005 Guidelines Update for the Diagnosis and Management of Chronic Heart Failure in the Adult: A Report of the American College of Cardiology/American Heart Association Task Force on Practice Guidelines", Circulation, 112(12):e154-235 (2005).
Jessup et al, "2009 Focused Update: ACCF/AHA Guidelines for the Diagnosis and Management of Haert Failure in Adults: A Report of the American College of Cardiology Foundation/American Heart Association Task Force on Practice Guidelines", Circulation, 119(4):1977-2016 (2009).
Jeyabalan et al, "Essential Role for Vascular Gelatinase Activity in Relaxin-Induced Renal Vasodilation, Hyperfiltration, and Reduced Myogenic Reactivity of Small Arteries", Circulation Research, 93:1249-1257 (2003).
Jeyabalan et al. "Renal Function During Normal Pregnancy and Preeclampsia", Frontiers in Bioscience, 12:2425-2437 (Jan. 1, 2007).
Khanna et al, "Recombinant Human Relaxin in the Treatment of Systemic Sclerosis with Diffuse Cutaneous Involvement", Arthritis & Rheumatism, 60:1102-1111 (2009).
Koelling et al, "The Expanding National Burden of Heart Failure in the United States: The Influence of Heart Failure in Women", American Heart Journal, 147:74-78 (2004).
Kremastinos, "Acute Heart Failure: An Old Syndrome Revisited", Hellenic J. Cardiol., 49:199-200 (2008).
Krumholz et al, "Predictors of Readmission Among Elderly Survivors of Admission with Heart Failure", American Heart Journal, 139(1):72-77 (2000).
Kupari et al, "Is the Pregnancy Hormone Relaxin an Important Player in Human Heart Failure?", Eur. J. Heart Fail., 7:196-198 (2005).
Levey et al, "A More Accurate Method to Estimate Glomerular Filtration Rate from Serum Creatine: A New Prediction Equation", Annals of Internal Medicine, 130:451-470 (1999).
McAlister et al, Renal Insufficiency and Heart Failure, Prognostic and Therapeutic Implications from a Prospective Cohort Study, Circulation, 109:1004-1009 (2004).
McBride et al, "Acute Decompensated Heart Failure: A Contemporary Approach to Pharmacotherapeutic Management", Pharmacotherapy, 23(8):997-1020 (2003).
Metra et al. "Vasodilators in the Treatment of Acute Heart Failure: What We Know, What We Don't", Heart Fail. Rev., 14:299-307 (Epub. Dec. 19, 2008).
Moore et al, "Determination of Left Ventricular Function by Emergency Physician Echocardiography of Hypotensive Patients", Academic Emergency Medicine, 9(13):186-193 (2002).
Nieminen et al, "Executive Summary of the Guidelines on the Diagnosis and Treatment of Acute Heart Failure", Eur. Heart J., 26:384-416 (2005).
Nistri et al, "Relaxin as a Cardiovascular Hormone: Physiology, Pathophysiology and Therapeutic Promises", Cardiovascular Hematology Agents in Medicinal Chemistry, 5:101-108 (2007).
Novak et al, "Relaxin is Essential for Renal Vasodilation During Prenancy in Conscious Rats", J. Clin. Invest., 107:1469-1475 (2001).
O'Neill et al, "Recent Advances in the Diagnosis of Heart Failure", Current Cardiology Reports, 6(3):205-210 (2004).
Pang et al, "A Proposal to Standardize Dyspnoea Measurement in Clinical Trials of Acute Heart Failure Syndroms: The Need for a Uniform Approach", European Heart Journal, 29:816-824 (2008).
Rose et al, "Long-Term Use of a Left Ventricular Assist Device for End-Stage Heart Failure, The New England Journal of Medicine", 345(20):1435-1443 (Nov. 15, 2001).
Rozanski et al, "Development and Application of Normal Limits for Left Ventricular Ejection Fraction and Volume Measurements from 99mTc-Sestamibi Myocardial Perfusion Gated SPECT", The Journal of Nuclear Medicine. 41(9):1445-1450 (2000).
Samuel et al, "Physiological or Pathological: A Role for Relaxin in the Cardiovascular System?", Curr. Opin. Pharmacol., 3:152-158 (2003).
Satpathy et al, "Disgnosis and Management of Disatolic Dysfunction and Heart Failure", American Family Physician, 73:841-846 (2006).
Schrier et al, "Hormones and Hemodynamics in Heart Failure", NEJM, 341(8):577-585 (1999).
Seibold et al, "Recombinant Human Relaxin in the Treatment of Scieroderma: A Randomized, Double-Blind, Placebo-Controlled Trial", Annals of Internal Medicine. 132(11):871-879 (2000).
Sharma et al, "A Rational Approach for the Treatment of Acute Heart Failure: Current Strategies and Future Options", Curr. Opin. Cardiol., 19:254-263 (2004).
Shemesh et al, "Discovery and Validation of Novel Peptide Agonist for G-Protein-Coupled Receptors", J. Biol. Chem., 283:34643-34649 (Epub. Oct. 9, 2008).
Sherwood, "Relaxin's Physiological Roles and Other Diverse Actions", Endocrine Reviews, 25(2):205-234 (2004).
Shin et al, "Review of Current and Investigational Pharmacologic Agents for Acute Heart Failure Syndromes", American Journal of Cardiology, 99[suppl] 4A-23A (2007).
Slangen et al, "Hemodynamic Changes in Early Pregnancy in Chronically Instruments, Conscious Rats", American Journal of Physiology, 270(5):H1779-H1784 (1996).
Smith et al, "Influence on Recombinant Human Relaxin on Renal Hemodynamics in Healthy Volunteers", Journal of the American Society of Nephrology, 17:3192-3197 (2006).
St. Louis and Massocotte, "Chronic Decrease of Blood Pressure by Rat Relaxin in Spontaneously Hypertensive Rats", Life Sciences, 37:1351-1357 (1985).
Stewart et al, "More 'Malignant' Than Cancer? Five-Year Survival Following a First Admission for Heart Failure", European Journal of Heart Failure, 3(3):315-322 (2001).

Sudo et al, "H3 is a Specific Ligand for LGR7 and Activates the Receptor by Interacting with Both the Ectodomain and the Exoloop 2", J. Biol. Chem., 278(10):7855-7862 (2003).

Tang et al., "Novel Strategies fosr the Management of Acute Decompensated Heart Failure", Current Cardiology Reviews, 1(1):1-5 (2005).

Teerlink et al, "Relaxin for the Treatment of Patients with Acute Head Failure (Pre-RELAX-AHF): A Multicentre, Randomised, Placebo-Controlled, Parallel-Group, Dose-Finding Phase llb Study", The Lancet, 373:1429-1439 (2009).

Teichman, et al, "Relaxin, a Pleiotropic Vasocilator for the Treatment of Heart Faiture", Heart Fail. Rev., located at http://wpringerlink.com/content/586ki33348m11334/fulltext.html, 20 pages, last visited on Jan. 12, 2009.

Van Der Westhuizen, "Responses of GPCR135 to Human Gene 3(H3) Relaxin in CHO-K1 Cells Determined by Microphysiometry", Ann. NY Acad. Sci., 1041:332-337 (2005).

Ward et al, "Relaxin Increases Rat Heart Rate by a Direct Action on the Cardiac Atrium", Biochemical and Biophysical Research Communications, 186:999-1005 (1992).

Wewers et al, "A Critical Review of Visual Analogue Scales in the Measurement of Clinical Phenomena", Research in Nursing and Health, 13:227-236 (1990).

Wilkinson et al, "Evolution of the Relaxin-Like Peptide Family", BMC Evolutionary Biology, 5(14):1-17 (2005).

ADHERE Scientific Advisory Committee, Acute Decompensated Hearth Failure National Registry (ADHERE) Core Module Q1 2006, Scios, Inc., 53 pages (2006).

"Corthera Closes $23 Million Financing Round", Corthera, Inc. Press Release, 2 pages (Dec. 20, 2007).

"Corthera Initiates Phase II Clinical Trial of Relaxin in Acute Heart Failure", Corthera, Inc., Press Release, 1 page (Jan. 8, 2008).

"Corthera's Relaxin Receives FDA Fast Track Designation for the Treatment of Acute Heart Failure", Corthera, Inc., Press Release, 1 page (Oct. 1, 2009).

"Interim Analysis of Top-Line Data From Phase II/III Study Shows Favorable Efficacy & Safety for Corthera's Relaxin in Acute Heart Failure", Cortheria, Inc., Press Release, 1 page (Nov. 10, 2008).

"Novartis to Acquire Corthera Inc., Gaining Worldwide Rights to Phase III Project Relaxin for Treatment of Acute Decompensated Heart Failure", Corthera, Inc., Press Release, 3 pages (Dec. 23, 2009).

"Results and Additional Analyses from Efficacy and Safety Study of Corthera's Relaxin in Acute Hearth Faiture to be Presented at Heart Failure Congress 2009", Corthera, Inc., Press Release, 1 page (May 28, 2008).

"Results From Efficacy and Safety Study of Corthera's Relaxin in Acute Hearth Failure to be Presented at Late-Breaking Clinical Trials Session at ACC 58th Annual Scientific Session", Corthera, Inc., Press Release, 1 page (Mar. 23, 2008).

"Results from Study Show Promising Efficacy and Safety Results for Corthera's Relaxin in Acute Heart Failure", Corthera, Inc., Press Release, 2 pages (Mar. 29, 2008).

"Top-Line Preliminary Data From Phase II/III Study of Corthera's Relaxin in Acute Heart Failure to be Presented in Satellite Symposium at AHA Scientific Sessions 2008", Corthera, Inc., Press Release, 1 page (Nov. 3, 2008).

Heart Failure Society of America, Pocket Guide: HFSA Comprehensive Hart Failure Practice Guideline, HFSA, St Paul, MN, 1-95 (2006).

"MedlinePlus Medical Encyclopedia: Breathing Difficulty", Retrieved on Apr. 23, 2010 at: http://www.nlm.nih.gov/medlineplus/ency/article/003075.htm (Feb. 27, 2008).

NCT00259116, "A Pilot Study of Recombinant Human Relaxin (rhRix) in Compensated Congestive Heart Failure". BAS Medical Clinical Trial Announcement (2005).

NCT00406575, "Recombinant Human Relaxin for the Treatment of Decompensated CHF", BAS Medical Clinical Trial Announcement (2006).

NCT00520806, "Efficacy and Safety of Relaxin for the Treatment of Acute Heart Failure (RELAX-AHF)", BAS Medicial Clinical Trial Announcement (2007).

New Zealand Office Action for New Zealand Patent Application 243970 (Novartis Case No. 54140-NZ-PCT (Jun. 24, 1997).

UK Office Action mailed Jun. 30, 2009 for UK Patent Application 0908432.8, filed May 18, 2009.

UK Office Action mailed Nov. 30, 2009 for UK Patent Application GB0918132.2, filed May 18, 2009.

UK Office Action mailed Sep. 30, 2009 for UK Patent Application GB0908432.8, filed May 19, 2009.

International Search Report and Written Opinion received for PCT Patent Application PCT/US2009/044249, mailed Jun. 4, 2010.

International Search Report received for PCT Patent Application PCT/US2009/044247, mailed Oct. 5, 2009.

J. Malcolm O. Arnold, MD, The Merck Manual for Health Care Professionals Cardiovascular Disorders, Heart Failure (HF) Symptons and Signs, Part 74 (Table 74-l), English language; cited in corresponding JP Patent Application No. 2011-509783 as translated into Japanese, Last full revision Jan. 2010.

Jeyabalan et al., "The Vascular Actions of Relaxin", Chapter 6, Landes Bioscience and Springer Science and Business Media, 2007.

* cited by examiner

Relaxin Causes Vasodilation in the Presence of Vasoconstriction

```
                        SEQUENCE LISTING

<160> NUMBER OF SEQ ID NOS: 8

<210> SEQ ID NO 1
<211> LENGTH: 29
<212> TYPE: PRT
<213> ORGANISM: Homo sapiens

<400> SEQUENCE: 1

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 2
<211> LENGTH: 24
<212> TYPE: PRT
<213> ORGANISM: Homo sapiens
<220> FEATURE:
<221> NAME/KEY: VARIANT
<222> LOCATION: (1)...(24)
<223> OTHER INFORMATION: Xaa = Glu or Gln

<400> SEQUENCE: 2

Xaa Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 3
<211> LENGTH: 8
<212> TYPE: PRT
<213> ORGANISM: Artificial Sequence
<220> FEATURE:
<223> OTHER INFORMATION: Relaxin consensus sequence
<221> NAME/KEY: VARIANT
<222> LOCATION: (1)...(8)
<223> OTHER INFORMATION: Xaa = Any Amino Acid

<400> SEQUENCE: 3

Arg Glu Leu Val Arg Xaa Xaa Ile
1               5

<210> SEQ ID NO 4
<211> LENGTH: 33
<212> TYPE: PRT
<213> ORGANISM: Artificial Sequence
<220> FEATURE:
<223> OTHER INFORMATION: Synthesized Construct
<221> NAME/KEY: VARIANT
<222> LOCATION: 1
<223> OTHER INFORMATION: Xaa = Absent or Gly or a small naturally or
      non-naturally occurring amino acid
<221> NAME/KEY: VARIANT
<222> LOCATION: 2
<223> OTHER INFORMATION: Xaa = Absent or Gln or a polar naturally or
      non-naturally occurring amino acid
<221> NAME/KEY: VARIANT
<222> LOCATION: 3
```

-continued

```
<223> OTHER INFORMATION: Xaa = Absent or Lys or a basic naturally or
      non-naturally occurring amino acid
<221> NAME/KEY: VARIANT
<222> LOCATION: 4
<223> OTHER INFORMATION: Xaa = Absent or Gly or a small naturally or
      non-naturally occurring amino acid
<221> NAME/KEY: VARIANT
<222> LOCATION: 5
<223> OTHER INFORMATION: Xaa = Absent or Gln or Ser or a polar naturally
      or non-naturally occurring amino acid
<221> NAME/KEY: VARIANT
<222> LOCATION: 6
<223> OTHER INFORMATION: Xaa = Absent or Val or Ala or Pro or Met or
      a hydrophobic naturally or non-naturally occurring amino acid
<221> NAME/KEY: VARIANT
<222> LOCATION: 7
<223> OTHER INFORMATION: Xaa = Absent or Gly or a small naturally or
      non-naturally occurring amino acid
<221> NAME/KEY: VARIANT
<222> LOCATION: 8
<223> OTHER INFORMATION: Xaa = Absent or Pro or Leu or Ala or a
      naturally or non-naturally occurring amino acid
<221> NAME/KEY: VARIANT
<222> LOCATION: 9
<223> OTHER INFORMATION: Xaa = Absent or Pro or Gln or a naturally or
      non-naturally occurring amino acid
<221> NAME/KEY: VARIANT
<222> LOCATION: 10
<223> OTHER INFORMATION: Xaa = Absent or Gly or a small naturally or
      non-naturally occurring amino acid
<221> NAME/KEY: VARIANT
<222> LOCATION: 11
<223> OTHER INFORMATION: Xaa = Absent or Ala or His or Glu or Asp or
      a hydrophobic or a small or an acidic naturally or
      non-naturally occurring amino acid
<221> NAME/KEY: VARIANT
<222> LOCATION: 12
<223> OTHER INFORMATION: Xaa = Absent or Ala or Pro or Gln or Ser or Arg
      or His or a hydrophobic or a small naturally or non- naturally
      occurring amino acid
<221> NAME/KEY: VARIANT
<222> LOCATION: 13
<223> OTHER INFORMATION: Xaa = Absent or Cys or Val or a hydrophobic
      naturally or non-naturally occurring amino acid
<221> NAME/KEY: VARIANT
<222> LOCATION: 14
<223> OTHER INFORMATION: Xaa = Absent or Arg or Lys or Gln or Pro or a
      basic or a polar naturally or non-naturally occurring amino acid
<221> NAME/KEY: VARIANT
<222> LOCATION: 15
<223> OTHER INFORMATION: Xaa = Absent or Arg or Gln or Ser or a basic or
      a polar naturally or non-naturally occurring amino acid
<221> NAME/KEY: VARIANT
<222> LOCATION: 16
<223> OTHER INFORMATION: Xaa = Absent or Ala or Leu or His or Gln or a
      hydrophobic or a small naturally or non-naturally occurring amino
      acid
<221> NAME/KEY: VARIANT
<222> LOCATION: 17
<223> OTHER INFORMATION: Xaa = Absent or Tyr or a hydrophobic or an
      aromatic naturally or non-naturally occurring amino acid
<221> NAME/KEY: VARIANT
<222> LOCATION: 18
<223> OTHER INFORMATION: Xaa = Absent or Ala or a hydrophobic or small
      naturally or non-naturally occurring amino acid
<221> NAME/KEY: VARIANT
<222> LOCATION: 19
<223> OTHER INFORMATION: Xaa = Absent or Ala or a hydrophobic small
      naturally or non-naturally occurring amino acid
<221> NAME/KEY: VARIANT
<222> LOCATION: 20
<223> OTHER INFORMATION: Xaa = Absent or Phe or a hydrophobic or an
      aromatic naturally or non-naturally occurring amino acid
<221> NAME/KEY: VARIANT
<222> LOCATION: 21
<223> OTHER INFORMATION: Xaa = Absent or Ser or Thr or a polar naturally
      or non-naturally occurring amino acid
<221> NAME/KEY: VARIANT
<222> LOCATION: 22
<223> OTHER INFORMATION: Xaa = Absent or Val or a hydrophobic naturally
```

```
      or non-naturally occurring amino acid
<221> NAME/KEY: VARIANT
<222> LOCATION: 23
<223> OTHER INFORMATION: Xaa = Absent or Gly or hydrophobic or small
      non-naturally occurring amino acid
<221> NAME/KEY: VARIANT
<222> LOCATION: 24
<223> OTHER INFORMATION: Xaa = Absent or Arg or a basic naturally or
      non-naturally occurring amino acid
<221> NAME/KEY: VARIANT
<222> LOCATION: 25
<223> OTHER INFORMATION: Xaa = Absent or Arg or a basic naturally or
      non-naturally occurring amino acid
<221> NAME/KEY: VARIANT
<222> LOCATION: 26
<223> OTHER INFORMATION: Xaa = Ala or a hydrophobic or small naturally
      or non-naturally occurring amino acid
<221> NAME/KEY: VARIANT
<222> LOCATION: 27
<223> OTHER INFORMATION: Xaa = Tyr or a hydrophobic or an aromatic
      naturally or non-naturally occurring amino acid
<221> NAME/KEY: VARIANT
<222> LOCATION: 28
<223> OTHER INFORMATION: Xaa = Ala or a hydrophobic or small naturally
      or non-naturally occurring amino acid
<221> NAME/KEY: VARIANT
<222> LOCATION: 29
<223> OTHER INFORMATION: Xaa = Ala or a hydrophobic or small naturally
      or non-naturally occurring amino acid
<221> NAME/KEY: VARIANT
<222> LOCATION: 30
<223> OTHER INFORMATION: Xaa = Phe or a hydrophobic naturally or
      non-naturally occurring amino acid
<221> NAME/KEY: VARIANT
<222> LOCATION: 31
<223> OTHER INFORMATION: Xaa = Ser or Thr or a polar naturally or
      non-naturally occurring amino acid
<221> NAME/KEY: VARIANT
<222> LOCATION: 32
<223> OTHER INFORMATION: Xaa = Val or a hydrophobic naturally or
      non-naturally occurring amino acid
<221> NAME/KEY: VARIANT
<222> LOCATION: 33
<223> OTHER INFORMATION: Xaa = Absent or Gly or hydrophobic or small
      naturally or non-naturally occurring amino acid

<400> SEQUENCE: 4

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa Xaa
            20                  25                  30

Xaa

<210> SEQ ID NO 5
<211> LENGTH: 22
<212> TYPE: PRT
<213> ORGANISM: Homo sapiens

<400> SEQUENCE: 5

Gly Gln Lys Gly Gln Val Gly Pro Pro Gly Ala Ala Val Arg Arg Ala
 1               5                   10                  15

Tyr Ala Ala Phe Ser Val
            20

<210> SEQ ID NO 6
<211> LENGTH: 32
<212> TYPE: PRT
<213> ORGANISM: Homo sapiens

<400> SEQUENCE: 6

Gly Gln Lys Gly Gln Val Gly Pro Pro Gly Ala Ala Val Arg Arg Ala
 1               5                   10                  15
```

Tyr Ala Ala Phe Ser Val Gly Arg Arg Ala Tyr Ala Ala Phe Ser Val
            20                  25                  30

<210> SEQ ID NO 7
<211> LENGTH: 23
<212> TYPE: PRT
<213> ORGANISM: Homo sapiens

<400> SEQUENCE: 7

Gly Gln Lys Gly Gln Val Gly Pro Pro Gly Ala Ala Cys Arg Arg Ala
1               5                   10                  15

Tyr Ala Ala Phe Ser Val Gly
            20

<210> SEQ ID NO 8
<211> LENGTH: 262
<212> TYPE: PRT
<213> ORGANISM: Homo sapiens

<400> SEQUENCE: 8

Met Ala Ala Pro Ala Leu Leu Leu Ala Leu Leu Pro Val Gly
1               5                   10                  15

Ala Trp Pro Gly Leu Pro Arg Arg Pro Cys Val His Cys Cys Arg Pro
            20                  25                  30

Ala Trp Pro Pro Gly Pro Tyr Ala Arg Val Ser Asp Arg Asp Leu Trp
        35                  40                  45

Arg Gly Asp Leu Trp Arg Gly Leu Pro Arg Val Arg Pro Thr Ile Asp
    50                  55                  60

Ile Glu Ile Leu Lys Gly Glu Lys Gly Glu Ala Gly Val Arg Gly Arg
65                  70                  75                  80

Ala Gly Arg Ser Gly Lys Glu Gly Pro Pro Gly Ala Arg Gly Leu Gln
                85                  90                  95

Gly Arg Arg Gly Gln Lys Gly Gln Val Gly Pro Pro Gly Ala Ala Cys
            100                 105                 110

Arg Arg Ala Tyr Ala Ala Phe Ser Val Gly Arg Arg Ala Tyr Ala Ala
        115                 120                 125

Phe Ser Val Gly Arg Arg Glu Gly Leu His Ser Ser Asp His Phe Gln
    130                 135                 140

Ala Val Pro Phe Asp Thr Glu Leu Val Asn Leu Asp Gly Ala Phe Asp
145                 150                 155                 160

Leu Ala Ala Gly Arg Phe Leu Cys Thr Val Pro Gly Val Tyr Phe Leu
                165                 170                 175

Ser Leu Asn Val His Thr Trp Asn Tyr Lys Glu Thr Tyr Leu His Ile
            180                 185                 190

Met Leu Asn Arg Arg Pro Ala Ala Val Leu Tyr Ala Gln Pro Ser Glu
        195                 200                 205

Arg Ser Val Met Gln Ala Gln Ser Leu Met Leu Leu Ala Ala Gly
    210                 215                 220

Asp Ala Val Trp Val Arg Met Phe Gln Arg Asp Arg Asp Asn Ala Ile
225                 230                 235                 240

Tyr Gly Glu His Gly Asp Leu Tyr Ile Thr Phe Ser Gly His Leu Val
                245                 250                 255

Lys Pro Ala Ala Glu Leu
            260

METHOD OF TREATING DYSPNEA ASSOCIATED WITH ACUTE HEART FAILURE

RELATED APPLICATIONS

This application is a continuation of application Ser. No. 12/467,214 filed on May 15, 2009 and granted as U.S. Pat. No. 8,053,411 on Nov. 8, 2011, which claims benefit of U.S. Provisional Application No. 61/164,333 filed on Mar. 27, 2009, U.S. Provisional Application No. 61/201,240 filed on Dec. 8, 2008, U.S. Provisional Application No. 61/190,545 filed on Aug. 28, 2008, and U.S. Provisional Application No. 61/127,889 filed on May 16, 2008, the entire disclosures of which are hereby incorporated by reference.

FIELD

The present disclosure relates to methods for treating decompensation in human subjects afflicted with symptoms of acute decompensated heart failure. The methods described herein employ administration of relaxin.

BACKGROUND

Acute heart failure (AHF) or acute decompensated heart failure (ADHF) encompasses a heterogeneous group of disorders that typically includes dyspnea (shortness of breath), edema (fluid retention) and fatigue. For example, a patient who presents with shortness of breath from an exacerbation of congestive heart failure would fall within the group of AHF patients. However, the diagnosis of AHF can be difficult and the optimal treatment remains poorly defined despite the high prevalence of this condition and its association with major morbidity and mortality. The difficulties surrounding treatment begin with the lack of a clear definition of the disease. The term "acute decompensated heart failure" broadly represents new or worsening symptoms or signs of dyspnea, fatigue or edema that lead to hospital admission or unscheduled medical care. These symptoms are consistent with an underlying worsening of left ventricular function. "Acute heart failure" is sometimes defined as the onset of symptoms or signs of heart failure in a patient with no prior history of heart failure and previously normal function. This is an uncommon cause of AHF, particularly in patients without concomitant acute coronary syndromes. More frequently, AHF occurs in patients with previously established myocardial dysfunction (systolic or diastolic) such as in congestive heart failure (CHF) patients who present with an exacerbation of symptoms or signs after a period of relative stability (Allen and O'Connor, *CMAJ* 176(6):797-805, 2007). Consequently, AHF can result without prior history of CHF, be based on a pathophysiological origin in prior CHF patients (functional), or be the result of anatomic causes in prior CHF patients (structural). Thus, AHF can be a functional and/or a structural disease.

The identification of the acute triggers for the decompensation, as well as noninvasive characterization of cardiac filling pressures and cardiac output is central to management. Diuretics, vasodilators, continuous positive airway pressure and inotropes can be used to alleviate symptoms. However, there are no agents currently available for the treatment of AHF that have been shown (in large prospective randomized clinical trials) to provide significant improvements in inter-mediate-term clinical outcomes.

AHF is the single most costly hospital admission diagnosis according to the Center for Medicare and Medicaid Administration. AHF accounts for more than one million hospitalizations per year and re-hospitalizations within six months are as high as fifty percent. The annual mortality rate approaches fifty percent (for those patients with New York Heart Association class III or IV symptoms). Generally, non-aggressive medical care during the initial hospitalization, sub-optimal treatment before re-admission, and patient non-compliance contribute strongly to the high readmission rate. Fifty percent of patients with classic AHF symptoms before admission receive no alteration in their treatment at the initial consultation with their health care provider (McBride et al., *Pharmacotherapy* 23(8):997-1020, 2003).

While AHF was traditionally viewed as a disorder associated with sodium and water retention and left ventricular (LV) dysfunction, it is now also understood to be associated with neurohormonal activation (Schrier et al., *The New England Journal of Medicine* 341(8):577-585, 1999). As indicated above, the clinical syndrome of AHF is characterized by the development of dyspnea associated with the rapid accumulation of fluid within the lung's interstitial and alveolar spaces, resulting from acutely elevated cardiac filling pressures (cardiogenic pulmonary edema). More specifically, AHF can also present as elevated left ventricular filling pressures and dyspnea without pulmonary edema. It is most commonly due to left ventricular systolic or diastolic dysfunction, with or without additional cardiac pathology, such as coronary artery disease or valve abnormalities. In addition, a variety of conditions or events can cause cardiogenic pulmonary edema due to an elevated pulmonary capillary wedge pressure in the absence of heart disease, including severe hypertension, particularly renovascular hypertension, and severe renal disease.

Hospital admissions for AHF have increased during the past few decades and are projected to continue to increase in the future. AHF is usually diagnosed and managed based on tradition rather than evidence. In order to reduce the costs associated with this disorder and optimize patient outcomes, new approaches and better treatment options are essential. Diuretic therapy has been the main treatment for symptom relief for pulmonary congestion and fluid retention. Continuous infusions of loop diuretic therapy rather than bolus dosing may enhance efficacy and reduce the extent of diuretic resistance. Catecholamine- and phosphodiesterase-based inotropic therapies are efficacious, but the increased risk of arrhythmogenesis and the potential for negative effects on survival limit their use. NATROCOR (nesiritide marketed by Scios) used in vasodilator therapy, is a pharmacological preload and afterload reducer, but based on clinical trial evidence should be reserved for those with resistance to intravenous nitrate therapy (McBride et al., supra). Vasopressin receptor antagonists and adenosine receptor antagonists offer some improved renal preservation during aggressive diuresis (Tang et al., *Current Cardiology Reviews* 1(1):1-5, 2005).

Volume and perfusion status provide useful clues to a patient's cardiac performance and help shape the treatment plan for patients with AHF. Caregivers must frequently reassess the patient's hemodynamic status to determine volume and perfusion status. Volume status is determined by assessing if the patient is wet, dry, or has a balanced fluid level (hypervolemia, hypovolemia, or euvolemia, respectively), and perfusion is assessed by determining if the patient is cold, cool/lukewarm, or warm (has perfusion that is very low, slightly low, or normal, respectively). Evidence of congestion includes the signs of neck vein distension, elevated pressure in the right internal jugular vein, positive abdominal-jugular neck vein reflex, edema, ascites, and crackles (rarely), as well as the symptoms of dyspnea, orthopnea, and paroxysmal nocturnal dyspnea. In addition, various tests can be performed at the time of admission including chest radiographs, arterial blood gas levels, liver function tests, hematologic tests, electrocardiograms, and basic metabolic profile. The findings on physical examination and the results of assays of serum levels of natriuretic peptides can be used to guide treatment in patients with acute decompensated heart failure. Brain natriuretic peptide or B-type natriuretic peptide (BNP) is secreted mainly from the ventricular myocardium in response to elevations in end-diastolic pressure and ventricular volume expansion. The measurement of BNP can aid in diagnosis of CHF as AHF, and BNP levels can also be used to assess clinical status and the effectiveness of therapies during an admission for acute decompensation (Albert et al., *Critical Care Nurse* 24(6):14-29, 2004).

While significant advances have been made in the realm of chronic heart failure management, clinicians continue to grapple with optimal strategies to treat acutely decompensated patients including patients afflicted with AHF. There is now an increasing awareness of the complex interplay that occurs between the heart and kidneys among patients with heart failure. As such, many of the traditional therapeutics used to treat this patient population can significantly alter renal function and are, thus, no longer considered optimal treatment options. A more comprehensive approach is desired and the present disclosure addresses this need.

BRIEF SUMMARY OF PREFERRED EMBODIMENTS

The present disclosure provides methods for treating conditions associated with acute decompensated heart failure (AHF) by administering relaxin. The number of hospital admissions due to AHF related symptoms are on the steady rise and the cost associated with caring for this population of patients is staggering. Thus, a new therapeutic approach is needed and the disclosure addresses this need. One advantage of this disclosure is that the administration of relaxin results in a balanced vasodilation that prevents subjects diagnosed with conditions associated with AHF from further deteriorating. As such, the subjects can be maintained at a steady-state level where hospitalization is not required and the number or duration of hospital visits is significantly reduced. Another advantage of the present disclosure is that relaxin, when administered to patients, shows effectiveness with little to no adverse drug reactions (ADRs). Herein, relaxin is shown to have a beneficial effect on reducing acute decompensation without causing ADRs. Thus, the present disclosure provides a treatment that leads to balanced vasodilation in a specific patient population that suffers from acute decompensation and is specifically suited to benefit from relaxin treatment.

One aspect of the disclosure provides a method of reducing acute cardiac decompensation events including selecting a human subject with acute cardiac decompensation, wherein the subject has a vasculature and the vasculature has relaxin receptors. The method further includes administering to the subject a pharmaceutical formulation including pharmaceutically active relaxin in an amount effective to reduce acute cardiac decompensation in the subject by binding to the relaxin receptors in the vasculature of the subject, resulting in balanced vasodilation. The cardiac decompensation can be due to any one or more causes, including but not limited to, neurohormonal imbalance, fluid overload, cardiac arrhythmia, and cardiac ischemia. In one embodiment, the human subject suffers from acute vascular failure.

Relaxin employed in the pharmaceutical formulations of the disclosure can be, for example, synthetic or recombinant relaxin, or a pharmaceutically effective relaxin agonist. In one embodiment of the disclosure, relaxin is H1 human relaxin. In another embodiment, relaxin is H2 human relaxin. In yet another embodiment, relaxin is H3 human relaxin. In a further embodiment, relaxin is synthetic or recombinant human relaxin, or a pharmaceutically effective relaxin agonist. Thus, the subject can be treated with a pharmaceutical formulation of synthetic or recombinant human relaxin or relaxin agonist. In one embodiment of the disclosure, the subject is treated with synthetic human relaxin. In another embodiment, the subject is treated with recombinant human relaxin. In yet another embodiment, the subject is treated with a pharmaceutically effective relaxin agonist. Relaxin can be administered to the subject through a number of different routes, including but not limited to, intravenously, subcutaneously, intramuscularly, sublingually and via inhalation. More specifically, the pharmaceutical formulation of relaxin or relaxin agonist can be administered to the subject in an amount in a range of about 10 to 1000 µg/kg of subject body weight per day. As such, relaxin is administered to the subject so as to maintain a serum concentration of relaxin of from about 1 to 500 ng/ml.

Human subjects that would benefit from the methods of the disclosure usually present with acute cardiac decompensation events, including but not limited to, dyspnea, hypertension, arrhythmia, reduced renal blood flow, and renal insufficiency, wherein these events are often associated with readmission to the hospital. In one embodiment of the disclosure, these acute cardiac decompensation events are pathophysiological in nature. Most commonly, such events are associated with acute decompensated heart failure (AHF). In one embodiment, the human subject suffers from acute vascular failure. In another embodiment, the acute cardiac decompensation is intermittent. In an alternative embodiment, the acute cardiac decompensation is chronic.

Another aspect of the disclosure provides a method of treating acute cardiac decompensation associated with acute decompensated heart failure (AHF). The method includes selecting a human subject with acute cardiac decompensation, wherein the subject has a vasculature and the vasculature has relaxin receptors, and further, administering to the subject a pharmaceutical formulation including pharmaceutically active relaxin or pharmaceutically effective relaxin agonist. Relaxin is administered in an amount effective to reduce the acute cardiac decompensation in the subject by binding to the relaxin receptors in the vasculature of the subject, resulting in balanced vasodilation. The cardiac decompensation can be due to any one or more causes, including but not limited to, neurohormonal imbalance, fluid overload, cardiac arrhythmia, and cardiac ischemia. In one embodiment, the human subject suffers from acute vascular failure.

The disclosure further encompasses a method of treating acute cardiac decompensation associated with acute decompensated heart failure (AHF), including administering a formulation which includes pharmaceutically active synthetic human relaxin or pharmaceutically effective relaxin agonist to a human subject in an amount in a range of about 10 to 1000 µg/kg of subject body weight per day, and continuing the administration over a period of time sufficient to achieve an amelioration in acute cardiac decompensation events, including but not limited to, dyspnea, hypertension, arrhythmia, reduced renal blood flow, and renal insufficiency. In one preferred embodiment, pharmaceutically effective relaxin or an agonist thereof is administered at about 30 µg/kg/day which results in serum concentrations of 10 ng/ml. In another preferred embodiment, pharmaceutically effective relaxin or an agonist thereof is administered at about 10 to about 250 µg/kg/day. The amelioration may manifest itself as a reduced number of acute cardiac decompensation events and/or less severe acute cardiac decompensation events in the subject. In one embodiment, the human subject suffers from acute vascular failure.

Still, another aspect of the disclosure provides a method of treating acute decompensated heart failure (AHF) in a human subject who also suffers from renal insufficiency. This method includes selecting a human subject with symptoms of acute cardiac decompensation and renal insufficiency, wherein the subject has a systemic and renal vasculature comprising relaxin receptors. The method further includes administering to the subject a pharmaceutical formulation comprising pharmaceutically active relaxin or pharmaceutically effective relaxin agonist, wherein relaxin performs a dual action by binding to the relaxin receptors in the systemic and renal vasculature of the subject, resulting in balanced vasodilation. In one embodiment, the human subject suffers from acute vascular failure. The cardiac decompensation can be due to any one or more causes, including but not limited to, neurohormonal imbalance, fluid overload, cardiac arrhythmia, and cardiac ischemia. The subject may suffer from symptoms such as dyspnea, hypertension, arrhythmia, reduced renal blood flow, and the like, wherein the symptoms are commonly further associated with readmission to the hospital. Notably, the subject may be further experiencing elevated levels of brain natriuretic peptide (BNP). In addition, a reversal of the acute cardiac decompensation may occur in combination with a decrease in circulating levels of BNP.

Another aspect of the present disclosure provides a method of modulating endothelin in a human subject, including selecting a human subject with a neurohormonal imbalance, wherein the subject has a vasculature and the vasculature has relaxin receptors. The method further includes administering to the subject a pharmaceutical formulation which includes pharmaceutically active relaxin or pharmaceutically effective relaxin agonist in an amount effective to reduce the neurohormonal imbalance in the subject by binding to the relaxin receptors in the vasculature of the subject, resulting in balanced vasodilation. In one embodiment, the human subject suffers from acute vascular failure.

The disclosure further contemplates a method of reducing mortality risk in a human patient with symptoms of acute cardiac decompensation. This method includes selecting a human subject with acute cardiac decompensation, wherein the subject has a vasculature and the vasculature has relaxin receptors, and administering to the subject a pharmaceutical formulation including pharmaceutically active relaxin or pharmaceutically effective relaxin agonist. The relaxin is administered in an amount effective to reduce the acute cardiac decompensation in the subject by binding to the relaxin receptors in the vasculature of the subject, thereby resulting in reduced levels of brain natriuretic peptide (BNP). The reduced levels of BNP can be physically measured in order to predict risk of mortality in the patient. Generally, the reduced levels of BNP are due to reduced cardiac stress following a reduction in vascular resistance. The reduction in vascular resistance is in turn due to the balanced vasodilation which is the result of relaxin binding to relaxin receptors that are found on smooth muscle cells of the renal vasculature. In one embodiment, the human subject suffers from acute vascular failure.

Generally, the reversal of the acute cardiac decompensation in the subjects occurs through activation of specific relaxin receptors such as the LGR7 and LGR8 receptors. In particular, LGR7 and LGR8 receptors are activated through the binding of relaxin or a relaxin agonist, wherein the binding triggers the production of nitric oxide (NO) which results in a balanced vasodilation. These relaxin specific receptors are located on smooth muscle tissue of the vasculature which includes systemic and renal vasculature.

Yet another aspect of the disclosure provides a method of reducing acute cardiac decompensation events, including selecting a human subject with acute cardiac decompensation, wherein the subject has a vasculature and the vasculature has relaxin receptors. The method further includes administering to the subject a pharmaceutical formulation including pharmaceutically active relaxin or pharmaceutically effective relaxin agonist in an amount effective to reduce acute cardiac decompensation in the subject by binding to the relaxin receptors in the vasculature of the subject, resulting in balanced vasodilation, wherein the relaxin is administered to the subject so as to maintain a serum concentration of relaxin of equal or greater than about 3 ng/ml. The method further includes administering to the subject a pharmaceutical formulation including pharmaceutically active relaxin or pharmaceutically effective relaxin agonist in an amount effective to reduce acute cardiac decompensation in the subject by binding to the relaxin receptors in the vasculature of the subject, resulting in balanced vasodilation, wherein the relaxin is administered to the subject so as to maintain a serum concentration of relaxin of equal or greater than about 10 ng/ml. In one embodiment, the human subject suffers from acute vascular failure.

Still, another aspect of the disclosure provides relaxin for use in the treatment of acute cardiac decompensation. The acute cardiac decompensation is commonly associated with acute decompensated heart failure (AHF). The method includes selecting a human subject with acute cardiac decompensation, wherein the subject has a vasculature and the vasculature has relaxin receptors, and further, administering to the subject a pharmaceutical formulation including pharmaceutically active relaxin or pharmaceutically effective relaxin agonist. In one embodiment, the human subject suffers from acute vascular failure. Relaxin or a relaxin agonist is administered in an amount effective to reduce the acute cardiac decompensation in the subject by binding to the relaxin receptors in the vasculature of the subject, resulting in balanced vasodilation. The cardiac decompensation can be due to any one or more causes, including but not limited to, neurohormonal imbalance, fluid overload, cardiac arrhythmia, and cardiac ischemia. The disclosure also contemplates relaxin for use in reducing acute cardiac decompensation events.

The disclosure further encompasses relaxin for use in treating acute decompensated heart failure (AHF) in a human subject who also suffers from renal insufficiency; relaxin for use in modulating endothelin in a human subject; and relaxin for use in reducing mortality risk in a human patient with symptoms of acute cardiac decompensation as discussed herein.

Another aspect of the disclosure provides a method of reducing acute cardiac decompensation events. The method includes selecting a human subject with acute cardiac decompensation, wherein the subject has a vasculature and the vasculature has relaxin receptors; and administering to the subject a pharmaceutical formulation including pharmaceutically active relaxin in an amount effective to reduce acute cardiac decompensation in the subject by binding to the relaxin receptors in the vasculature of the subject. In this method, treatment with relaxin results in a reduction of acute cardiac decompensation events lasting for at least about 1 to 14 days from onset of relaxin treatment. The acute cardiac decompensation events include, but are not limited to dyspnea, extra body weight due to retention of fluids, length of hospital stay, likelihood of hospital re-admission, need for loop diuretics, need for intravenous nitroglycerin, and an incidence of worsening heart failure. In one embodiment, the patients are treated with relaxin for 48 hours. In another embodiment, the patients are treated with relaxin for 24 hours. In yet another embodiment, the patients are treated with relaxin for 12 hours. In still another embodiment, the patients are treated with relaxin for 6 hours. The effects of relaxin can be measured at any time point, for example, at 1 day, 2 days, 3 days, 4 days, 5 days, 6 days, 7 days, 8 days, 9 days, 10 days, 11 days, 12 days, 13 days, 14 days or later.

In one preferred embodiment, relaxin is administered at about 30 mcg/kg/day. In one preferred embodiment, relaxin is administered at about 30 mcg/kg/day. In another preferred embodiment, relaxin is administered at about 35 mcg/kg/day. In another preferred embodiment, relaxin is administered at about 40 mcg/kg/day. In another preferred embodiment, relaxin is administered at about 45 mcg/kg/day. In another preferred embodiment, relaxin is administered at about 50 mcg/kg/day. In another preferred embodiment, relaxin is administered at about 55 mcg/kg/day. In another preferred embodiment, relaxin is administered at about 60 mcg/kg/day. In another preferred embodiment, relaxin is administered at about 65 mcg/kg/day. In another preferred embodiment, relaxin is administered at about 70 mcg/kg/day. In another preferred embodiment, relaxin is administered at about 75 mcg/kg/day. In another preferred embodiment, relaxin is administered at about 80 mcg/kg/day. In another preferred embodiment, relaxin is administered at about 85 mcg/kg/day. In another preferred embodiment, relaxin is administered at about 100 mcg/kg/day. Relaxin may also be administered at a dosage of 90 to 200 mcg/kg/day. Pharmaceutically effective relaxin includes recombinant or synthetic H1 human relaxin, H2 human relaxin or H3 human relaxin or an agonist or a variant thereof. In one preferred embodiment, relaxin is administered to the subject so as to maintain a serum concentration of about 10 ng/ml. The pharmaceutical formulation of relaxin can be administered intravenously, subcutaneously, intramuscularly, sublingually or via inhalation. In one preferred embodiment, the pharmaceutical formulation of relaxin is administered intravenously. The relaxin receptors are activated through the binding of relaxin and include, but are not limited to, LRG7, LGR8, GPCR135, and GPCR142. The binding of relaxin to the relaxin receptors triggers the production of nitric oxide (NO) which results in balanced vasodilation. The relaxin receptors are located, for example, on the smooth muscle tissue of the vasculature.

The present disclosure also provides a method for treating a cardiovascular condition comprising: administering to a human subject a pharmaceutically active H2 relaxin in an amount effective to treat the cardiovascular condition, wherein the cardiovascular condition is diagnosed based on the presence of two or more of the group consisting of dyspnea at rest or with minimal exertion, pulmonary congestion on chest X-ray, and elevated natriuretic peptide levels [brain natriuretic peptide (BNP)$\geq$350 pg/mL or NT-pro-BNP$\geq$1400 pg/mL]. In some embodiments, the cardiovascular condition is acute heart failure and the two or more comprise dyspnea at rest or with minimal exertion, and pulmonary congestion on chest X-ray. In some embodiments, the cardiovascular condition is acute heart failure and the two or more comprise dyspnea at rest or with minimal exertion, and elevated natriuretic peptide levels [brain natriuretic peptide (BNP)$\geq$350 pg/mL or NT-pro-BNP$\geq$1400 pg/mL]. In some embodiments, the cardiovascular condition is acute heart failure and the two or more comprise pulmonary congestion on chest X-ray and elevated natriuretic peptide levels [brain natriuretic peptide (BNP)$\geq$350 pg/mL or NT-pro-BNP$\geq$1400 pg/mL]. In some preferred embodiments, the subject is a male or a nonpregnant female. In some preferred embodiments, the subject has a systolic blood pressure of at least about 125 mmHg.

In addition, the present disclosure provides a method for treating dyspnea associated with acute heart failure, comprising: administering to a human subject a pharmaceutically active H2 relaxin in an amount effective to reduce dyspnea in the subject, wherein the subject has dyspnea associated with acute heart failure and is in a hypertensive or normotensive state at the onset of the administering. In some embodiments, the methods further comprise selecting the human subject having dyspnea associated with acute heart failure and in a hypertensive or normotensive state, prior to the administering step. In some embodiments, the H2 relaxin is administered for at least 24 or 48 hours, while in others the H2 relaxin is administered over 48 hours. In some embodiments, the H2 relaxin is administered at an intravenous infusion rate in the range of about 10 µg/kg/day to about 250 µg/kg/day, in a range of about 30 µg/kg/day to about 100 µg/kg/day, or at about 30 µg/kg/day. In some embodiments, the reduction in dyspnea is statistically significant at 6 hours after the onset of treatment compared to treatment without H2 relaxin, at 12 hours after the onset of treatment compared to treatment without H2 relaxin, or at 6, 12 and 24 hours after the onset of treatment compared to placebo. In some embodiments, the reduction in dyspnea lasts for at least about twice the duration of treatment, at least about 4 times the duration of treatment, or at least about 7 times the duration of treatment. In some embodiments, the methods further comprise reducing the body weight of the subject by at least about 0.5 kg over a 14-day period compared to treatment without H2 relaxin, or at least about 1 kg over a 14-day period compared to treatment without H2 relaxin. In some embodiments, the subject is renally impaired. In a subset of these embodiments, the subject has a creatinine clearance in the range of about 35 to about 75 mL/min. In some embodiments, the methods further comprise reducing the 60-day risk of death or rehospitalization of the subject compared to treatment of acute decompensated heart failure without H2 relaxin. In a subset of these embodiments, the 60-day risk of death or rehospitalization is reduced by at least 50%. In some preferred embodiments, the subject has dyspnea requiring hospitalization. In some embodiments, the methods further comprise reducing the hospitalization length of stay by at least one day compared to treatment of acute decompensated heart failure without H2 relaxin. In some methods, the H2 relaxin is administered at an intravenous infusion rate in the range of about 30 µg/kg/day and the hospitalization length of stay is reduced by at least two days compared to treatment of acute decompensated heart failure without H2 relaxin. In some embodiments, the methods further comprise reducing the 60-day risk of rehospitalization due to heart failure or renal insufficiency of the subject compared to treatment of acute decompensated heart failure without H2 relaxin. In some preferred embodiments, the 60-day risk of rehospitalization due to heart failure or renal insufficiency is reduced by at least about 50%. In some methods, the H2 relaxin is administered at an intravenous infusion rate in the range of about 30 µg/kg/day and the 60-day risk of rehospitalization due to heart failure or renal insufficiency is reduced by at least about 70%. In some embodiments, the methods comprise reducing the 180-day risk of cardiovascular death of the subject compared to treatment of acute decompensated heart failure without H2 relaxin. In some preferred embodiments, the 180-day risk of cardiovascular death is reduced by at least about 50%. In some embodiments, the H2 relaxin is administered at an intravenous infusion rate less than about 250 µg/kg/day and the 180-day risk of cardiovascular death is reduced by at least about 70%. In some embodiments, the methods further comprise reducing the 180-day risk of all-cause mortality of the subject compared to treatment of acute decompensated heart failure without H2 relaxin. In some preferred embodiments, the 180-day risk of all-cause mortality is reduced by at least about 25%. In some embodiments, the H2 relaxin is administered at an intravenous infusion rate less than about 250 µg/kg/day and the 180-day risk of all-cause mortality is reduced by at least about 50%. In some preferred embodiments, the subject is a male or a nonpregnant female. In some preferred embodiments, the subject has a systolic blood pressure of at least about 125 mmHg.

The disclosure further provides a method for treating dyspnea associated with acute decompensated heart failure, comprising: administering to a human subject a pharmaceutically active H2 relaxin in an amount effective to reduce dyspnea in the subject, wherein the subject has dyspnea associated with acute decompensated heart failure and at least one indicia of cardiac ischemia. In some embodiments, the method further comprises selecting the human subject having dyspnea associated with acute decompensated heart failure and at least one indicia of cardiac ischemia, prior to the administering step. In some embodiments, the at least one indicia of cardiac ischemia is selected from the group consisting of a positive troponin test, an abnormal electrocardiogram, the presence of chest pain, the presence of an arrhythmia, a positive creatine kinase-MB test, and an abnormal echocardiogram. In some embodiments of the method, the subject also has a left ventricular ejection fraction in the range of 20-40%. In another embodiment, the subject has a left ventricular ejection fraction of at least 40%. In some embodiments of the method, the subject is normotensive or hypertensive. In another embodiment, the subject has a systolic blood pressure of at least about 125 mm Hg. In some embodiments of the method, the subject is renally impaired. In another embodiment, the subject has a creatinine clearance in the range of about 35 to about 75 mL/min. In some embodiments of the method for treating a cardiovascular condition, the H2 relaxin is administered for at least 24 or 48 hours. In another embodiment, the H2 relaxin is administered over 48 hours. In yet another embodiment, the H2 relaxin is administered at an infusion rate in the range of about 10 µg/kg/day to about 960 µg/kg/day. In yet another embodiment of the method, the H2 relaxin is administered at an intravenous infusion rate in the range of about 10 µg/kg/day to about 250 µg/kg/day. In yet another embodiment, the H2 relaxin is administered at an intravenous infusion rate in the range of about 30 µg/kg/day to about 100 µg/kg/day. In yet another embodiment, the H2 relaxin is administered at an intravenous infusion rate in the range of about 30 µg/kg/day. In some embodiments of the method, the subject has dyspnea requiring hospitalization. In some preferred embodiments, the subject is a male or a nonpregnant female.

The disclosure further provides a method for treating acute decompensated heart failure, comprising: a) identifying a subject with acute decompensated heart failure; b) assessing the orthopnea status in the subject; c) selecting an initial dosage of a pharmaceutically active H2 relaxin based upon the orthopnea status in the patient; and d) administering the dosage to the subject. In some embodiments of the method, the selected initial dosage is higher in the presence of orthopnea than in the absence of orthopnea. In some embodiments, the selected initial dosage is at least about 30 µg/kg/day but below about 100 µg/kg/day in the presence of orthopnea. In some preferred embodiments, the subject is a male or a nonpregnant female. In some preferred embodiments, the subject has a systolic blood pressure of at least about 125 mmHg.

The disclosure further provides a method for treating dyspnea associated with acute decompensated heart failure, comprising: administering to a human subject a pharmaceutically active H2 relaxin in an amount effective to reduce dyspnea in the subject, wherein the subject has acute decompensated heart failure and a left ventricular ejection from of at least 20%. In some embodiments, the method further comprises selecting the human subject having acute decompensated heart failure and a left ventricular ejection from of at least 20%, prior to the administering step. In some embodiments, the subject has a left ventricular ejection fraction of at least about 20%. In some embodiments of the method, the subject has a left ventricular ejection fraction of at least about 40%. In one embodiment, the subject is normotensive, while in other embodiments the subject is hypertensive. In some embodiments, the subject has a systolic blood pressure of at least about 125 mm Hg. In another embodiment, the subject is renally impaired. In another embodiment, the subject has a creatinine clearance in the range of about 35 to about 75 mL/min. In another embodiment of the method, the H2 relaxin is administered for at least 24 or 48 hours. In yet another embodiment, the H2 relaxin is administered over 48 hours. In yet another embodiment, the H2 relaxin is administered at an infusion rate in the range of about 10 µg/kg/day to about 960 µg/kg/day. In yet another embodiment, H2 relaxin is administered at an intravenous infusion rate in the range of about 10 µg/kg/day to about 250 µg/kg/day. In yet another embodiment, H2 relaxin is administered at an intravenous infusion rate in the range of about 30 µg/kg/day to about 100 µg/kg/day. In yet another embodiment, H2 relaxin is administered at an intravenous infusion rate in the range of about 30 µg/kg/day. In some embodiments, the methods further comprise reducing the 60-day risk of death or rehospitalization of the subject compared to treatment of acute decompensated heart failure without H2 relaxin. In some embodiments, the 60-day risk of death or rehospitalization is reduced by at least 50%. In some embodiments of the method, the subject has dyspnea requiring hospitalization. In some embodiments, the methods further comprise reducing the hospitalization length of stay by at least one day compared to treatment of acute decompensated heart failure without H2 relaxin. In some embodiments, the H2 relaxin is administered at an intravenous infusion rate in the range of about 30 µg/kg/day and the hospitalization length of stay is reduced by at least two days compared to treatment of acute decompensated heart failure without H2 relaxin. In some embodiments, the methods further comprise reducing the 60-day risk of rehospitalization due to heart failure or renal insufficiency of the subject compared to treatment of acute decompensated heart failure without H2 relaxin. In another embodiment, the 60-day risk of rehospitalization due to heart failure or renal insufficiency is reduced by at least about 50%. In another embodiment, the H2 relaxin is administered at an intravenous infusion rate in the range of about 30 µg/kg/day and the 60-day risk of rehospitalization due to heart failure or renal insufficiency is reduced by at least about 70%. In some embodiments, the methods further comprise reducing the 180-day risk of cardiovascular death of the subject compared to treatment of acute decompensated heart failure without H2 relaxin. In some embodiments, the 180-day risk of cardiovascular death is reduced by at least about 50%. In some embodiments of the method, the H2 relaxin is administered at an intravenous infusion rate less than about 250 µg/kg/day and the 180-day risk of cardiovascular death is reduced by at least about 70%. In some embodiments, the methods further comprise reducing the 180-day risk of all-cause mortality of the subject compared to treatment of acute decompensated heart failure without H2 relaxin. In another embodiment, the 180-day risk of all-cause mortality is reduced by at least about 25%. In another embodiment, the H2 relaxin is administered at an intravenous infusion rate less than about 250 µg/kg/day and the 180-day risk of all-cause mortality is reduced by at least about 50%. In some preferred embodiments, the subject is a male or a nonpregnant female.

The disclosure further provides a method for treating acute decompensated heart failure, comprising: a) selecting a subject with acute decompensated heart failure and a systolic blood pressure of at least 125 mm Hg; and b) administering to the subject a pharmaceutically active H2 relaxin in an amount effective to reduce in-hospital worsening heart failure in the subject. In some embodiments of the method, the subject is renally impaired. In some preferred embodiments, the in-hospital worsening heart failure comprises one or more of worsening dyspnea, need for additional intravenous therapy to treat the heart failure, need for mechanical support of breathing, and need for mechanical support of blood pressure. In another embodiment, the subject has a creatinine clearance in the range of about 35 to about 75 mL/min. In some embodiments, the H2 relaxin is administered for at least 24 or 48 hours. In some embodiments, the H2 relaxin is administered over 48 hours. In another embodiment, the H2 relaxin is administered at an infusion rate in the range of about 10 µg/kg/day to about 960 µg/kg/day. In another embodiment, the H2 relaxin is administered at an intravenous infusion rate in the range of about 10 µg/kg/day to about 250 µg/kg/day. In yet another embodiment, the H2 relaxin is administered at an intravenous infusion rate in the range of about 30 µg/kg/day to about 100 µg/kg/day. In yet another embodiment, the H2 relaxin is administered at an intravenous infusion rate in the range of about 30 µg/kg/day. In some embodiments, the method further comprises reducing the 60-day risk of death or rehospitalization of the subject compared to treatment of acute decompensated heart failure without H2 relaxin. In some embodiments, the 60-day risk of death or rehospitalization is reduced by at least 50%. In some embodiments, the subject has pulmonary congestion as defined by the presence of interstitial edema on chest radiograph. In some embodiments, the method further comprises reducing the hospitalization length of stay by at least one day compared to treatment of acute decompensated heart failure without H2 relaxin. In some embodiments, the H2 relaxin is administered at an intravenous infusion rate in the range of about 30 µg/kg/day and the hospitalization length of stay is reduced by at least two days compared to treatment of acute decompensated heart failure without H2 relaxin. In some embodiments, the method further comprises reducing the 60-day risk of rehospitalization due to heart failure or renal insufficiency of the subject compared to treatment of acute decompensated heart failure without H2 relaxin. In some embodiments, the 60-day risk of rehospitalization due to heart failure or renal insufficiency is reduced by at least about 50%. In some embodiments, the H2 relaxin is administered at an intravenous infusion rate in the range of about 30 µg/kg/day and the 60-day risk of rehospitalization due to heart failure or renal insufficiency is reduced by at least about 70%. In some embodiments, the method further comprises reducing the 180-day risk of cardiovascular death of the subject compared to treatment of acute decompensated heart failure without H2 relaxin. In another embodiment, the 180-day risk of cardiovascular death is reduced by at least about 50%. In another embodiment, the H2 relaxin is administered at an intravenous infusion rate less than about 250 µg/kg/day and the 180-day risk of cardiovascular death is reduced by at least about 70%. In some embodiments, the method further comprises reducing the 180-day risk of all-cause mortality of the subject compared to treatment of acute decompensated heart failure without H2 relaxin. In another embodiment of the method, the 180-day risk of all-cause mortality is reduced by at least about 25%. In another embodiment, the H2 relaxin is administered at an intravenous infusion rate less than about 250 µg/kg/day and the 180-day risk of all-cause mortality is reduced by at least about 50%. In some preferred embodiments, the subject is a male or a nonpregnant female.

The disclosure further provides a method for treating, acute decompensated heart failure comprising: a) selecting a subject with acute decompensated heart failure and a left ventricular ejection fraction of at least about 20%; and b) administering to the subject a pharmaceutically active H2 relaxin in an amount effective to reduce at least one acute heart failure sign or symptom in the subject. In some embodiments, the at least one acute heart failure sign or symptom comprises one or more of the group consisting of dyspnea at rest, orthopnea, dyspnea on exertion, edema, rales, pulmonary congestion, jugular venous pulse or distension, edema associated weight gain, high pulmonary capillary wedge pressure, high left ventricular end-diastolic pressure, high systemic vascular resistance, low cardiac output, low left ventricular ejection fraction, need for intravenous diuretic therapy, need for additional intravenous vasodilator therapy, and incidence of worsening in-hospital heart failure. In another embodiment, the subject has a left ventricular ejection fraction of at least 40%. In another embodiment, the subject is normotensive or hypertensive. In yet another embodiment, the subject has a systolic blood pressure of at least about 125 mm Hg. In some embodiments, the subject is renally impaired. In another embodiment, the subject has a creatinine clearance in the range of about 35 to about 75 mL/min. In some embodiments of the method, the H2 relaxin is administered for at least 24 or 48 hours. In another embodiment, the H2 relaxin is administered over 48 hours. In another embodiment, the H2 relaxin is administered at an infusion rate in the range of about 10 µg/kg/day to about 960 µg/kg/day. In yet another embodiment, the H2 relaxin is administered at an intravenous infusion rate in the range of about 10 µg/kg/day to about 250 µg/kg/day. In yet another embodiment, the H2 relaxin is administered at an intravenous infusion rate in the range of about 30 µg/kg/day to about 100 µg/kg/day. In yet another embodiment, the H2 relaxin is administered at an intravenous infusion rate in the range of about 30 µg/kg/day. In some embodiments, the method further comprises reducing the 60-day risk of death or rehospitalization of the subject compared to treatment of acute decompensated heart failure without H2 relaxin. In some embodiments, the 60-day risk of death or rehospitalization is reduced by at least 50%. In some embodiments, the subject has dyspnea requiring hospitalization. In some embodiments, the method further comprises reducing the hospitalization length of stay by at least one day compared to treatment of acute decompensated heart failure without H2 relaxin. In another embodiment, the H2 relaxin is administered at an intravenous infusion rate in the range of about 30 µg/kg/day and the hospitalization length of stay is reduced by at least two days compared to treatment of acute decompensated heart failure without H2 relaxin. In some embodiments, the method further comprises reducing the 60-day risk of rehospitalization due to heart failure or renal insufficiency of the subject compared to treatment of acute decompensated heart failure without H2 relaxin. In another embodiment, the 60-day risk of rehospitalization due to heart failure or renal insufficiency is reduced by at least about 50%. In another embodiment, the H2 relaxin is administered at an intravenous infusion rate in the range of about 30 μg/kg/day and the 60-day risk of rehospitalization due to heart failure or renal insufficiency is reduced by at least about 70%. In some embodiments, the method further comprises reducing the 180-day risk of cardiovascular death of the subject compared to treatment of acute decompensated heart failure without H2 relaxin. In some embodiments, the 180-day risk of cardiovascular death is reduced by at least about 50%. In another embodiment, the H2 relaxin is administered at an intravenous infusion rate less than about 250 μg/kg/day and the 180-day risk of cardiovascular death is reduced by at least about 70%. In some embodiments, the method further comprises reducing the 180-day risk of all-cause mortality of the subject compared to treatment of acute decompensated heart failure without H2 relaxin. In another embodiment, the 180-day risk of all-cause mortality is reduced by at least about 25%. In another embodiment, the H2 relaxin is administered at an intravenous infusion rate less than about 250 μg/kg/day and the 180-day risk of all-cause mortality is reduced by at least about 50%. In some preferred embodiments, the subject is a male or a nonpregnant female.

The disclosure further provides a method for treating acute decompensated heart failure, comprising administering to a subject with acute decompensated heart failure a pharmaceutically active H2 relaxin in an amount effective to reduce diuretic use during a hospital stay compared to treatment of acute decompensated heart failure without using H2 relaxin. In some embodiments, the H2 relaxin is administered at an infusion rate in the range of about 10 μg/kg/day to about 100 μg/kg/day. In some embodiments, the loop diuretic use during the hospital stay is reduced compared to treatment of acute decompensated heart failure without H2 relaxin. In another embodiment, the loop diuretic use is reduced by at least 10% over a 14-day period compared to treatment without H2 relaxin. In yet another embodiment, the loop diuretic use is reduced by at least 20% over a 14-day period compared to treatment without H2 relaxin. In yet another embodiment, the loop diuretic use is reduced by at least 30% over a 14-day period compared to treatment without H2 relaxin. In some embodiments, the subject has a left ventricular ejection fraction of at least 40%. In some embodiments, the subject is normotensive or hypertensive. In another embodiment, the subject has a systolic blood pressure of at least about 125 mm Hg. In another embodiment, the subject is renally impaired. In yet another embodiment, the subject has a creatinine clearance in the range of about 35 to about 75 mL/min. In some embodiments, the H2 relaxin is administered for at least 24 or 48 hours. In another embodiment, the H2 relaxin is administered over 48 hours. In yet another embodiment, the H2 relaxin is administered at an infusion rate in the range of about 10 μg/kg/day to about 960 μg/kg/day. In yet another embodiment, the H2 relaxin is administered at an intravenous infusion rate in the range of about 10 μg/kg/day to about 250 μg/kg/day. In yet another embodiment, the H2 relaxin is administered at an intravenous infusion rate in the range of about 30 μg/kg/day to about 100 μg/kg/day. In yet another embodiment, the H2 relaxin is administered at an intravenous infusion rate in the range of about 30 μg/kg/day. In some embodiments, the method further comprises reducing the 60-day risk of death or rehospitalization of the subject compared to treatment of acute decompensated heart failure without H2 relaxin. In some embodiments, the 60-day risk of death or rehospitalization is reduced by at least 50%. In some embodiments, the subject has dyspnea requiring hospitalization. In some embodiments, the method further comprises reducing the hospitalization length of stay by at least one day compared to treatment of acute decompensated heart failure without H2 relaxin. In some embodiments, the H2 relaxin is administered at an intravenous infusion rate in the range of about 30 μg/kg/day and the hospitalization length of stay is reduced by at least two days compared to treatment of acute decompensated heart failure without H2 relaxin. In some embodiments, the method further comprises reducing the 60-day risk of rehospitalization due to heart failure or renal insufficiency of the subject compared to treatment of acute decompensated heart failure without H2 relaxin. In some embodiments, the 60-day risk of rehospitalization due to heart failure or renal insufficiency is reduced by at least about 50%. In another embodiment, the H2 relaxin is administered at an intravenous infusion rate in the range of about 30 μg/kg/day and the 60-day risk of rehospitalization due to heart failure or renal insufficiency is reduced by at least about 70%. In some embodiments, the method further comprises reducing the 180-day risk of cardiovascular death of the subject compared to treatment of acute decompensated heart failure without H2 relaxin. In some embodiments, the 180-day risk of cardiovascular death is reduced by at least about 50%. In another embodiment, the H2 relaxin is administered at an intravenous infusion rate less than about 250 μg/kg/day and the 180-day risk of cardiovascular death is reduced by at least about 70%. In some embodiments, the method further comprises reducing the 180-day risk of all-cause mortality of the subject compared to treatment of acute decompensated heart failure without H2 relaxin. In some embodiments, the 180-day risk of all-cause mortality is reduced by at least about 25%. In another embodiment, the H2 relaxin is administered at an intravenous infusion rate less than about 250 μg/kg/day and the 180-day risk of all-cause mortality is reduced by at least about 50%. In some preferred embodiments, the subject is a male or a nonpregnant female. In some preferred embodiments, the subject has a systolic blood pressure of at least about 125 mmHg. Moreover the disclosure provides a method for treating acute decompensated heart failure, comprising administering to a human subject with acute decompensated heart failure a pharmaceutically active H2 relaxin in an amount effective to reduce the 60-day risk of death or rehospitalization of the subject compared to treatment of acute decompensated heart failure without H2 relaxin. In some embodiments, the subject has at least one acute heart failure sign or symptom selected from the group consisting of dyspnea at rest, orthopnea, dyspnea on exertion, edema, rales, pulmonary congestion, jugular venous pulse or distension, edema associated weight gain, high pulmonary capillary wedge pressure, high left ventricular end-diastolic pressure, high systemic vascular resistance, low cardiac output, low left ventricular ejection fraction, need for intravenous diuretic therapy, need for additional intravenous vasodilator therapy, and incidence of worsening in-hospital heart failure. In another embodiment, the subject has a left ventricular ejection fraction of at least 20% or at least 40%. In another embodiment, the subject is normotensive or hypertensive. In yet another embodiment, the subject has a systolic blood pressure of at least about 125 mm Hg. In some embodiments, the subject is renally impaired. In another embodiment, the subject has a creatinine clearance in the range of about 35 to about 75 ml/min. In some embodiments of the method, the H2 relaxin is administered for at least 24 hours. In another embodiment, the H2 relaxin is administered over 48 hours. In another embodiment, the H2 relaxin is administered at an infusion rate in the range of about 10 μg/kg/day to about 960 μg/kg/day. In yet another embodiment, the H2 relaxin is administered at an intravenous infusion rate in the range of about 10 µg/kg/day to about 250 µg/kg/day. In yet another embodiment, the H2 relaxin is administered at an intravenous infusion rate in the range of about 30 µg/kg/day to about 100 µg/kg/day. In yet another embodiment, the H2 relaxin is administered at an intravenous infusion rate in the range of about 30 µg/kg/day. In some embodiments, the 60-day risk of death or rehospitalization is reduced by at least 50%. In some embodiments, the subject has dyspnea requiring hospitalization. In some embodiments, the method further comprises reducing the hospitalization length of stay by at least one day compared to treatment of acute decompensated heart failure without H2 relaxin. In another embodiment, the H2 relaxin is administered at an intravenous infusion rate in the range of about 30 µg/kg/day and the hospitalization length of stay is reduced by at least two days compared to treatment of acute decompensated heart failure without H2 relaxin. In some embodiments, the method further comprises reducing the 60-day risk of rehospitalization due to heart failure or renal insufficiency of the subject compared to treatment of acute decompensated heart failure without H2 relaxin. In another embodiment, the 60-day risk of rehospitalization due to heart failure or renal insufficiency is reduced by at least about 50%. In another embodiment, the H2 relaxin is administered at an intravenous infusion rate in the range of about 30 µg/kg/day and the 60-day risk of rehospitalization due to heart failure or renal insufficiency is reduced by at least about 70%. In some embodiments, the method further comprises reducing the 180-day risk of cardiovascular death of the subject compared to treatment of acute decompensated heart failure without H2 relaxin. In some embodiments, the 180-day risk of cardiovascular death is reduced by at least about 50%. In another embodiment, the H2 relaxin is administered at an intravenous infusion rate less than about 250 µg/kg/day and the 180-day risk of cardiovascular death is reduced by at least about 70%. In some embodiments, the method further comprises reducing the 180-day risk of all-cause mortality of the subject compared to treatment of acute decompensated heart failure without H2 relaxin. In another embodiment, the 180-day risk of all-cause mortality is reduced by at least about 25%. In another embodiment, the H2 relaxin is administered at an intravenous infusion rate less than about 250 µg/kg/day and the 180-day risk of all-cause mortality is reduced by at least about 50%. In some preferred embodiments, the subject is a male or a nonpregnant female.

BRIEF DESCRIPTION OF THE DRAWINGS

The present disclosure is best understood when read in conjunction with the accompanying figures, which serve to illustrate the preferred embodiments. It is understood, however, that the disclosure is not limited to the specific embodiments disclosed in the figures.

DETAILED DESCRIPTION

General Overview

The present disclosure relates to methods of reducing decompensation in populations of subjects that are specifically prone to symptoms and events of acute decompensated heart failure (AHF) such as dyspnea and fluid retention. Since AHF is the most common reason why patients over 65 years of age are admitted to the hospital, it is associated with staggering costs to the health care system. The prognosis for patients that are admitted with AHF or symptoms thereof has so far been dismal as it is associated with high readmission and mortality rates within six months of admission. As disclosed herein, when patients who have previously been diagnosed with AHF and/or acute vascular failure or exhibit symptoms that are typical of AHF and/or acute vascular failure are treated with relaxin, their condition improves markedly and stabilizes over a short period of time. More specifically, when relaxin is administered to subjects who suffer from acute decompensation associated with AHF, significant cardiovascular and renal improvements are seen in these subjects. For example, when patients were administered relaxin for as little as 48 hours the improvements lasted over a period of 14 days. The improvements included significant reductions in acute cardiac decompensation events including a noticeable reduction in dyspnea (shortness of breath), a reduction in excessive body weight due to fluid retention (e.g., patients lost on the average about 1 kg of body weight), shorter hospital stays (e.g., by as much as 2.5 days), a decreased likelihood of hospital re-admissions, a lower need for loop diuretics, a lower need for intravenous nitroglycerin and a decreased incidence of worsening heart failure. These changes significantly improved patient well-being and have strong future implications on pharmacoeconomics including reductions in cost of care.

Figure 3:
FIG. 3 is an illustration of the lumen of a blood vessel. Arrows show the smooth muscle cells (SM) and the endothelium (E). Relaxin receptors are located on the smooth muscle cells of the blood vessels (systemic and renal vasculature).

Without wanting to be bound by theory, relaxin is contemplated to act through specific receptors that are found on smooth muscle cells that make up the vasculature (FIG. 3). As such, relaxin is a specific, moderate, systemic and renal vasodilator that improves heart and renal function via specific and balanced vasodilation. Since AHF is a cardio-renal disease, relaxin benefits patients afflicted with AHF and/or acute vascular failure and/or symptoms thereof.

Definitions

Figure 1:
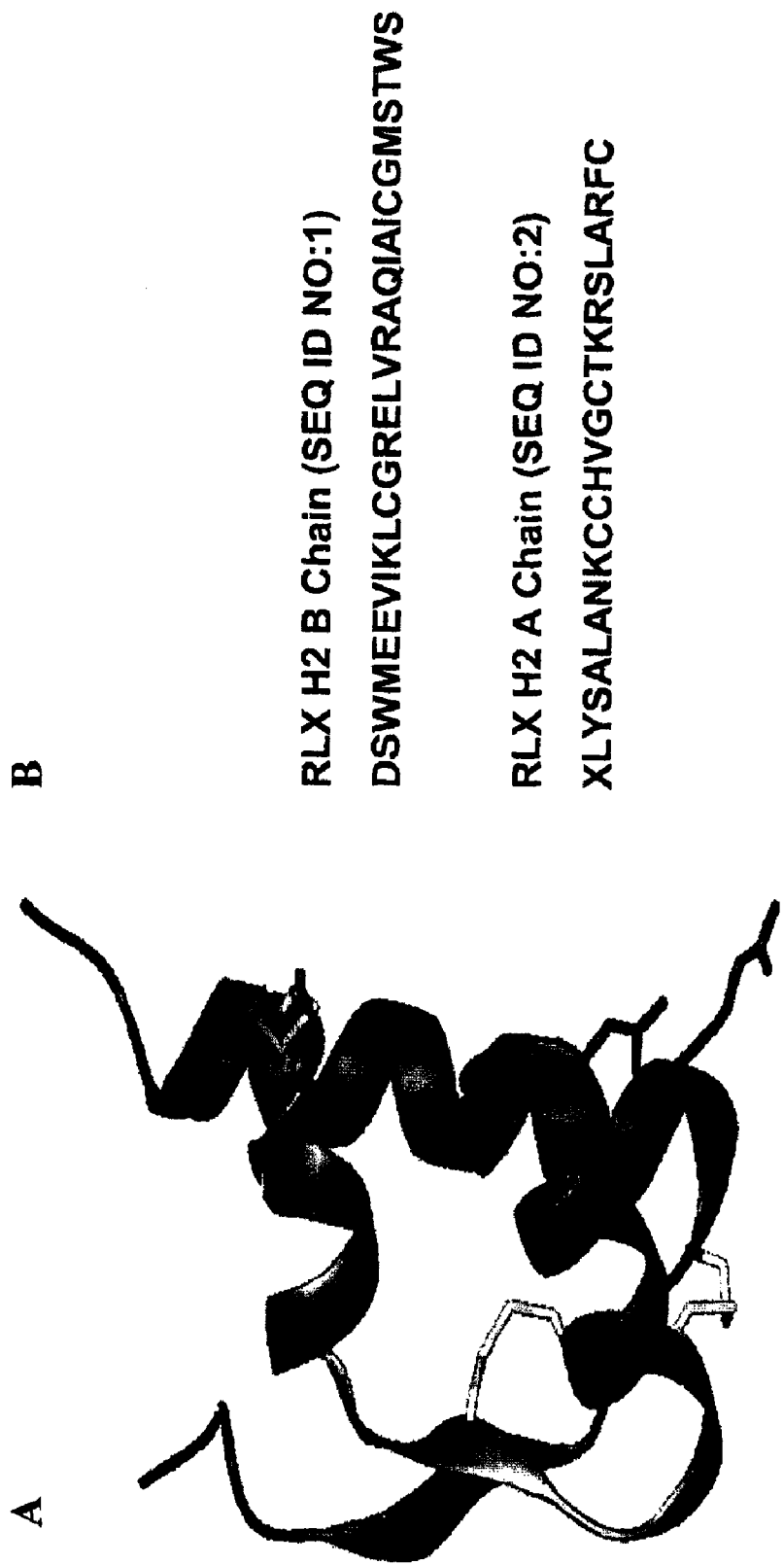
FIG. 1A depicts the peptide hormone H2 relaxin which is similar in size and shape to insulin.
FIG. 1B provides the amino acid sequence of the B chain (SEQ ID NO:1) and the A chain (SEQ ID NO:2 with X representing glutamic acid [E] or glutamine [Q]) of human relaxin 2 (H2).

The term "relaxin" refers to a peptide hormone which is well known in the art (see FIG. 1). The term "relaxin", as used herein, encompasses human relaxin, including intact full length human relaxin or a portion of the relaxin molecule that retains biological activity. The term "relaxin" encompasses human H1 preprorelaxin, prorelaxin, and relaxin; H2 preprorelaxin, prorelaxin, and relaxin; and H3 preprorelaxin, prorelaxin, and relaxin. The term "relaxin" further includes biologically active (also referred to herein as "pharmaceutically active") relaxin from recombinant, synthetic or native sources as well as relaxin variants, such as amino acid sequence variants. As such, the term contemplates synthetic human relaxin and recombinant human relaxin, including synthetic H1, H2 and H3 human relaxin and recombinant H1, H2 and H3 human relaxin. The term further encompasses active agents with relaxin-like activity, such as relaxin agonists and/or relaxin analogs and portions thereof that retain biological activity, including all agents that competitively displace bound relaxin from a relaxin receptor (e.g., LGR7 receptor, LGR8 receptor, GPCR135, GPCR142, etc.). Thus, a pharmaceutically effective relaxin agonist is any agent with relaxin-like activity that is capable of binding to a relaxin receptor to elicit a relaxin-like response. In addition, the nucleic acid sequence of human relaxin as used herein must not be 100% identical to nucleic acid sequence of human relaxin (e.g., H1, H2 and/or H3) but may be at least about 40%, 50%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the nucleic acid sequence of human relaxin. Relaxin, as used herein, can be made by any method known to those skilled in the art. Examples of such methods are illustrated, for example, in U.S. Pat. No. 5,759,807 as well as in Büllesbach et al. (1991) *The Journal of Biological Chemistry* 266(17):10754-10761.

Examples of relaxin molecules and analogs are illustrated, for example, in U.S. Pat. No. 5,166,191. Naturally occurring biologically active relaxin may be derived from human, murine (i.e., rat or mouse), porcine, or other mammalian sources. Also encompassed is relaxin modified to increase in vivo half life, e.g., PEGylated relaxin (i.e., relaxin conjugated to a polyethylene glycol), modifications of amino acids in relaxin that are subject to cleavage by degrading enzymes, and the like. The term also encompasses relaxin comprising A and B chains having N- and/or C-terminal truncations. In general, in H2 relaxin, the A chain can be varied from A(1-24) to A(10-24) and B chain from B(1-33) to B(10-22); and in H1 relaxin, the A chain can be varied from A(1-24) to A(10-24) and B chain from B(1-32) to B(10-22). Also included within the scope of the term "relaxin" are other insertions, substitutions, or deletions of one or more amino acid residues, glycosylation variants, unglycosylated relaxin, organic and inorganic salts, covalently modified derivatives of relaxin, preprorelaxin, and prorelaxin. Also encompassed in the term is a relaxin analog having an amino acid sequence which differs from a wild-type (e.g., naturally-occurring) sequence, including, but not limited to, relaxin analogs disclosed in U.S. Pat. No. 5,811,395. Possible modifications to relaxin amino acid residues include the acetylation, formylation or similar protection of free amino groups, including the N-terminal, amidation of C-terminal groups, or the formation of esters of hydroxyl or carboxylic groups, e.g., modification of the tryptophan (Trp) residue at B2 by addition of a formyl group. The formyl group is a typical example of a readily-removable protecting group. Other possible modifications include replacement of one or more of the natural amino-acids in the B and/or A chains with a different amino acid (including the D-form of a natural amino-acid), including, but not limited to, replacement of the Met moiety at B24 with norleucine (Nle), valine (Val), alanine (Ala), glycine (Gly), serine (Ser), or homoserine (HomoSer). Other possible modifications include the deletion of a natural amino acid from the chain or the addition of one or more extra amino acids to the chain. Additional modifications include amino acid substitutions at the B/C and C/A junctions of prorelaxin, which modifications facilitate cleavage of the C chain from prorelaxin; and variant relaxin comprising a non-naturally occurring C peptide, e.g., as described in U.S. Pat. No. 5,759,807. Also encompassed by the term "relaxin" are fusion polypeptides comprising relaxin and a heterologous polypeptide. A heterologous polypeptide (e.g., a non-relaxin polypeptide) fusion partner may be C-terminal or N-terminal to the relaxin portion of the fusion protein. Heterologous polypeptides include immunologically detectable polypeptides (e.g., "epitope tags"); polypeptides capable of generating a detectable signal (e.g., green fluorescent protein, enzymes such as alkaline phosphatase, and others known in the art); therapeutic polypeptides, including, but not limited to, cytokines, chemokines, and growth factors. All such variations or alterations in the structure of the relaxin molecule resulting in variants are included within the scope of this disclosure so long as the functional (biological) activity of the relaxin is maintained. Preferably, any modification of relaxin amino acid sequence or structure is one that does not increase its immunogenicity in the individual being treated with the relaxin variant. Those variants of relaxin having the described functional activity can be readily identified using in vitro and in vivo assays known in the art.

The term "heart failure" generally means that the heart is not working as efficiently as it should. Heart failure occurs when the heart muscle cannot keep up with the needs the body has for blood flow. It is a syndrome, i.e., a collection of findings which may arise from a number of causes. Heart failure can be caused by weakening of the heart muscle (i.e., cardiomyopathy), leaving it unable to pump enough blood. Heart failure is also termed congestive heart failure (CHF) because fluids typically build up in the body, which is then said to be congested. In addition to heart failure caused from a weakened heart, there are also other varieties of heart failure. These are CHF due to the body having needs which are too high for even a normal heart to keep up with, for example, in some cases of thyroid disease in which too much thyroid hormone is produced, in patients with anemia, or several other conditions; and CHF due to neurohormonal imbalances that eventually leads to acute episodes of dyspnea or other acute events such as hypertension, high blood pressure, arrhythmia, reduced renal blood flow, renal insufficiency and in severe cases mortality, shifting the patient from compensated CHF to acute decompensated heart failure (AHF) and/or acute vascular failure.

The terms "acute cardiac decompensation" and "acute decompensation" are used interchangeably herein, and mean for the purpose of the specification and claims, an inability of the heart muscle to compensate for systemic and renal vasoconstriction due to neurohormonal imbalances in the body. Acute cardiac decompensation is characterized by altered cardiac function and fluid regulation, leading to the onset of hemodynamic instability and physiologic changes (particularly congestion and edema), and heart failure symptoms (most commonly dyspnea). This form of functional decompensation could be misdiagnosed as being caused by a valvular or myocardial defect (i.e., a structural defect) although it is not usually associated with hypotension. However, "acute cardiac decompensation" as used herein, is a functional decompensation that is often associated with any one or more of certain decompensation events, including but not limited to, dyspnea, hypertension, high blood pressure, arrhythmia, reduced renal blood flow, renal insufficiency and mortality. Patients presenting with "acute cardiac decompensation", as used herein, typically have, but may not have previously been diagnosed with chronic heart failure (CHF). Such patients may have a history of heart disease or the complete absence thereof.

"Administering" refers to giving or applying to a subject a pharmaceutical remedy or formulation via a specific route, including but not limited to, intravenously, subcutaneously, intramuscularly, sublingually and via inhalation.

The term "vasculature" refers to the network of blood vessels in an organ or body part, including arteries and capillaries.

The term "balanced vasodilation" means, for purpose of the specification and claims, a dual vasodilation that occurs in the systemic (mostly arterial) and renal vasculature as a result of the binding of relaxin or a relaxin agonist to specific relaxin receptors.

The terms "neurohormonal imbalance" and "neurohumoral imbalance" are used interchangeably herein, and refer to a hormonal disturbance in the body that can lead to heart failure. For example, excessive signaling through Gs-coupled adrenergic or Gq-coupled angiotensin pathways can cause neurohormonal imbalances. In both cases, excessive neurohormonal signaling can cause, as well as accelerate, functional decompensation (see Schrier et al., supra). In addition, excessive neurohormonal signaling can cause, as well as accelerate, acute vascular failure.

The term "fluid overload", as used herein, refers to a condition that occurs when the blood contains too much water. Fluid overload (hypervolemia) is commonly seen with heart failure that can cause fluid overload by activation of the renin-angiotensin-aldosterone system. This fluid, primarily salt and water, builds up in various locations in the body and leads to an increase in weight, swelling in the legs and arms (peripheral edema), and/or in the abdomen (ascites). Eventually, the fluid enters the air spaces in the lungs, reduces the amount of oxygen that can enter the blood, and causes shortness of breath (dyspnea). Fluid can also collect in the lungs when lying down at night and can make night time breathing and sleeping difficult (paroxysmal nocturnal dyspnea). Fluid overload is one of the most prominent features of AHF and/or acute vascular failure.

The term "cardiac arrhythmia" means a condition where the muscle contraction of the heart becomes irregular. An unusually fast rhythm (more than 100 beats per minute) is called tachycardia. An unusually slow rhythm (fewer than 60 beats per minute) is called bradycardia.

"Cardiac ischemia" occurs when blood flow to the heart muscle (myocardium) is obstructed by a partial or complete blockage of a coronary artery. A sudden, severe blockage may lead to a heart attack (myocardial infarction). Cardiac ischemia may also cause a serious abnormal heart rhythm (arrhythmia), which can cause fainting and in severe cases death.

The term "pathophysiological" refers to a disturbance of any normal mechanical, physical, or biochemical function, either caused by a disease, or resulting from a disease or abnormal syndrome or condition that may not qualify to be called a disease. "Pathophysiology" is the study of the biological and physical manifestations of disease as they correlate with the underlying abnormalities and physiological disturbances.

Figure 2:
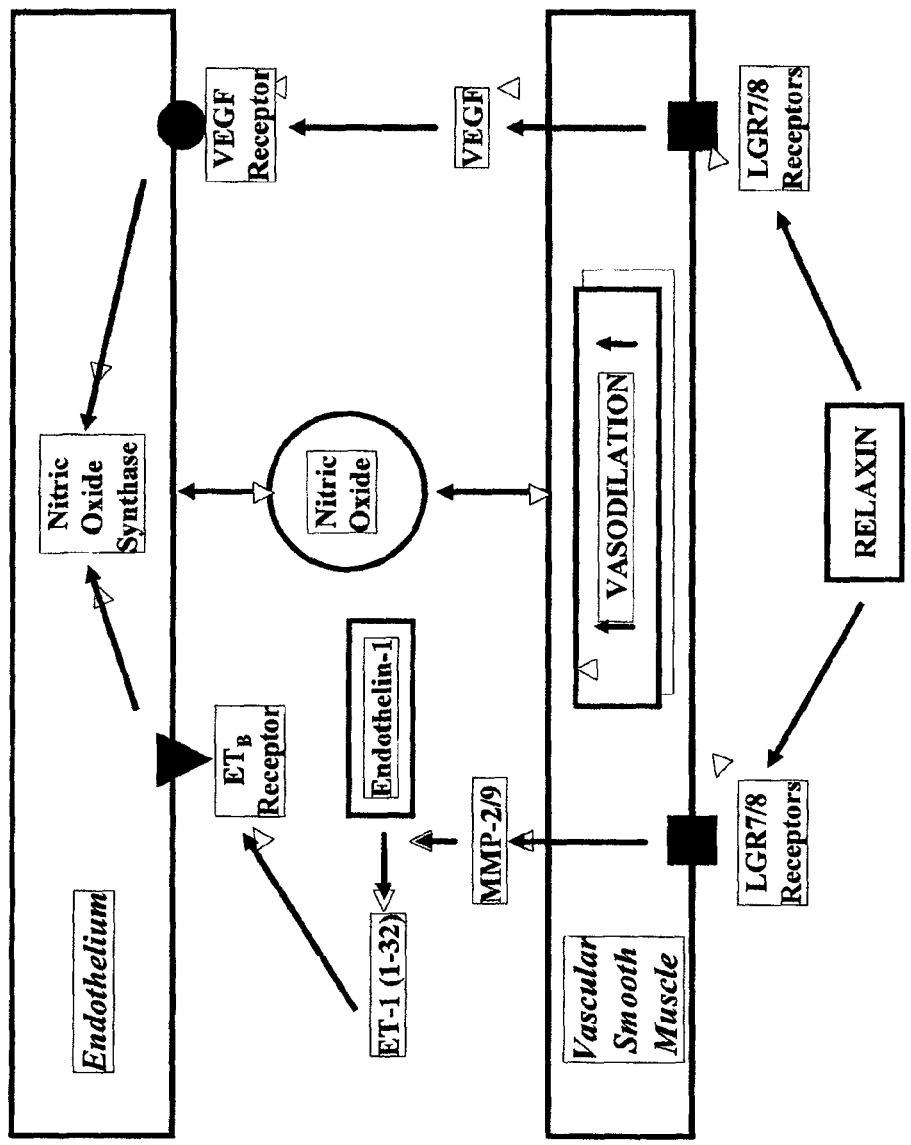
FIG. 2 is an illustration of a possible mechanism of action for relaxin. Relaxin receptors LGR7 and LGR8 bind relaxin which activates matrix metalloproteinases MMP-2 and MMP-9 to convert endothelin-1 to truncated endothelin-1 (1-32) which in turn binds to the endothelin B receptor ($ET_B$ receptor). This triggers nitric oxide synthase (NOS) to produce nitric oxide (NO) which increases vasodilation.

The term "nitric oxide" and "NO" are used interchangeably herein and refer to an important signaling molecule involved in many physiological and pathological processes within the mammalian body, including in humans. NO can act as a vasodilator that relaxes the smooth muscle in blood vessels, which causes them to dilate. Dilation of arterial blood vessels (mainly arterioles) leads to a decrease in blood pressure. Relaxin is believed to elicit at least some vasodilation through NO. As such, relaxin binds to specific relaxin receptors such as LGR7 and LGR8 receptors on smooth muscle cells of the vasculature which in turn activates the endothelin cascade to activate nitric oxide synthase (NOS) to produce NO (FIG. 2).

The terms "AHF," "acute heart failure" and "acute decompensated heart failure" as used herein is defined by the presence of all of the following at screening: dyspnea at rest or with minimal exertion, pulmonary congestion on chest X-ray and elevated natriuretic peptide levels [brain natriuretic peptide (BNP)≧350 pg/mL or NT-pro-BNP≧1400 pg/mL].

The term "dyspnea" refers to difficult or labored breathing. It is a sign of a variety of disorders and is primarily an indication of inadequate ventilation or of insufficient amounts of oxygen in the circulating blood. The term "orthopnea" refers to difficult or labored breathing when lying flat, which is relieved when in an upright position (sitting or standing as opposed to reclining).

Clinical studies and practice guidelines typically define hypertension as a systolic blood pressure (SBP) greater than about 140 mm Hg, and normal blood pressure as a SBP below about 140 mm Hg, 130 mm Hg or 120 mm Hg, depending upon the particular study or guideline. In the context of acute heart failure or other cardiac disease, hypotension may be characterized as a SBP below about 110 mm Hg, 100 mm Hg, or 90 mm Hg. In some preferred embodiments, the phrase a "normotensive or hypertensive state" refers to a SBP of greater than 125 mmHg at the time of study screening or relaxin administration.

As used herein, the phrase "impaired renal function" is defined as an estimated glomerular filtration rate (eGFR) of between 30 to 75 mL/min/1.73 m2, calculated using the simplified Modification of Diet in Renal Disease (sMDRD) equation.

The term "placebo" refers to a physiologically inert treatment that is often compared in clinical research trials to a physiologically active treatment. These trials are usually carried out as double blind studies and neither the prescribing doctor nor the patients know if they are taking the active drug or the substance without any apparent pharmaceutical effect (placebo). It has been observed that a patient receiving a physiologically inert treatment can demonstrate improvement for his or her condition if he or she believes they are receiving the physiologically active treatment (placebo effect). Therefore, the inclusion of a placebo in a trial assures that the statistically significant beneficial effect is related to the physiologically active treatment and not simply a result of a placebo effect.

The definition of "rehospitalization" is a hospital readmission during a certain time period after initial treatment. The time period is generally dependent on the kind of treatment and the condition of the patient.

As used herein the term "cardiovascular death" refers to death that is primarily due to a cardiovascular cause, such as death due to stroke, acute myocardial infarction, refractory congestive heart failure and any sudden.

A "loop diuretic" means a drug used in patients with congestive heart failure or renal insufficiency to reduce symptoms of hypertension and edema. A loop diuretic belongs to a class of diuretic agents that reduces readsorption of sodium and chloride by the kidney leading to an increased secretion of urine.

The term "about" when used in the context of a stated value, encompasses a range of up to 10% above or below the stated value (e.g., 90-110% of the stated value). For instance, an intravenous (IV) infusion rate of about 30 mcg/kg/day, encompasses IV infusion rates of 27 mcg/kg/day to 33 mcg/kg/day.

"Therapeutically effective" refers to the amount of pharmaceutically active relaxin that will result in a measurable desired medical or clinical benefit to a patient, as compared to the patient's baseline status or to the status of an untreated or placebo-treated (e.g., not treated with relaxin) subject.

Relaxin

Relaxin is a polypeptide hormone that is similar in size and shape to insulin (FIG. 1). More specifically, relaxin is an endocrine and autocrine/paracrine hormone belonging to the insulin gene superfamily. The active form of the encoded protein consists of an A chain and a B chain, held together by disulphide bonds, two inter-chains and one intra-chain. Thus, the structure closely resembles insulin in the disposition of disulphide bonds. In humans, there are three known non-allelic relaxin genes, relaxin-1 (RLN-1 or H1), relaxin-2 (RLN-2 or H2) and relaxin-3 (RLN-3 or H3). H1 and H2 share high sequence homology. There are two alternatively spliced transcript variants encoding different isoforms described for this gene. H1 and H2 are differentially expressed in reproductive organs (U.S. Pat. No. 5,023,321 and Garibay-Tupas et al., *Molecular and Cellular Endocrinology* 219:115-125, 2004), while H3 is found primarily in the brain. The evolution of the relaxin peptide family in its receptors is generally well known in the art (Wilkinson et al., *BMC Evolutionary Biology* 5(14):1-17, 2005; and Wilkinson and Bathgate, Chapter 1, Relaxin and Related Peptides, *Landes Bioscience and Springer Science+Business Media*, 2007).

Relaxin activates specific relaxin receptors, i.e., LGR7 (RXFP1) and LGR8 (RXFP2) as well as GPCR135 and GPCR142. LGR7 and LGR8 are leucine-rich repeat-containing, G protein-coupled receptors (LGRs) which represent a unique subgroup of G protein-coupled receptors. They contain a heptahelical transmembrane domain and a large glycosylated ectodomain, distantly related to the receptors for the glycoproteohormones, such as the LH-receptor or FSH-receptor. These relaxin receptors are found in the heart, smooth muscle, connective tissue, and central and autonomous nervous system. Potent relaxins such as H1, H2, porcine and whale relaxin possess a certain sequence in common, i.e., the Arg-Glu-Leu-Val-Arg-X-X-Ile sequence (SEQ ID NO:3) or binding cassette. These relaxins activate the LGR7 and LGR8 receptors. Relaxins that deviate from this sequence homology such as rat, shark, dog and horse relaxins show a reduction in bioactivity through the LGR7 and LGR8 receptors (see Bathgate et al. (2005) *Ann. N.Y. Acad Sci.* 1041:61-76; *Receptors for Relaxin Family Peptides*). However, similar to H2 relaxin, H3 relaxin activates the LGR7 receptor (see Satoko et al. (2003) *The Journal of Biological Chemistry* 278(10):7855-7862). In addition, H3 has been shown to activate the GPCR135 receptor (see Van der Westhuizen (2005) *Ann. N.Y. Acad. Sci.* 1041:332-337) and GPCR142 receptor. GPCR135 and GPCR142 are two structurally related G-protein-coupled receptors. Mouse and rat GPCR135 exhibit high homology (i.e., greater than 85%) to the human GPCR135 and have very similar pharmacological properties to that of the human GPCR135. Human and mouse as well as rat relaxin-3 binds to and activates mouse, rat, and human GPCR135 at high affinity. In contrast, the mouse GPCR142 is less well conserved (i.e., 74% homology) with human GPCR142. GPCR142 genes from monkey, cow, and pig were cloned and shown to be highly homologous (i.e., greater than 84%) to human GPCR142. Pharmacological characterization of GPCR142 from different species has shown that relaxin-3 binds to GPCR142 from different species at high affinity (see Chen et al. (2005) *The Journal of Pharmacology and Experimental Therapeutics* 312(1):83-95).

Relaxin is found in both, women and men (see Tregear et al.; *Relaxin* 2000, *Proceedings of the Third International Conference on Relaxin & Related Peptides* (22-27 Oct. 2000, Broome, Australia). In women, relaxin is produced by the corpus luteum of the ovary, the breast and, during pregnancy, also by the placenta, chorion, and decidua. In men, relaxin is produced in the testes. Relaxin levels rise after ovulation as a result of its production by the corpus luteum and its peak is reached during the first trimester, not toward the end of pregnancy. In the absence of pregnancy its level declines. In humans, relaxin is plays a role in pregnancy, in enhancing sperm motility, regulating blood pressure, controlling heart rate and releasing oxytocin and vasopressin. In animals, relaxin widens the pubic bone, facilitates labor, softens the cervix (cervical ripening), and relaxes the uterine musculature. In animals, relaxin also affects collagen metabolism, inhibiting collagen synthesis and enhancing its breakdown by increasing matrix metalloproteinases. It also enhances angiogenesis and is a renal vasodilator.

Relaxin has the general properties of a growth factor and is capable of altering the nature of connective tissue and influencing smooth muscle contraction. H1 and H2 are believed to be primarily expressed in reproductive tissue while H3 is known to be primarily expressed in brain (supra). As disclosed herein, H2 plays a major role in cardiovascular and cardiorenal function and can thus be used to treat associated diseases. H1 and H3 due to their homology with H2 are contemplated to be suitable for treating cardiovascular disease. In addition, pharmaceutically effective relaxin agonists with relaxin-like activity would be capable of activating relaxin receptors and to elicit a relaxin-like response.

Acute Heart Failure (AHF) Patients

AHF is the most common cause for hospital admission in patients older than 65 years and for congestive heart failure-related morbidity (Cotter et al., *American Heart Journal* 155 (1):9-18, 2008). In spite of the progress made in mortality-reducing drug therapies for chronic (systolic) heart failure, including angiotensin-converting enzyme inhibitors, angiotensin II receptor blockers, β-blockers, and aldosterone antagonists, no comparable progress has been made in the art for AHF, where both therapy and mortality have not changed significantly over the past 30 years (Allen et al., *CMAJ* 176: 797-805, 2007). The classic AHF drugs such as loop diuretics, nitroglycerin/nitroprusside, dobutamine, or milrinone have not been able to improve AHF outcome (Allen et al., supra). The same is true for therapeutic strategies including endothelin-1 receptor blockade with TEZOSENTAN, vasopressin V2 receptor antagonism using TOLVAPTAN, the natriuretic peptide NESIRITIDE, and LEVOSIMENDAN which combines calcium-sensitizing and vasodilatory properties. Chronic renal dysfunction is frequently a part of the complex morbidity of AHF, particularly in older AHF patients. Deterioration of renal function can induce or worsen AHF (i.e., cardiorenal syndrome) and is related to significant morbidity in the AHF population. According to the ADHERE registry (Heywood, *Heart Fail. Rev.* 9:195-201, 2004), impairment of renal function correlates with a worse prognosis for AHF. Hence, treatment with relaxin provides a novel AHF therapy with favorable renal effects, which significantly improves the prognosis for patients that are part of the AHF population. In accordance, pharmaceutically active relaxin can be used to treat these AHF patients, or subjects afflicted with acute cardiac decompensation events or symptoms, or subjects afflicted with acute cardiac decompensation that is associated with AHF.

Patients with AHF can be classified into three groups based on their systolic blood pressure at the time of presentation (See, e.g., Gheorghiade et al., JAMA, 296: 2217-2226, 2006; and Shin et al., Am J Cardiol, 99[suppl]:4A-23A. 2007). The three groups include: 1) the hypotensive group (low blood pressure); 2) the normotensive group (normal blood pressure) and 3) the hypertensive group (high blood pressure).

Hypotensive AHF patients having a very low left ventricle ejection fraction (LVEF) are described as having "low cardiac output" or "cardiogenic shock." Such hypotensive AHF patients have hearts that fail to adequately pump blood, meaning that the percentage of the blood in the ventricle that is pumped out with each contraction is reduced.

Normotensive AHF patients have higher blood pressure and typically a greater LVEF than hypotensive AHF patients and are sometimes described as having "cardiac failure." The cause of AHF in these patients is a combination of both depressed cardiac function and vasoconstriction.

Hypertensive AHF patients have higher blood pressure and typically a greater LVEF than normotensive AHF patients and are generally described as having "vascular failure." Even though these patients have some degree of abnormal cardiac function, the predominant cause of their AHF is vasoconstriction.

Current data indicates that vascular failure and cardiac failure may be the most common types of AHF, as opposed to low cardiac output (ADHERE Scientific Advisory Committee, Acute Decompensated Heart Failure National Registry (ADHERE) Core Module Q1 2006 Final Cumulative National Benchmark Report, Scios, Inc. pp. 1-19, 2006).

Many patients presenting with acute heart failure signs and symptoms, including pulmonary congestion on x-ray, difficulty breathing (dyspnea) and normal (normotensive) or high (hypertensive) blood pressure have preserved left ventricular function (generally >40% EF). These acute heart failure patients exhibit problems with excessive vasoconstriction and with filling the ventricle with blood, rather than the ability of the ventricle to pump blood. These patients are clearly distinguishable from hypotensive AHF patients.

Traditional treatment of low cardiac output or cardiogenic shock (hypotensive AHF) involve pharmacologic agents that cause the heart to contract harder (inotropic) and/or faster (chronotropic) to maintain the perfusion of vital organs (See, e.g., Nieminen et al., *Eur Heart J*, 26:384-416, 2005; and Shin et al., *Am J Cardiol*, 99[suppl]:4A-23A. 2007). However, normotensive (vascular failure) and hypertensive (cardiac failure) HF patients are extremely sensitive to changes in heart rate since an increase in heart rate reduces the filling time between vascular contractions, and hence lowers the volume of blood filling the ventricle (Satpathy et al., *American Family Physician*, 73:841-846, 2006). For this reason, treatments for acute heart failure that increase heart rate would be detrimental to hypertensive acute heart failure patients, if not contraindicated (Satpathy et al., supra).

Generally, pharmaceutically effective relaxin or a pharmaceutically effective relaxin agonist should be administered at a constant rate to provide safe relief and achieve a steady state in the patient. For example, it is preferred to administer relaxin intravenously to maintain a serum concentration of relaxin of from about 1 to 500 ng/ml. More specifically, the administration of relaxin is continued as to maintain a serum concentration of relaxin of from about 0.5 to about 500 ng/ml, more preferably from about 0.5 to about 300 ng/ml, and most preferably from about 3 to about 75 ng/ml. The subject would be treated with relaxin at about 10 to 1000 μg/kg of subject body weight per day rather than via a loading dose such as a bolus. More preferably, the subject would be treated with relaxin at about 10 to about 250 μg/kg of subject body weight per day. In another preferred embodiment, pharmaceutically effective relaxin or an agonist thereof is administered at about 30 μg/kg/day. Other forms of administering relaxin are also contemplated by the disclosure including, but not limited to, subcutaneously, intramuscularly, sublingually and via inhalation. Notably, acute situations are normally treated with a loading dose (bolus) because the patient is "acute" and needs instant relief. However, this can lead to situation where the patient is overcompensated, thus, leading to worsening of heart failure symptoms or even death. As described herein, administering relaxin at a constant rate in acute situations is a safe and effective form of administration.

Relaxin Treatment Results in Balanced Vasodilation

Without wanting to be bound by theory, the beneficial effect of relaxin is believed to be a direct result of relaxin acting as a receptor-specific vasodilator in the renal and systemic vasculature by binding to specific relaxin receptors that are found on the smooth muscle tissue of the vasculature. This in turn results in balanced vasodilation as both systemic and renal arteries are vasodilated in a moderate but effective way without causing hypotension in the treated patient. This property of relaxin as a receptor-specific and balancing vasodilator is particularly advantageous in context in which it is desirable to obtain increased vasodilation in specific areas of the body where vasoconstriction causes a serious ill effect such as in the arteries that supply blood to the heart and the kidneys. Notably, the balanced vasodilation occurs without causing any deleterious side effect during the process of treatment. A common problem with treatment with non-specific vasodilators is that these drugs often lead to serious side effects in the treated patients, mainly because general agonists act too potently and non-specifically. In comparison, the moderate effect of relaxin slowly increases vasodilation in areas of the body where it is needed the most. It is important to note that relaxin treatment does not cause hypotension as is the case with many drugs that overcompensate for vasoconstriction. In particular, non-specific vasodilators can cause large and small arteries and veins throughout the body to dilate excessively, causing hypotension. Thus, when the patient receives a pharmaceutical composition with pharmaceutically active relaxin or pharmaceutically effective relaxin agonist which targets systemic and renal blood vessels via localized specific relaxin receptors (e.g., LRG7, LGR8, GPCR135, GPCR142 receptors) the result is balanced vasodilation without hypotension.

Consequently, relaxin can be used to reduce cardiac decompensation events by selecting human subjects including AHF patients and/or individuals with AHF symptoms and/or individuals suffering from acute vascular failure who present with acute cardiac decompensation, and administering to those subjects a pharmaceutical formulation with pharmaceutically active relaxin. Relaxin reduces the acute cardiac decompensation events by binding to the relaxin receptors (e.g., LRG7, LGR8, GPCR135, GPCR142 receptors) resulting in balanced vasodilation, i.e., a dual vasodilation in both the systemic and renal vasculature. Based on those same principles, relaxin can be used to treat cardiac decompensation in human subjects including AHF patients and/or individuals associated with symptoms of AHF and/or individuals suffering from acute vascular failure. Particularly, such subjects receive pharmaceutically active human relaxin (e.g., synthetic, recombinant) or pharmaceutically effective relaxin agonist in an amount in a range of about 10 to 1000 μg/kg of subject body weight per day. In one embodiment, the dosages of relaxin are 10, 30, 100 and 250 μg/kg/day. In another embodiment, these dosages result in serum concentrations of relaxin of about 3, 10, 30 and 75 ng/ml, respectively. In one preferred embodiment, pharmaceutically effective relaxin or an agonist thereof is administered at about 30 μg/kg/day. In another preferred embodiment, pharmaceutically effective relaxin or an agonist thereof is administered at about 10 to about 250 μg/kg/day. In another embodiment, the administration of relaxin is continued as to maintain a serum concentration of relaxin of from about 0.5 to about 500 ng/ml, more preferably from about 0.5 to about 300 ng/ml, and most preferably from about 3 to about 75 ng/ml. Most preferably, the administration of relaxin is continued as to maintain a serum concentration of relaxin of about 10 ng/ml or greater. Relaxin has also been shown to be fully effective at a serum concentration of 3-6 ng/ml. Thus, the methods of the present disclosure include administrations that result in these serum concentrations of relaxin. These relaxin concentrations can ameliorate or reduce decompensation events such as dyspnea, hypertension, arrhythmia, reduced renal blood flow, and renal insufficiency. Furthermore, these relaxin concentrations can ameliorate or reduce neurohormonal imbalance, fluid overload, cardiac arrhythmia, cardiac ischemia, risk of mortality, cardiac stress, vascular resistance, and the like.

The duration of relaxin treatment is preferably kept at a range of about 4 hours to about 96 hours depending on the patient, and one or more optional repeat treatments as needed. For example, with respect to frequency of administration, relaxin administration can be a continuous infusion lasting from about 8 hr to 72 hours of treatment. Relaxin can be given continuously via intravenous or subcutaneous administration. For intravenous administration, relaxin can be delivered by syringe pump or through an IV bag. The IV bag can be a standard saline, half normal saline, 5% dextrose in water, lactated Ringer's or similar solution in a 100, 250, 500 or 1000 ml IV bag. For subcutaneous infusion, relaxin can be administered by a subcutaneous infusion set connected to a wearable infusion pump. Depending on the subject, the relaxin administration is maintained for as specific period of time or for as long as needed to achieve stability in the subject.

Some subjects are treated indefinitely while others are treated for specific periods of time. It is also possible to treat a subject on and off with relaxin as needed. Thus, administration can be continued over a period of time sufficient to achieve an amelioration or reduction in acute cardiac decompensation events, including but not limited to, dyspnea, hypertension, arrhythmia, reduced renal blood flow and renal insufficiency. Relaxin may be administered in higher doses if necessary to prevent death due to AHF and/or acute vascular failure associated complications such as sudden cardiac arrest.

Relaxin Treatment Does Not Cause Renal Toxicity and is Diuretic-Sparing

Renal dysfunction is a common and progressive complication of acute and chronic heart failure. The clinical course typically fluctuates with the patient's clinical status and treatment. Despite the growing recognition of the frequent presentation of combined cardiac and renal dysfunction, also termed the "cardiorenal syndrome," its underlying pathophysiology is not well understood. No consensus as to its appropriate management has been achieved in the art. Because patients with heart failure are surviving longer and die less frequently from cardiac arrhythmia, cardiorenal syndrome is more and more prevalent and proper management is needed (Gary Francis (2006) *Cleveland Clinic Journal of Medicine* 73(2):1-13). The disclosure solves this need. It provides a method of treating acute decompensated heart failure (AHF) and/or acute vascular failure in a human subject who also suffers from renal insufficiency. This method includes selecting a human subject with symptoms of acute cardiac decompensation and renal insufficiency, wherein the subject has a systemic and renal vasculature comprising relaxin receptors. Relaxin is administered to the subject and performs a dual action by binding to the relaxin receptors in the systemic and renal vasculature, resulting in balanced vasodilation. As noted above, such subjects receive pharmaceutically active human relaxin (e.g., synthetic, recombinant) or pharmaceutically effective relaxin agonist in an amount in a range of about 10 to 1000 µg/kg of subject body weight per day. In one embodiment, the dosages of relaxin are 10, 30, 100 and 250 µg/kg/day. In another embodiment, these dosages result in serum concentrations of relaxin of about 3, 10, 30 and 75 ng/ml, respectively. In one preferred embodiment, pharmaceutically effective relaxin or an agonist thereof is administered at about 30 µg/kg/day. In another preferred embodiment, pharmaceutically effective relaxin or an agonist thereof is administered at about 10 to about 250 µg/kg/day. The administration of relaxin is continued as to maintain a serum concentration of relaxin of from about 0.5 to about 500 ng/ml, more preferably from about 0.5 to about 300 ng/ml, and most preferably from about 3 to about 75 ng/ml. Most preferably, the administration of relaxin is continued as to maintain a serum concentration of relaxin of 10 ng/ml or greater. Depending on the subject, the relaxin administration is maintained for as specific period of time or for as long as needed to achieve stability in the subject. For example, the duration of relaxin treatment is preferably kept at a range of about 4 hours to about 96 hours, more preferably from about 8 hr to 72 hours, depending on the patient, and one or more optional repeat treatments as needed.

Subjects who suffer from renal insufficiency associated with AHF often also experience elevated levels of brain natriuretic peptide (BNP). BNP is synthesized in the cardiac ventricles in response to heart failure and left ventricular dysfunction. It is used as a diagnostic marker of heart failure. Its effects include systemic vasodilation and unbalanced vasodilation in the kidney, i.e., efferent arteriolar constriction and afferent arteriole vasodilation. As described herein, brain natriuretic peptide (BNP) levels are reduced when relaxin is administered to AHF patients and/or patients with acute vascular failure. This makes BNP a convenient AHF marker since it is reduced as the severity of AHF is reduced. Monitoring BNP levels in patients that are treated with relaxin is, thus, a convenient way to assess the risk of mortality associated with AHF and/or acute vascular failure. Thus, the disclosure provides a method for reducing mortality risk in a human subject with symptoms of acute cardiac decompensation. The relaxin is administered in an amount effective to reduce the acute cardiac decompensation in the subject by binding to the relaxin receptors in the vasculature of the subject, thereby resulting in reduced levels of BNP. The reduced levels of BNP can be physically measured in order to predict risk of mortality in the AHF and/or acute vascular failure patient. Generally, the reduced levels of BNP are due to reduced cardiac stress following a reduction in vascular resistance. The reduction in vascular resistance is in turn due to the balanced vasodilation which is the result of relaxin binding to relaxin receptors that are found on smooth muscle cells of the vasculature.

Relaxin causes low to no renal toxicity when it is given to AHF and/or acute vascular failure patients in comparison to most available drugs. Even with higher serum concentrations of about 75 ng/ml relaxin is far less toxic than currently available medications (e.g., loop diuretics such as furosemide, angiotensin converting enzyme inhibitors such as captopril, angiotensin receptor blockers such as candesartan, and the like). One important feature of this disclosure is that relaxin preserves the renal function while causing little to no renal toxicity during treatment. Although existing drugs may preserve some renal function they also increase renal toxicity in patients. This renal toxicity then further deteriorates the heart condition. In comparison, relaxin will achieve a steady-state maintenance of most patients due to the absence of renal toxicity. This allows the unstable AHF and/or acute vascular failure population to revert back to a more stable CHF population or to achieve a stable condition where the likelihood of exacerbating heart failure is significantly reduced.

Relaxin Compositions and Formulations

Relaxin, relaxin agonists and/or relaxin analogs are formulated as pharmaceuticals to be used in the methods of the disclosure. Any composition or compound that can stimulate a biological response associated with the binding of biologically or pharmaceutically active relaxin (e.g., synthetic relaxin, recombinant relaxin) or a relaxin agonist (e.g., relaxin analog or relaxin-like modulator) to relaxin receptors can be used as a pharmaceutical in the disclosure. General details on techniques for formulation and administration are well described in the scientific literature (see *Remington's Pharmaceutical Sciences*, Maack Publishing Co, Easton Pa.). Pharmaceutical formulations containing pharmaceutically active relaxin can be prepared according to any method known in the art for the manufacture of pharmaceuticals. The formulations containing pharmaceutically active relaxin or relaxin agonists used in the methods of the disclosure can be formulated for administration in any conventionally acceptable way including, but not limited to, intravenously, subcutaneously, intramuscularly, sublingually, topically, orally and via inhalation. Illustrative examples are set forth below. In one preferred embodiment, relaxin is administered intravenously.

When the drugs are delivered by intravenous injection, the formulations containing pharmaceutically active relaxin or a pharmaceutically effective relaxin agonist can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, capsules, liquids, lozenges, gels, syrups, slurries, suspensions, etc., suitable for ingestion by the patient. Pharmaceutical preparations for oral use can be obtained through combination of relaxin compounds with a solid excipient, optionally grinding a resulting mixture, and processing the mixture of granules, after adding suitable additional compounds, if desired, to obtain tablets or pills. Suitable solid excipients are carbohydrate or protein fillers which include, but are not limited to, sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate. Pharmaceutical preparations of the disclosure that can also be used orally are, for example, push-fit capsules made of gelatin, as well as soft, sealed capsules made of gelatin and a coating such as glycerol or sorbitol. Push-fit capsules can contain relaxin mixed with a filler or binders such as lactose or starches, lubricants such as talc or magnesium stearate, and, optionally, stabilizers. In soft capsules, the relaxin compounds may be dissolved or suspended in suitable liquids, such as fatty oils, liquid paraffin, or liquid polyethylene glycol with or without stabilizers.

Aqueous suspensions of the disclosure contain relaxin in admixture with excipients suitable for the manufacture of aqueous suspensions. Such excipients include a suspending agent, such as sodium carboxymethylcellulose, methylcellulose, hydroxypropylnethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending relaxin in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

Dispersible powders and granules of the disclosure suitable for preparation of an aqueous suspension by the addition of water can be formulated from relaxin in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical formulations of the disclosure can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

Administration and Dosing Regimen of Relaxin Formulations

The formulations containing pharmaceutically active relaxin or pharmaceutically effective relaxin agonist used in the methods of the disclosure can be administered in any conventionally acceptable way including, but not limited to, intravenously, subcutaneously, intramuscularly, sublingually, topically, orally and via inhalation. Administration will vary with the pharmacokinetics and other properties of the drugs and the patients' condition of health. General guidelines are presented below.

The methods of the disclosure reduce acute cardiac decompensation events in subjects who suffer from acute cardiac decompensation associated with AHF and/or acute vascular failure, and/or related conditions. In addition, the methods of the disclosure treat acute cardiac decompensation in subjects who suffer from acute cardiac decompensation associated with AHF, including AHF patients and/or patients with acute vascular failure. The amount of relaxin alone or in combination with another agent or drug (e.g., diuretic) that is adequate to accomplish this is considered the therapeutically effective dose. The dosage schedule and amounts effective for this use, i.e., the "dosing regimen," will depend upon a variety of factors, including the stage of the disease or condition, the severity of the disease or condition, the severity of the adverse side effects, the general state of the patient's health, the patient's physical status, age and the like. In calculating the dosage regimen for a patient, the mode of administration is also taken into consideration. The dosage regimen must also take into consideration the pharmacokinetics, i.e., the rate of absorption, bioavailability, metabolism, clearance, and the like. Based on those principles, relaxin can be used to treat cardiac decompensation in human subjects including AHF patients and/or individuals associated with symptoms of AHF and/or individuals who suffer from acute vascular failure.

The disclosure provides relaxin and a diuretic for simultaneous, separate or sequential administration. The disclosure also provides relaxin and a diuretic for combined use in therapy. The disclosure also provides the combination of relaxin and a diuretic for use in therapy. The disclosure also provides the use of relaxin and a diuretic in the manufacture of a medicament for treating acute cardiac decompensation events. The disclosure also provides the use of relaxin in the manufacture of a medicament for treating acute cardiac decompensation events, wherein the medicament is prepared for administration with a diuretic. The disclosure also provides the use of a diuretic in the manufacture of a medicament for treating acute cardiac decompensation events, wherein the medicament is prepared for administration with relaxin. The disclosure also provides relaxin and a diuretic for use in a method of treating acute cardiac decompensation events.

The disclosure further provides relaxin for use in a method of treating acute cardiac decompensation events, wherein relaxin is prepared for administration with a diuretic. The disclosure also provides a diuretic for use in a method of treating acute cardiac decompensation events, wherein relaxin is prepared for administration with relaxin. The disclosure also provides relaxin for use in a method of treating acute cardiac decompensation events, wherein relaxin is administered with a diuretic. The disclosure also provides a diuretic for use in a method of treating acute cardiac decompensation events, wherein relaxin is administered with relaxin.

Further contemplates is the use of relaxin in the manufacture of a medicament for treating acute cardiac decompensation events, wherein the patient has previously (e.g., a few hours before, one or more days before, etc.) been treated with a diuretic. In one embodiment, the diuretic is still active in vivo in the patient. The disclosure also provides the use of a diuretic in the manufacture of a medicament for treating acute cardiac decompensation events, wherein the patient has previously been treated with relaxin.

Figure 6:
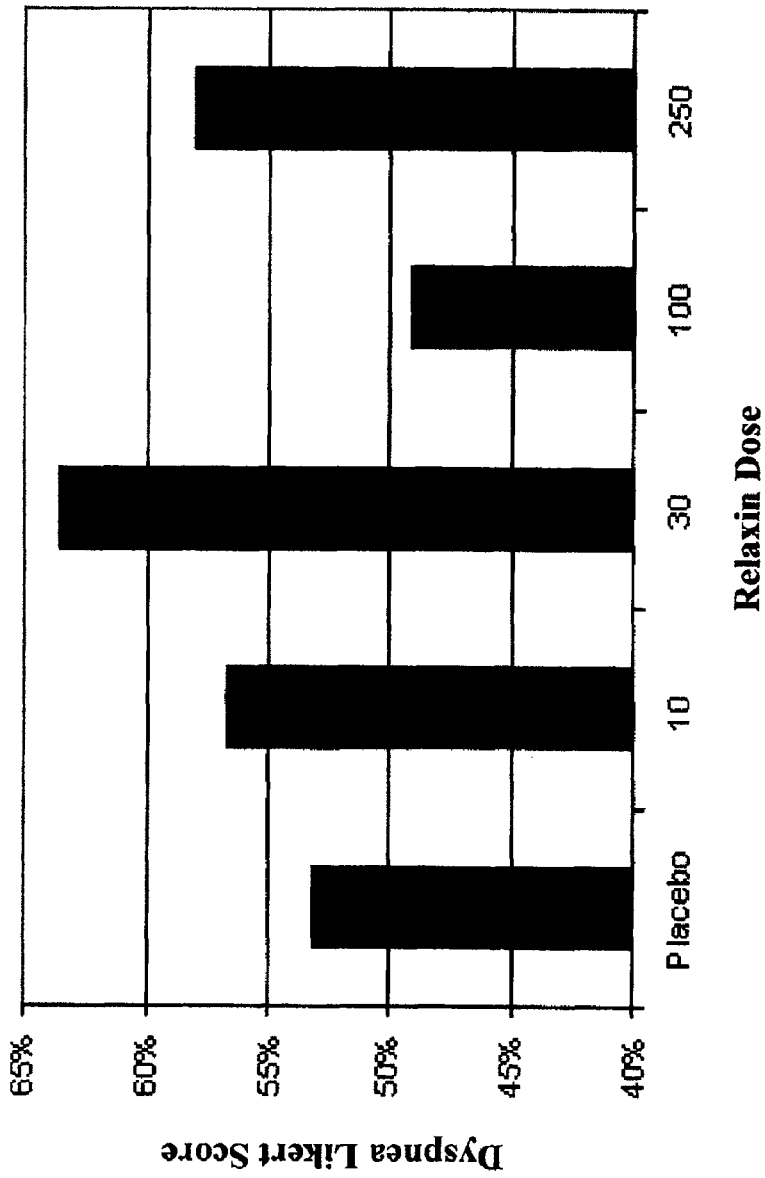
FIG. 6 depicts a Likert graph of percent moderate or marked improvement in dyspnea in AHF patients treated with various dosages of relaxin (i.e., 10, 30, 100 and 250 µg/kg/day) as an average of all time points.
Figure 7:
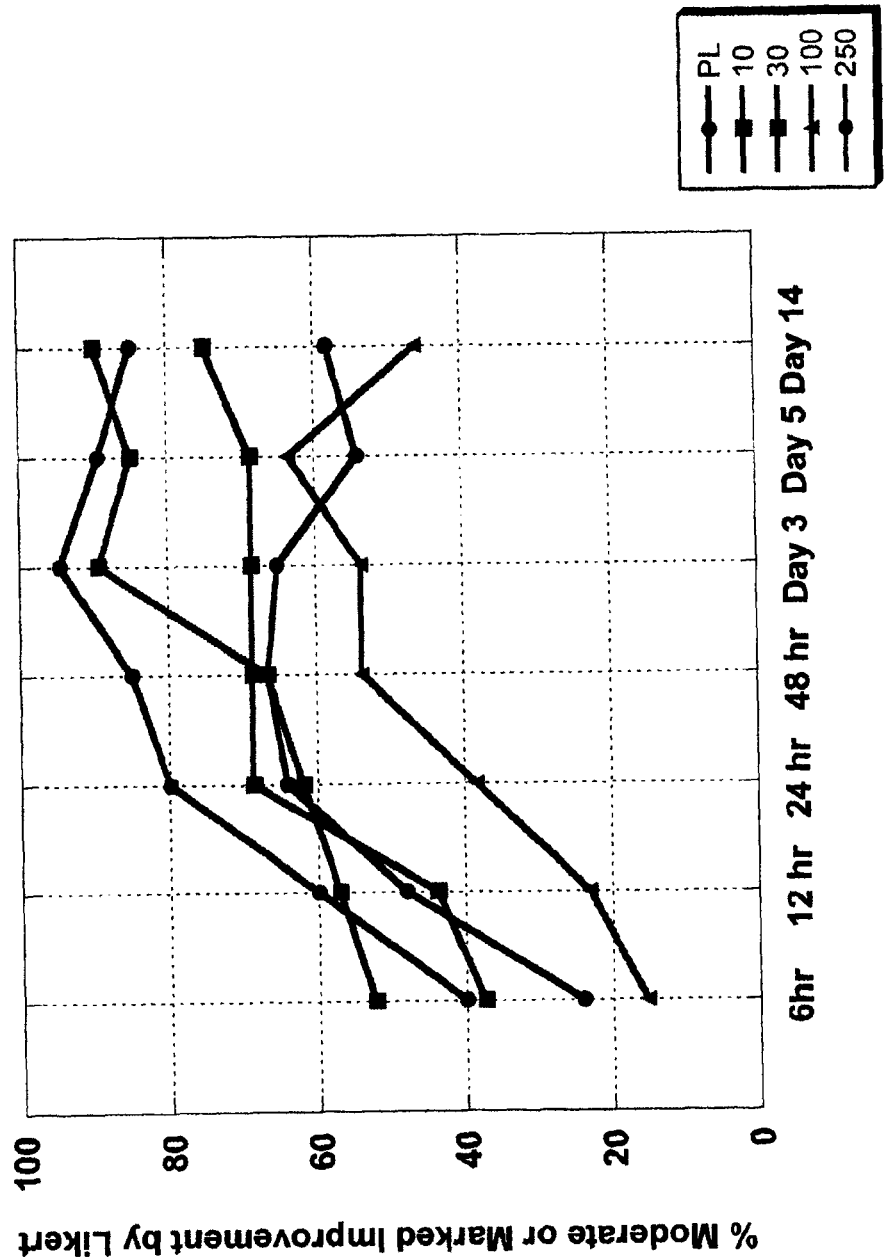
FIG. 7 depicts a Likert graph of percent moderate or marked improvement in dyspnea when patients suffering from AHF with a systolic blood pressure (SBP) greater than the median were treated with various dosages of relaxin (i.e., 10, 30, 100 and 250 µg/kg/day). A beneficial effect was first seen at 6 hours of treatment and relaxin administered at 30 µg/kg/day showed a sustained effect with about 90% improvement lasting over a period of 14 days. In comparison, placebo treated patients continued to decline after the placebo effect wore off.
Figure 8:
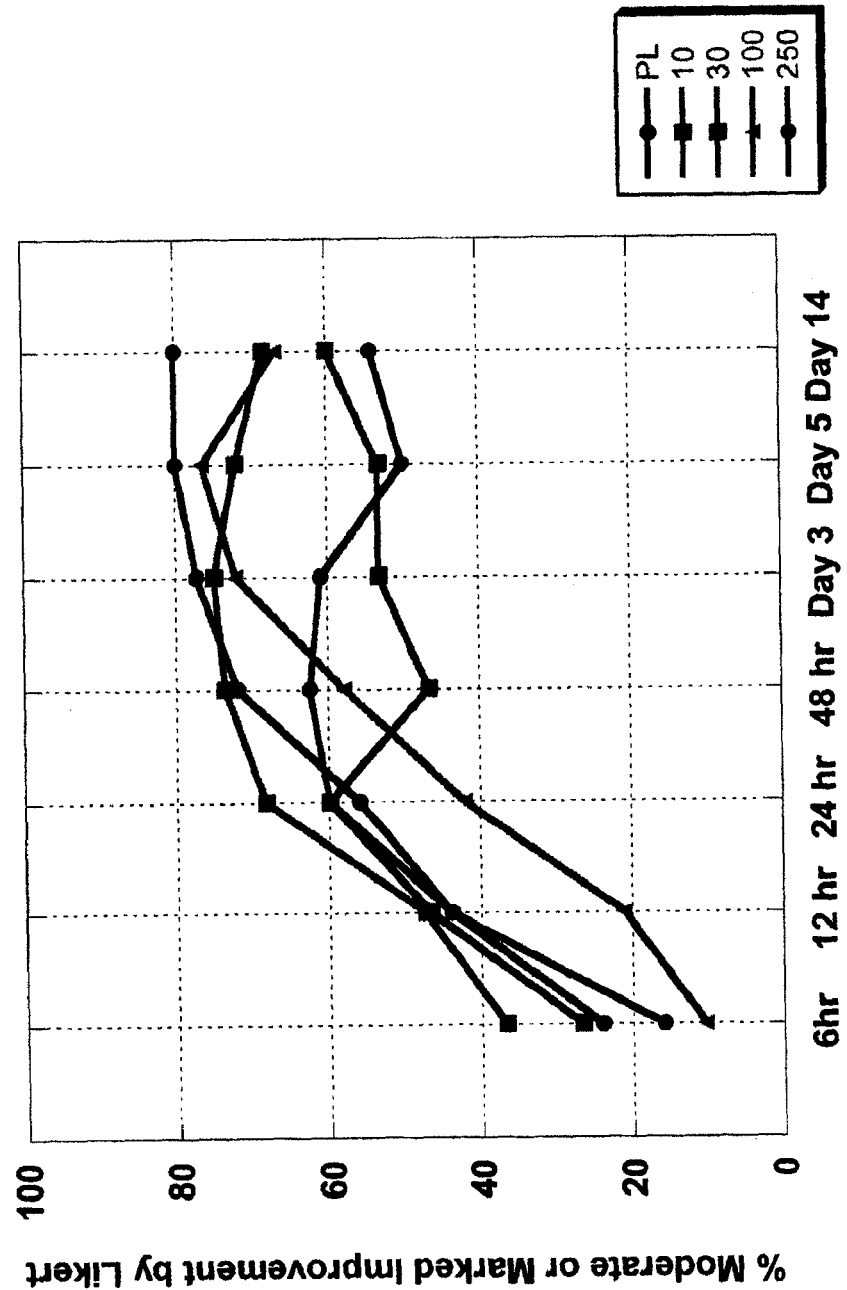
FIG. 8 depicts a Likert graph of percent moderate or marked improvement in dyspnea when patients suffering from AHF with a creatinine clearance (CrCl) of less than the median were treated with various dosages of relaxin (i.e., 10, 30, 100 and 250 µg/kg/day) over a period of 48 hours. A beneficial effect was first seen at 6 hours of treatment and relaxin showed a sustained effect across various dosages lasting over a period of 14 days. In comparison, placebo treated patients continued to decline after the placebo effect wore off.
Figure 9:
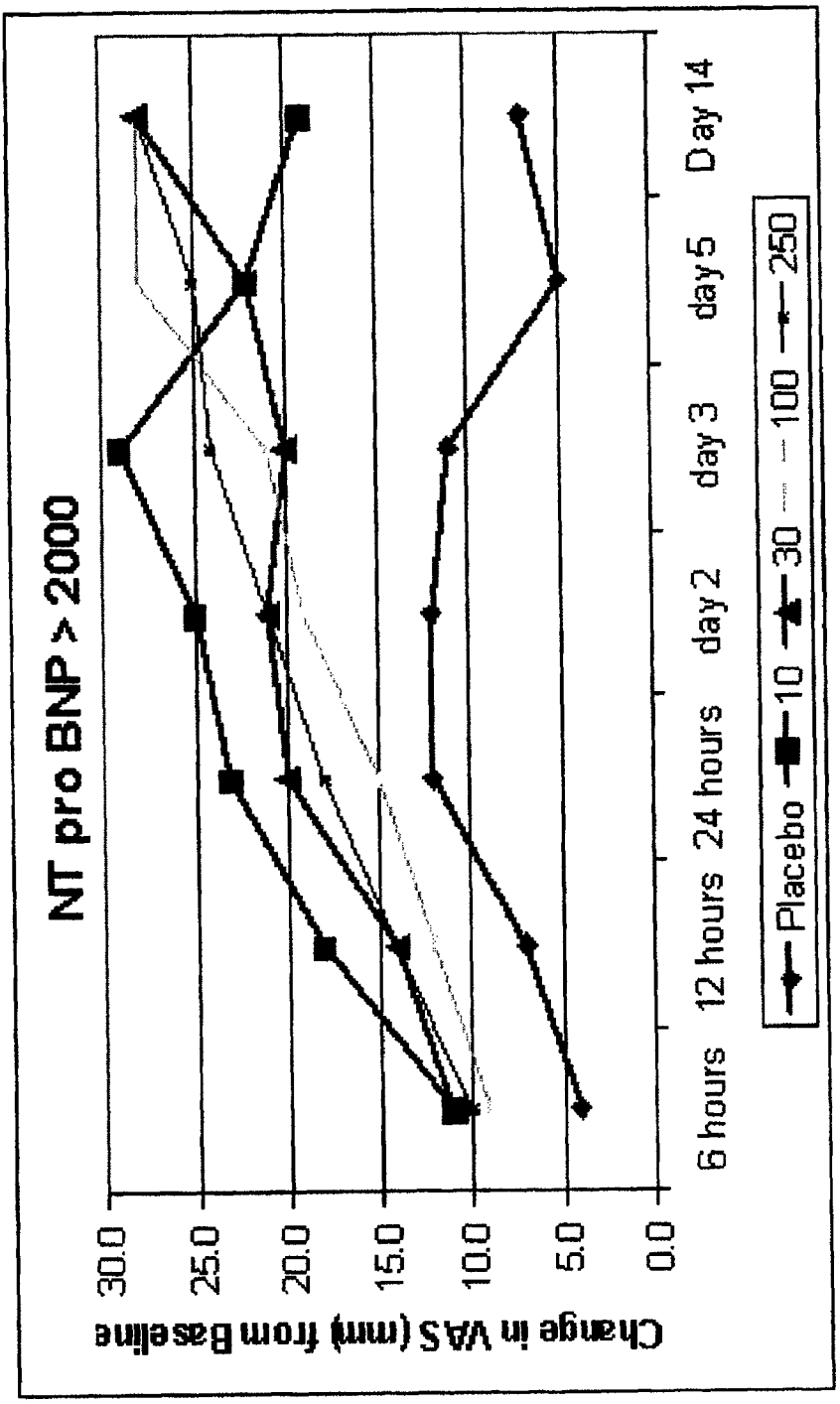
FIG. 9 shows a VAS graph of dyspnea improvement when AHF patients with NT-pro-BNP levels greater than 2000 were treated with various dosages of relaxin (i.e., 10, 30, 100 and 250 µg/kg/day) over a period of 48 hours. A marked improvement was seen in patients treated with relaxin dosages of 30 µg/kg/day and higher compared to patients treated with placebo.
Figure 10:
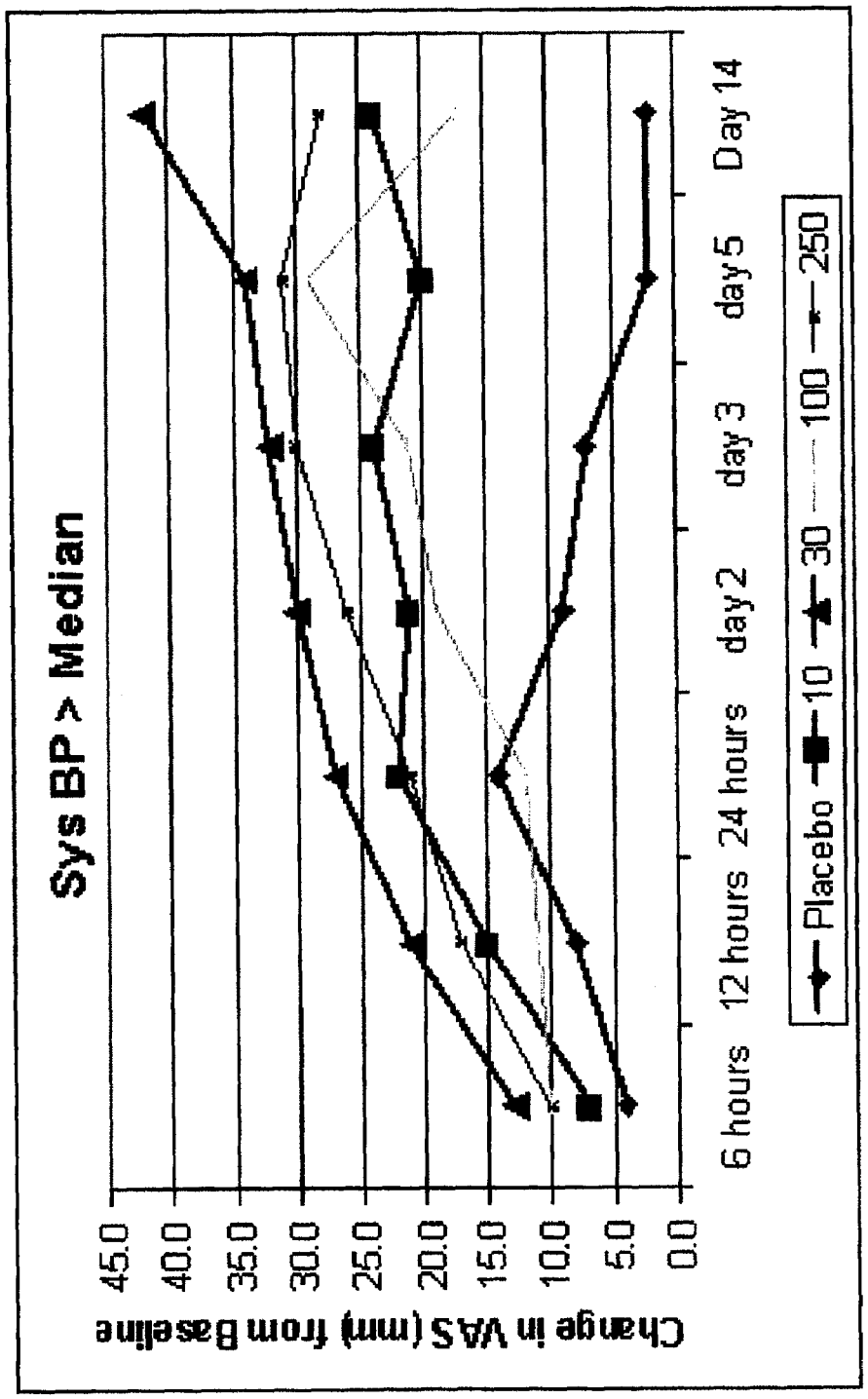
FIG. 10 shows a VAS graph of dyspnea improvement when AHF patients with systolic blood pressure (SBP) levels greater than the median were treated with various dosages of relaxin (i.e., 10, 30, 100 and 250 µg/kg/day) over a period of 48 hours. A particularly marked improvement was seen in patients treated with relaxin at 30 µg/kg/day compared to patients treated with placebo.
Figure 11:
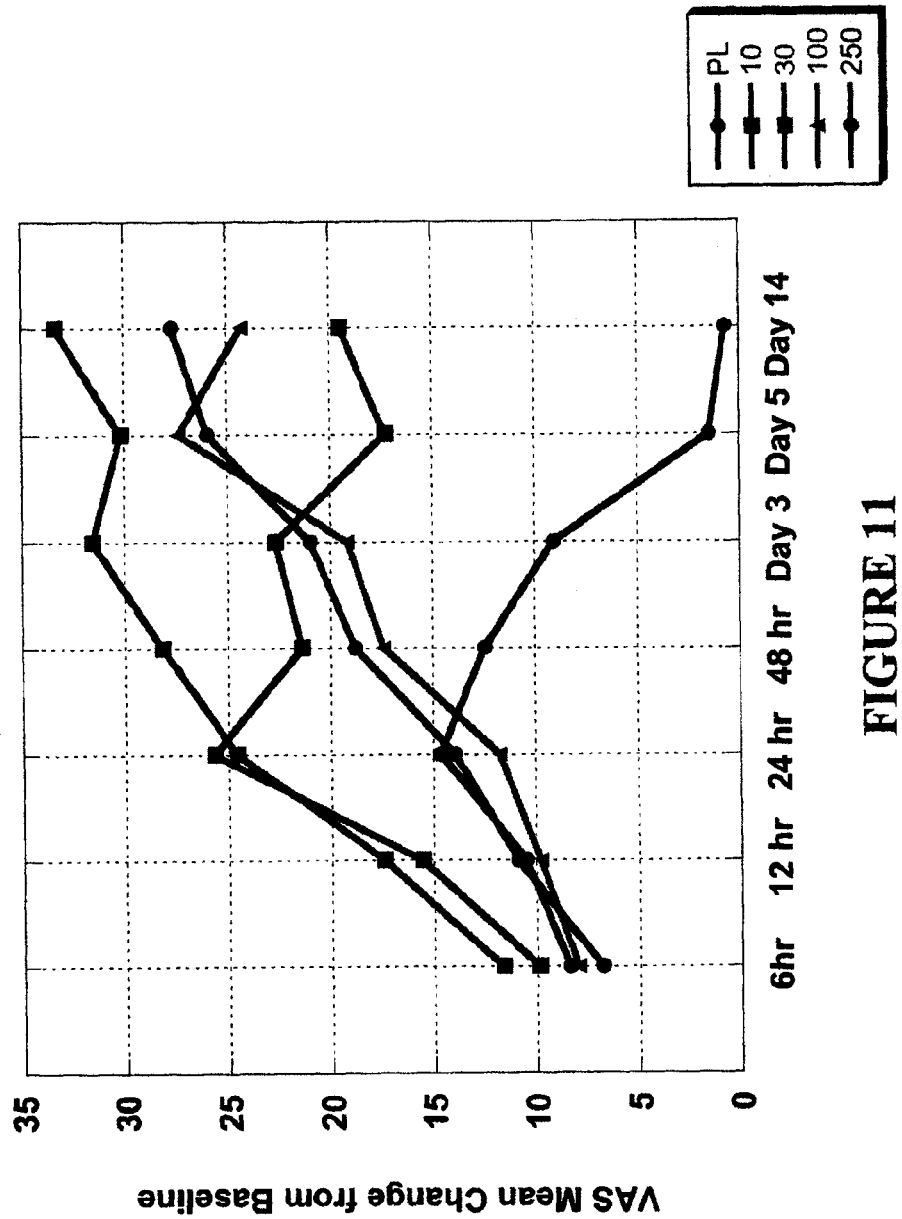
FIG. 11 shows a VAS graph of dyspnea improvement when AHF patients with creatinine clearance (CrCl) less than the median were treated with various dosages of relaxin (i.e., 10, 30, 100 and 250 µg/kg/day) over a period of 48 hours. A marked improvement was seen in patients treated with various relaxin dosages. At 30 µg/kg/day of relaxin patients experienced a sustained beneficial effect compared to patients treated with placebo.

The state of the art allows the clinician to determine the dosage regimen of relaxin for each individual patient. As an illustrative example, the guidelines provided below for relaxin can be used as guidance to determine the dosage regimen, i.e., dose schedule and dosage levels, of formulations containing pharmaceutically active relaxin administered when practicing the methods of the disclosure. As a general guideline, it is expected that the daily dose of pharmaceutically active H1, H2 and/or H3 human relaxin (e.g., synthetic, recombinant, analog, agonist, etc.) is typically in an amount in a range of about 10 to 1000 µg/kg of subject body weight per day. In one embodiment, the dosages of relaxin are 10, 30, 100 and 250 µg/kg/day. In another embodiment, these dosages result in serum concentrations of relaxin of about 3, 10, 30 and 75 ng/mL, respectively. In one preferred embodiment, pharmaceutically effective relaxin or an agonist thereof is administered at about 30 µg/kg/day. In another preferred embodiment, pharmaceutically effective relaxin or an agonist thereof is administered at about 10 to about 250 µg/kg/day. In another embodiment, the administration of relaxin is continued as to maintain a serum concentration of relaxin of from about 0.5 to about 500 ng/ml, more preferably from about 0.5 to about 300 ng/ml, and most preferably from about 3 to about 75 ng/ml. Most preferably, the administration of relaxin is continued as to maintain a serum concentration of relaxin of 10 ng/ml or greater. Relaxin has also been shown to be fully effective at a serum concentration of 3-6 ng/ml (see FIG. 6, vide infra). Thus, the methods of the present disclosure include administrations that result in these serum concentrations of relaxin. These relaxin concentrations can ameliorate or reduce decompensation events such as dyspnea, hypertension, high blood pressure, arrhythmia, reduced renal blood flow, renal insufficiency and mortality. Furthermore, these relaxin concentrations can ameliorate or reduce neurohormonal imbalance, fluid overload, cardiac arrhythmia, cardiac ischemia, risk of mortality, cardiac stress, vascular resistance, and the like. Depending on the subject, the relaxin administration is maintained for as specific period of time or for as long as needed to achieve stability in the subject. For example, the duration of relaxin treatment is preferably kept at a range of about 4 hours to about 96 hours, more preferably 8 hours to about 72 hours, depending on the patient, and one or more optional repeat treatments as needed.

Single or multiple administrations of relaxin formulations may be administered depending on the dosage and frequency as required and tolerated by the patient who suffers from acute cardiac decompensation, AHF and/or conditions related to AHF and/or individuals suffering from acute vascular failure. The formulations should provide a sufficient quantity of relaxin to effectively ameliorate the condition. A typical pharmaceutical formulation for intravenous administration of relaxin would depend on the specific therapy. For example, relaxin may be administered to a patient through monotherapy (i.e., with no other concomitant medications) or in combination therapy with another medication such as a diuretic or other drug. In one embodiment, relaxin is administered to a patient daily as monotherapy. In another embodiment, relaxin is administered to a patient daily as combination therapy with another drug. Notably, the dosages and frequencies of relaxin administered to a patient may vary depending on age, degree of illness, drug tolerance, and concomitant medications and conditions.

In some embodiments, relaxin is provided as a 1 mg/mL solution (3.5 mL in 5 mL glass vials). Placebo, which is identical to the diluent for relaxin, is provided in identical vials. Relaxin or placebo is administered intravenously to the patient in small volumes using a syringe pump in combination with normal saline in a piggyback configuration. Compatible tubing and a 3-way stopcock, which have been tested and qualified for use with relaxin are used to administer the relaxin formulation. Doses are administered on a weight basis and adjusted for each patient by adjusting the rate of relaxin drug delivered by the infusion pump. In some embodiments, each subject is dosed for up to 48 hours with study drug.

Adjunct Therapies for Treating Normotensive and Hypertensive AHF Patients

There are a wide variety of approved antihypertensive drugs including vasodilators, adrenergic blockers, centrally acting alpha-agonists, angiotensin-converting enzyme (ACE) inhibitors, angiotensin II receptor blockers (ARBs), calcium channel blockers and multiple types of diuretics (e.g., loop, potassium-sparing, thiazide and thiazide-like). In some embodiments, the present disclosure provides methods of treating dyspnea associated with acute heart failure in normotensive and hypertensive patients comprising administration of relaxin in combination with an adjunct therapy such as an antihypertensive drug. In some methods, the antihypertensive drug is selected from but not limited to the following ACE inhibitors, beta-blockers and diuretics.

Angiotensin Converting Enzyme (ACE) inhibitors have been used for the treatment of hypertension for many years. ACE inhibitors block the formation of angiotensin II, a hormone with adverse effects on the heart and circulation in CHF patients. Side effects of these drugs include a dry cough, low blood pressure, worsening kidney function and electrolyte imbalances, and sometimes, allergic reactions. Examples of ACE inhibitors include captopril (CAPOTEN), enalapril (VASOTEC), lisinopril (ZESTRIL, PRINIVIL), benazepril (LOTENSIN), and ramipril (ALTACE). For those patients who are unable to tolerate ACE inhibitors, an alternative group of drugs, called the angiotensin receptor blockers (ARBs), can be used. These drugs act on the same hormonal pathway as ACE inhibitors, but instead block the action of angiotensin II at its receptor site directly. Side effects of these drugs are similar to those associated with ACE inhibitors, although the dry cough is less common. Examples of this class of medications include losartan (COZAAR), candesartan (ATACAND), telmisartan (MICARDIS), valsartan (DIOVAN), and irbesartan (AVAPRO).

Beta-blockers are drugs that block the action of certain stimulating hormones, such as epinephrine (adrenaline), norepinephrine, and other similar hormones, which act on the beta receptors of various body tissues. The natural effect of these hormones on the beta receptors of the heart is a more forceful contraction of the heart muscle. Beta-blockers are agents that block the action of these stimulating hormones on the beta receptors. The stimulating effect of these hormones, while initially useful in maintaining heart function, appears, to have detrimental effects on the heart muscle over time. Generally, if CHF patients receive beta-blockers they are given at a very low dose at first which is then gradually increased. Side effects include fluid retention, low blood pressure, low pulse, and general fatigue and lightheadedness. Beta-blockers should also not be used in people with diseases of the airways (e.g., asthma, emphysema) or very low resting heart rates. Carvedilol (COREG) has been the most thoroughly studied drug in the setting of congestive heart failure and remains the only beta-blocker with FDA approval for the treatment of congestive heart failure. However, research comparing carvedilol directly with other beta-blockers in the treatment of congestive heart failure is ongoing. Long acting metopropol (TOPROL XL) is also effective in patients with congestive heart failure. Digoxin (LANOXIN) is naturally produced by the Foxglove flowering plant and has been used for treatment of CHF patients for a decade. Digoxin stimulates the heart muscle to contract more forcefully. Side effects include nausea, vomiting, heart rhythm disturbances, kidney dysfunction, and electrolyte abnormalities. In patients with significant kidney impairment the dose of digoxin needs to be carefully adjusted and monitored.

Diuretics are often used in the treatment of CHF patients to prevent or alleviate the symptoms of fluid retention. These drugs help keep fluid from building up in the lungs and other tissues by promoting the flow of fluid through the kidneys. Although they are effective in relieving symptoms such as shortness of breath and leg swelling, they have not been demonstrated to positively impact long term survival. When hospitalization is required, diuretics are often administered intravenously because the ability to absorb oral diuretics may be impaired. Side effects of diuretics include dehydration, electrolyte abnormalities, particularly low potassium levels, hearing disturbances, and low blood pressure. It is important to prevent low potassium levels by providing supplements to patients, when appropriate. Any electrolyte imbalances may make patients susceptible to serious heart rhythm disturbances. Examples of various classes of diuretics include furosemide (LASIX), hydrochlorothiazide, bumetanide (BUMEX), torsemide (DEMADEX), and metolazone (ZAROXOLYN). Spironolactone (ALDACTONE) has been used for many years as a relatively weak diuretic in the treatment of various diseases. This drug blocks the action of the hormone aldosterone. Aldosterone has theoretical detrimental effects on the heart and circulation in congestive heart failure. Its release is stimulated in part by angiotensin II (supra). Side effects of this drug include elevated potassium levels and, in males, breast tissue growth (gynecomastia). Another aldosterone inhibitor is eplerenone (INSPRA).

Relaxin Agonists

In some embodiments, the present disclosure provides methods of treating dyspnea associated with acute heart failure in normotensive or hypertensive patients comprising administration of a relaxin agonist. In some methods, the relaxin agonist activates one or more relaxin-related G-protein coupled receptors (GPCR) selected from but not limited to RXFP1, RXFP2, RXFP3, RXFP4, FSHR (LGR1), LHCGR (LGR2), TSHR (LGR3), LGR4, LGR5, LGR6 LGR7 (RXFP1) and LGR8 (RXFP2). In some embodiments, the relaxin agonist comprises the amino acid sequence of Formula I of WO 2009/007848 of Compugen (herein incorporated by reference for the teaching of relaxin agonist sequences).

Formula I peptides are preferably from 7 to 100 amino acids in length and comprise the amino acid sequence: X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33; wherein X1 is absent or G or a small naturally or non-naturally occurring amino acid; X2 is absent or Q or a polar naturally or non-naturally occurring amino acid; X3 is absent or K or a basic naturally or non-naturally occurring amino acid; X4 is absent or G or a small naturally or non-naturally occurring amino acid; X5 is absent or Q or S a polar naturally or non-naturally occurring amino acid; X6 is absent or V or A or P or M or a hydrophobic naturally or non-naturally occurring amino acid; X7 is absent or G or a small naturally or non-naturally occurring amino acid; X8 is absent or P or L or A naturally or non-naturally occurring amino acid; X9 is absent or P or Q naturally or non-naturally occurring amino acid; X10 is absent or G or a small naturally or non-naturally occurring amino acid; X11 is absent or A or H or E or D or a hydrophobic or a small or an acidic naturally or non-naturally occurring amino acid; X12 is absent or A or P or Q or S or R or H or a hydrophobic or a small naturally or non-naturally occurring amino acid; X13 is absent or C or V or a hydrophobic naturally or non-naturally occurring amino acid; X14 is absent or R or K or Q or P or a basic or a polar naturally or non-naturally occurring amino acid; X15 is absent or R or Q or S or a basic or a polar naturally or non-naturally occurring amino acid; X16 is absent or A or L or H or Q or a hydrophobic or a small naturally or non-naturally occurring amino acid; X17 is absent or Y or a hydrophobic or an aromatic naturally or non-naturally occurring amino acid; X18 is absent or A or a hydrophobic or small naturally or non-naturally occurring amino acid; X19 is absent or A or a hydrophobic small naturally or non-naturally occurring amino acid; X20 is absent or F or a hydrophobic or an aromatic naturally or non-naturally occurring amino acid; X21 is absent or S or T or a polar naturally or non-naturally occurring amino acid; X22 is absent or V or a hydrophobic naturally or non-naturally occurring amino acid; X23 is absent or G or hydrophobic or small non-naturally occurring amino acid or replaced by an amide; X24 is absent or R or a basic naturally or non-naturally occurring amino acid; X25 is absent or R or a basic naturally or non-naturally occurring amino acid; X26 is A or a hydrophobic or small naturally or non-naturally occurring amino acid; X27 is Y or a hydrophobic or an aromatic naturally or non-naturally occurring amino acid; X28 is A or a hydrophobic or small naturally or non-naturally occurring amino acid; X29 is A or a hydrophobic or small naturally or non-naturally occurring amino acid; X30 is F or a hydrophobic naturally or non-naturally occurring amino acid; X31 is S or T or a polar naturally or non-naturally occurring amino acid; X32 is V or a hydrophobic naturally or non-naturally occurring amino acid; X33 is absent or G or hydrophobic or small naturally or non-naturally occurring amino acid or replaced by an amide; or a pharmaceutically acceptable salt thereof (SEQ ID NO:4). In some preferred embodiments, the relaxin agonist comprises the sequence of peptide P59C13V (free acid) GQKGQVGPPGAA VRRA Y AAFSV (SEQ ID NO:5). In another preferred embodiment, the relaxin agonist comprises the sequence of peptide P74C13V (free acid) GQKGQVGP-PGAA VRRA Y AAFS VGRRA Y AAFS V (SEQ DD NO: 6). Further derivatives of the human complement C1Q tumor necrosis factor-related protein 8 (CTRP8 or C1QT8) such as peptide P59-G (free acid Gly) GQKGQVGPPGAACRRA Y AAFSVG (SEQ ID NO:7) are also contemplated to be suitable for use in the methods of the present disclosure. The amino acid sequence of C1QT8 is set forth as SEQ ID NO:8 MAAPALLLLALLLPVGAWPGLPRRPCVH-CCRPAWPPGPYARVSDRDLWRGDLWRGLP RVRPTI-DIEILKGEKGEAGVRGRAGRSGKEGPP-GARGLQGRRGQKGQVGPPGAACRRA YAAFSVGRRAYAAFSVGRREGLHSSDH-FQAVPFDTELVNLDGAFDLAAGRFLCTVPGV YFLSLNVHTWNYKETYLHIMLNRRPAAV-LYAQPSERSVMQAQSLMLLLAAGDAVWVR MF QRDRDNAIYGEHGDLYITFSGHLVKP AAEL.

The present disclosure also encompasses encompasses homologues of these polypeptides, such homologues can be at least 50%, at least 55%, at least 60%, at least 65%, at least 70%, at least 75%, at least 80%, at least 85%, at least 85%, at least 90%, at least 95% or more say 100% identical to the amino acid sequence of an exemplary relaxin agonist (e.g., SEQ ID NO:5 or SEQ ID NO:6), as can be determined using BlastP software of the National Center of Biotechnology Information (NCBI) using default parameters, optionally and preferably including the following: filtering on (this option filters repetitive or low-complexity sequences from the query using the Seg (protein) program), scoring matrix is BLOSUM62 for proteins, word size is 3, E value is 10, gap costs are 1 1, 1 (initialization and (initialization and extension). Optionally and preferably, nucleic acid sequence identity/homology is determined with BlastN software of the National Center of Biotechnology Information (NCBI) using default parameters, which preferably include using the DUST filter program, and also preferably include having an E value of 10, filtering low complexity sequences and a word size of 1 1. Finally the present disclosure also encompasses fragments of the above described polypeptides and polypeptides having mutations, such as deletions, insertions or substitutions of one or more amino acids, either naturally occurring or artificially induced, either randomly or in a targeted fashion.

Medical Uses

The disclosure provides medical uses of relaxin as defined above. Thus, for example, the disclosure provides a relaxin for use in treating dyspnea in a human subject. In another embodiment the disclosure provides a relaxin for use in treating acute decompensated heart failure in a human subject, wherein the subject has acute decompensated heart failure and a systolic blood pressure of at least 125 mm Hg, and wherein the method comprises administering the H2 relaxin to the subject in an amount effective to reduce their in hospital worsening heart failure. In another embodiment the disclosure provides a relaxin for use in treating acute decompensated heart failure in a human subject, wherein the subject has acute decompensated heart failure and a left ventricular ejection fraction of at least about 20%, and wherein the method comprises administering the H2 relaxin to the subject in an amount effective to reduce at least one acute heart failure sign or symptom in the subject. The disclosure also provides a relaxin for use in treating acute decompensated heart failure in a human subject, wherein the subject has acute decompensated heart failure, and wherein the method comprises administering the H2 relaxin to the subject in an amount effective to reduce diuretic use during a hospital stay.

The disclosure also provides the use of a relaxin in the manufacture of a medicament for treating dyspnea in a human subject. The disclosure also provides the use of a relaxin in the manufacture of a medicament for treating acute decompensated heart failure in a human subject, wherein the subject has acute decompensated heart failure and a systolic blood pressure of at least 125 mm Hg. The disclosure also provides the use of a relaxin in the manufacture of a medicament for treating acute decompensated heart failure in a human subject, wherein the subject has acute decompensated heart failure and a left ventricular ejection fraction of at least about 20%.

Other features of the relaxin and the treatments associated with these uses are disclosed above.

The disclosure also provides the use of a relaxin and an antihypertensive drug in the manufacture of a medicament for treating the conditions discussed above. The antihypertensive drug may be selected as described above e.g. from the group consisting of vasodilators, adrenergic blockers, centrally acting alpha-agonists, angiotensin-converting enzyme inhibitors, angiotensin II receptor blockers, calcium channel blockers and diuretics.

The disclosure also provides a relaxin and an antihypertensive drug, as a combined preparation for simultaneous separate or sequential use in treating the conditions discussed above. Similarly, the disclosure provides a relaxin and an antihypertensive drug, for combined use in treating the conditions discussed above.

The disclosure also provides a relaxin for use, in combination with an antihypertensive drug, in treating the conditions discussed above. Similarly, the disclosure provides an antihypertensive drug for use, in combination with a relaxin, in treating the conditions discussed above.

The disclosure also provides a relaxin for use in a method for treating the conditions discussed above, wherein the relaxin is administered, or is prepared for administration, with an antihypertensive drug. Similarly, the disclosure provides an antihypertensive drug for use in a method for treating the conditions discussed above, wherein the antihypertensive drug is administered, or is prepared for administration, with a relaxin. The relaxin and/or antihypertensive drug may also be used in this way in the manufacture of a medicament.

The disclosure also provides a relaxin for use in a method for treating the conditions discussed above, wherein the subject previously received an antihypertensive drug in the preceding 48 hours. Similarly, the disclosure provides an antihypertensive drug for use in a method for treating the conditions discussed above, wherein the subject previously received a relaxin drug in the preceding 48 hours. The relaxin and/or antihypertensive drug may also be used in this way in the manufacture of a medicament. For these embodiments, the subjects may have received the other drug less than 48 hours previously e.g. in the preceding 24 hours, the preceding 12 hours, or the preceding 6 hours. Typically, the previously-administered drug will still be present in the subject's body and will be detectable. The remaining presence of this previously-administered drug distinguishes these subjects from the general human population.

EXPERIMENTAL

The following specific examples are intended to illustrate the disclosure and should not be construed as limiting the scope of the claims.

Abbreviations: AHF (acute heart failure or decompensated congestive heart failure); AUC (area under the curve); BNP (brain natriuretic peptide); (BP) blood pressure; BUN (blood urea nitrogen); CHF (congestive heart failure); CI (cardiac index); CO (cardiac output); CrCl (creatine clearance); DBP (diastolic blood pressure); dL (deciliters); eGFR (estimated glomerular filtration rate); hr (hour); HR (heart rate); ICU (intensive care unit); IV (intravenous); IVCD (intraventricular conduction delay); kg (kilogram); L (liter); LAHB (left anterior hemiblock); LBBB (left bundle branch block); LVEDP (left ventricular end diastolic pressure); LVEF (left ventricular ejection fraction); mcg or µg (microgram); mEq (milliequivalents); MI (myocardial infarction); mIU (milli-international units); mL (milliliter); NYHA (New York Heart Association); PAH (para-aminohippurate); PAP (pulmonary arterial pressure); PCWP (pulmonary capillary wedge pressure); PD (pharmacodynamic); RAP (right atrial pressure); RBBB (right bundle branch block); RBF (renal blood flow); rhRlx or rhRLX (recombinant human relaxin); Rlx or RLX (relaxin); RR (respiratory rate); SBP (systolic blood pressure); SI (stroke index); sMDRD (simplified Modification of Diet in Renal Disease); SQ (subcutaneous SQ); SVR (systemic vascular resistance); T (temperature); VAS (visual analog scale); VF (ventricular fibrillation); VT (ventricular tachycardia); and WHF (worsening heart failure).

Example 1

Study of Recombinant Human Relaxin in Patients with Systemic Sclerosis

Figure 4:
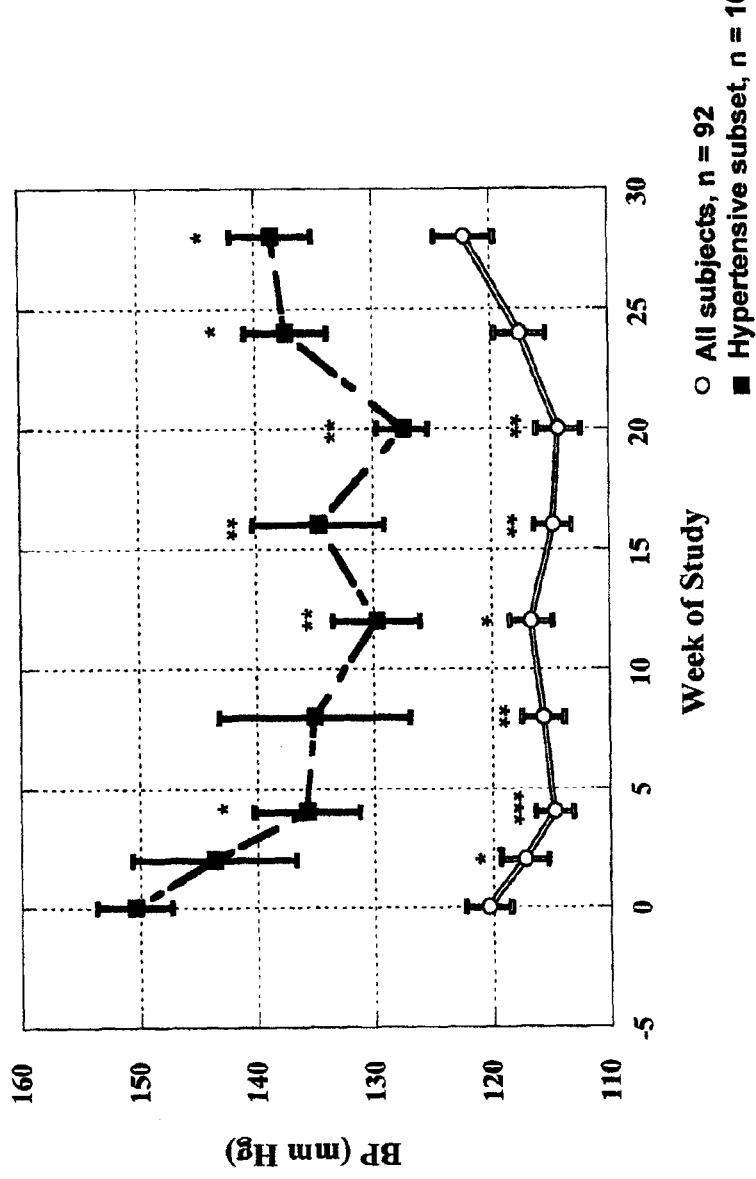
FIG. 4 depicts stable decreases in systolic blood pressure (SBP) in hypertensive and normotensive subjects in the clinical trial of relaxin in patients with systemic sclerosis. Decreases in blood pressure in patients that were hypertensive at study entry was greater than the decreases in blood pressure in patients that were normotensive at study entry. Blood pressure decreases were stable during the six months of continuous dosing. None of the patients developed hypotension during dosing.
Figure 5:
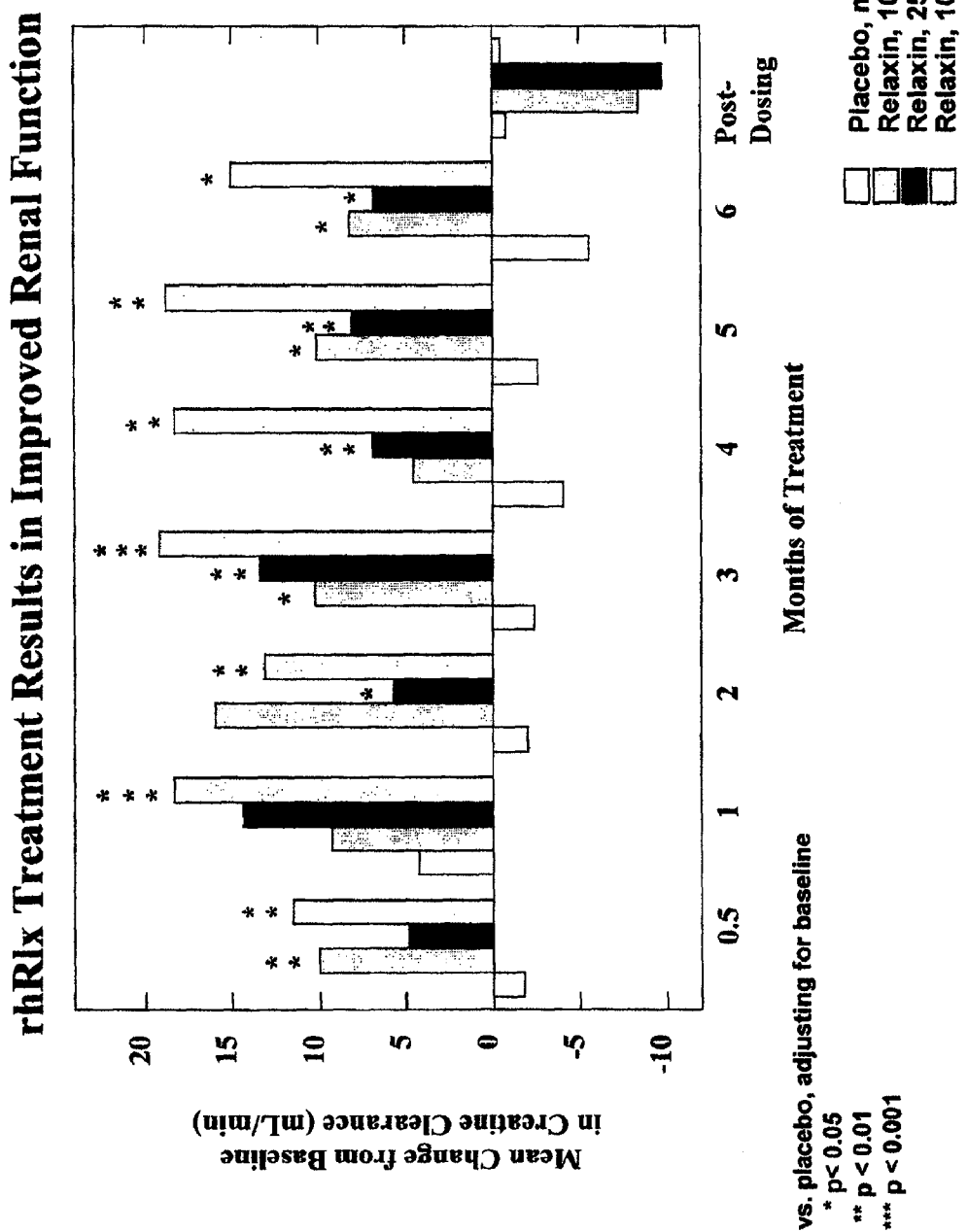
FIG. 5 depicts stable improvement in renal function, measured as predicted creatinine clearance (CrCl), during six months of continuous dosing with relaxin but not with placebo in patients with systemic sclerosis.

Overview. Clinical trials with relaxin have also been conducted on systemic sclerosis patients. 257 human subjects who suffer from systemic sclerosis, a serious fibrotic disease, have been treated with relaxin by continuous and subcutaneous (SQ) infusion for six months. The results, which include extensive and long term safety information, have shown that these patients did not experience any serious hypotensive events as a result of relaxin (FIG. 4), confirming the later CHF findings. The systemic sclerosis trials showed that relaxin administration was associated with stable decreases in blood pressure, with no serious episodes of hypotension, and a statistically significant increase in predicted creatinine clearance (see FIG. 5). These findings support the hypothesis that relaxin administration was associated with balanced systemic and renal vasodilation.

In addition, 570 human subjects have been treated with relaxin in 19 completed trials. These subjects included patients with fibromyalgia, women undergoing egg donation, pregnant women at term, healthy female and male volunteers, healthy adults undergoing orthodontic therapy, and systemic sclerosis patients.

Findings and Conclusion. As described herein, relaxin can be administered safely in subjects with a variety of underlying conditions. In a number of these trials, data suggested that relaxin causes balanced systemic and renal vasodilation.

Example 2

Study of Recombinant Human Relaxin in Patients with Acute Heart Failure

Overview. A multi-center, randomized, double-blind, placebo-controlled clinical trial was conducted to determine the safety and efficacy of recombinant human relaxin (rhRLX) in patients with decompensated congestive heart failure (CHF). The terms decompensated CHF and acute heart failure (AHF) are used interchangeably herein. Patients hospitalized for AHF (defined as including all of dyspnea at rest or with minimal exertion, pulmonary congestion as evidenced by interstitial edema on chest radiograph, and an elevated BNP or NTproBNP), and having an estimated glomerular filtration rate of 30-75 ml/min/1.73 m$^2$ and a SBP>125 mmHg at the time of screening were eligible for randomization within 16 hours from presentation to standard AHF care plus a 48-hour IV infusion of placebo or relaxin (RLX; 10, 30, 100 or 250 mcg/kg/d) and were followed up to day 180. A total of 234 patients were enrolled in the study.

Inclusion Criteria. Men and women aged 18 years or older who were hospitalized for AHF, with preserved or elevated blood pressure and with impaired renal function were eligible for inclusion in the study. AHF was defined by the presence of all of the following at screening: dyspnea at rest or with minimal exertion, pulmonary congestion on chest X-ray and elevated natriuretic peptide levels [brain natriuretic peptide (BNP)≧350 pg/mL or NT-pro-BNP≧1400 pg/mL]. Systolic blood pressure (SBP) had to be >125 mmHg at the time of screening. Impaired renal function was defined as an estimated glomerular filtration rate (eGFR) of between 30 to 75 mL/min/1.73 m$^2$, calculated using the simplified Modification of Diet in Renal Disease (sMDRD) equation (Levey et al., Ann Intern Med, 130:461-470, 1999). Randomization was to occur within 16 hours of initial presentation. Patients had to qualify after receipt of at least 40 mg of intravenous (IV) furosemide (or equivalent dose of alternative loop diuretic).

Exclusion Criteria. Fever (temperature greater than 38° C.); acute contrast-induced nephropathy or recent administration of contrast; ongoing or planned IV treatment with positive inotropic agents, vasopressors, vasodilators (with the exception of IV nitrates infused at a dose≦0.1 mg/kg/h if SBP>150 mmHg), or mechanical support (intra-aortic balloon pump, endotracheal intubation, mechanical ventilation or any ventricular assist device); severe pulmonary disease; significant stenotic cardiac valvular disease; previous organ transplantation or admission for cardiac transplantation; clinical diagnosis of acute coronary syndrome within 45 days prior to screening; major surgery within 30 days of screening; hematocrit less than 25%; major neurologic event within 45 days prior to screening; troponin level at screening greater than 3 times the upper limit of normal; AHF caused by significant arrhythmias; non-cardiac pulmonary edema; or known significant liver disease.

Study Drug. Recombinant human relaxin (rhRlx) was produced using a proprietary process as a single chain precursor, termed Mini-C-prorelaxin, in a recombinant *E. coli* strain. Inclusion bodies containing the precursor were released from the cells by homogenization and recovered by centrifugation. Mini-C-prorelaxin was extracted from the inclusion bodies, refolded with a redox buffer (in order to build the disulfide bridges), and partially purified by silica adsorption and ion exchange chromatography. The leader sequence and the peptide connecting the B-chain to the A-chain were then removed enzymatically. The resulting relaxin was then purified by three successive chromatography steps (ion exchange and reversed phase). Formulation of the product was achieved by ultra- and diafiltration. The rhRlx was formulated as a sterile acetate buffered parenteral solution.

Study Procedures. The study was approved by the relevant ethics committees, institutional review boards and regulatory authorities, and conducted under the International Conference on Harmonization Good Clinical Practice guidelines. All patients provided informed written consent prior to participation. Consenting patients who met all study inclusion and none of the study exclusion criteria were randomized to receive in double blind manner, either IV placebo or relaxin at 10, 30, 100 or 250 mcg/kg/d for 48 hours in addition to standard therapy for AHF at the discretion of the investigator. The placebo used for the study was the same solution as the diluent used to prepare the 100 μg/kg/day dose. The randomization ratio was 3:2:2:2:2, respectively. Relaxin (Corthera, San Mateo, Calif.) was manufactured using recombinant techniques and was identical to the naturally-occurring peptide hormone. By protocol, the study drug infusion was to be terminated if the patient's SBP was reduced to <100 mmHg or by >40 mmHg compared to baseline in two successive measurements, 15 minutes apart. Investigators were not prohibited from utilizing any standard medication thought necessary to treat patients enrolled in the study, including additional vasodilators. Following a 4-hour washout period during which time IV vasodilators, IV pure inotropes and meals were withheld, hemodynamic, renal, and clinical responses to 48 hours of study drug infusion were assessed.

Patient-reported dyspnea was assessed using both a standard 7-point Likert Scale and a standard 100-mm Visual Analog Scale (VAS). Assessments were performed at baseline (VAS only), 6 h, 12 h, 24 h, 48 h after initiation of drug therapy and at Days 3, 4, 5 and 14. Questionnaires were administered in the local language, and investigators received training in the standardized administration of these evaluations. Daily, serial physician-reported assessments of heart failure signs and symptoms were conducted including jugular venous distension, rales, edema, orthopnea, and dyspnea on exertion. In-hospital worsening heart failure was defined as a physician-determined assessment based on worsening symptoms or signs of heart failure and the need for the addition or institution of IV medications or mechanical support to treat AHF. Vital status and rehospitalization information was collected by telephone at Day 30, Day 60 and (vital status only at) Day 180. When the last enrolled patient reached Day 60, telephone contact was made with all patients who were between Day 60 and Day 180 of follow-up to complete the study.

Study Endpoints. As an exploratory, dose-finding study, Pre-RELAX-AHF did not have a single pre-specified primary endpoint. Instead, the overall effect of N relaxin on seven primary treatment efficacy targets was evaluated. 1.) Relief of dyspnea, assessed with two complementary instruments: (a) Change in dyspnea by Likert scale, and (b) Change from baseline by Visual Analog Scale. 2.) In-hospital worsening heart failure (WHF) to Day 5. 3.) Renal impairment, assessed by multiple measures, including: (a) Renal impairment as defined by a ≧25% increase in serum creatinine from baseline to day 5, and (b) Persistent renal impairment as defined by creatinine increase of 0.3 mg/dL or above at both day 5 and 14 from randomization. 4.) Length of initial hospital stay. 5.) Days alive and out-of-hospital to Day 60. 6.) Death due to cardiovascular causes or rehospitalization for heart failure or renal failure to Day 60. 7.) Mortality due to cardiovascular causes to Day 180. In addition, serial assessments of safety were performed including vital signs, physical examinations, adverse events and clinical laboratory evaluations.

Statistical Methods. Data are presented as means with standard deviations unless otherwise specified. Missing data were generally imputed by a last-observation-carried-forward approach. The worst observed dyspnea Likert or VAS score was carried forward from the time of death or worsening heart failure. The area under the curve representing the change in VAS score from baseline through Day 5 was computed by trapezoidal rule. For patients who died during the initial hospitalization, length of stay was imputed as the maximum observed plus 1 day (33 days). Each relaxin group was compared to placebo, without adjustment for multiple comparisons, using logistic regression for the binary outcomes, and the Wilcoxon rank sum test for continuous measures (with the van Elteren extension for the analysis of the length of stay and days alive out of hospital at Day 60), unless otherwise noted. To control for regional variations in this relatively small study, region as a covariate or stratifying variable was prospectively pre-specified in the analyses of treatment effect. Rehospitalization and mortality rates through Day 180 were estimated using Kaplan-Meier (product-limit) methods, and groups compared using the Wald test of the treatment effect from Cox regression models, where time-to-event was censored at last patient contact for patients without the event of interest.

The sample size in this phase 2 study was selected empirically and the study was not prospectively powered for statistical significance of any specific outcome measure. A $p<0.05$ was considered statistically significant, while $0.05 \leq p \leq 0.20$ was considered a trend suggestive of drug effect. The main goals of the study were to identify a dose of relaxin that was associated with multiple trends in the above mentioned primary treatment targets and is not associated with safety concerns, to determine which endpoints demonstrated treatment sensitivity and to document the effect size for further statistical power calculations. The chairperson of an unblinded, independent Data Safety and Monitoring Board reviewed safety data monthly during the conduct of the study.

Study Population. The study enrolled 234 patients at 54 sites in 8 countries (USA, Belgium, Italy, Poland, Israel, Hungary, Romania and Russia) from December, 2007 to August, 2008 with the final study contact in October, 2008. The safety analysis population consists of 230 patients who received any amount of study drug. The efficacy analysis population consists of 229 patients who received study drug, excluding one patient who violated multiple major eligibility criteria. Patients were 70.3±10.5 years old and 56% male, with a screening blood pressure of 147±19 mmHg and extensive co-morbidities (Table 3-1). There were no clinically meaningful or statistically significant differences in characteristics among the five treatment groups. Patients were randomized at a mean of 8.4±5.4 hours from presentation [median 6.6 hours (Q1-Q3: 4.0-13.4)] and were treated with study drug within 1.0±1.8 hours from randomization. Patients in the placebo group received a mean duration of infusion of 44 hours, while those in the relaxin 10, 30, 100 and 250 mcg/kg/d groups received an average of 39, 41, 41 and 42 hours of study drug, respectively. Patients received standard therapy in addition to study drug with 18.0% of the placebo group receiving intravenous nitroglycerin during the first 24 hours, compared to 10.0%, 9.5%, 13.5 and 4.1% in the relaxin 10, 30, 100 and 250 mcg/kg/d groups, respectively.

Dyspnea Responses. Results are presented via the Visual Analog Score (VAS) and the Likert Score. The VAS score measures a characteristic or attitude that ranges across a continuum of values. For example, the amount of discomfort an AHF patient feels ranges across a continuum from none to an extreme amount of discomfort and/or pain including dyspnea, hypertension, high blood pressure, arrhythmia and reduced renal blood flow. From the patient's perspective this spectrum appears continuous, which the VAS captures. Operationally a VAS is usually a horizontal line, 100 mm in length, anchored by word descriptors at each end (e.g., no discomfort on one end and severe discomfort on the other end). The patients marked on the line the point that they felt represented their perception of their current state. The VAS score is determined by measuring in millimeters from the left hand end of the line to the point that the patient marks (Wewers et al., *Research in Nursing and Health* 13:227-236, 1990).

The Likert Score is a unidimensional scaling method known in the art, wherein the set of scale items are rated on a numerical (herein 7-point) Disagree-Agree response scale. Each patient was asked to rate each item on the response scale. The final score for the respondents on the scale is the sum of their ratings for all of the items.

Relaxin-treated patients had rapid, meaningful and sustained dyspnea improvement compared to those in the placebo group. The combined relaxin-treated group had a larger improvement in dyspnea severity compared to placebo as early as 6 hours after initiation of therapy, persisting throughout all time points assessed. The best response to treatment was observed in the patients receiving relaxin at the dose of 30 mcg/kg/d. Moderately or markedly better dyspnea on the Likert Scale at all of the 6 h, 12 h and 24 h assessments occurred in 23.0% of patients in the placebo group compared to 40.5% in the relaxin 30 mcg/kg/d group (p=0.044; Table 3-2). The VAS similarly demonstrated a sustained, positive trend of drug effect on relief of dyspnea. The area under the curve (AUC) for change from baseline to Day 5 in the dyspnea VAS was 1679±2556 mm*hr in the placebo group compared to 2567±2898 mm*hour in the relaxin 30 mcg/kg/d group (p=0.11; Table 3-2), and these observed changes correspond to averages of 14, 21, 22, 21 and 18 mm improvement over the 5 days for the placebo and relaxin 10, 30, 100 and 250 mcg/kg/d groups, respectively. Similar results are evident for the VAS AUC through Day 14 (Table 3-2) where placebo mean was 4622±9003 mm*hr compared to 8214±8712 mm*hour in the relaxin 30 mcg/kg/d group (p=0.053). These changes correspond to averages of 14, 10, 25, 25 and 21 mm over the 14 days, for the respective groups.

Short-term Outcomes. There were consistent trends (p<0.20) in favor of relaxin therapy compared to placebo in multiple in-hospital assessments. In particular, the relaxin dose of 30 mcg/kg/d appeared most effective with supportive trends in the groups receiving 10 and 100 mcg/kg/d. Physician-assessed resolution of jugular venous distension, rales, and edema were all improved in the relaxin 30 mcg/kg/d group compared to placebo at Day 5 (Table 3-3) and at Day 14, associated with trends toward greater decrease in body weight and decreased diuretic use in the relaxin-treated patients. The cumulative incidence of worsening heart failure by day 5 was lower in the relaxin groups compared to placebo (Table 3-2), and the mean length of stay for the index hospitalization tended to be 0.9-1.8 days shorter in the relaxin groups than for placebo (Table 3-2; p=0.18 for relaxin 30 mcg/kg/d vs. placebo group).

Post-Discharge Outcomes. Patients were followed for an average of 122±53 days. A total of 15 patients died by Day 60, and 20 patients by Day 180, 12 for cardiovascular causes. Forty-three patients were rehospitalized by Day 60; 15 due to heart failure and none due to renal failure. Relaxin-treated patients demonstrated trends toward improvement in longer-term clinical outcomes (Table 3-2). At Day 60, the mean number of days alive and out-of-hospital was 44.2±14.2 in the placebo group, while it was approximately 4 days greater in the relaxin-treated patients (p=0.16 for 30 mcg/kg/d vs. placebo group). The Kaplan-Meier estimate of the combined incidence of death due to cardiovascular causes or rehospitalization due to heart failure or renal failure at day 60 was 17.2% in the group receiving placebo, but much less in the relaxin-treated patients with an estimated 87% hazard reduction in the relaxin 30 mcg/kg/d group (p=0.053 vs. placebo). Similar findings were evident when all-cause mortality was included (Table 3-2). The Kaplan-Meier estimate of Day 180 cardiovascular mortality was 14.3% in the placebo group, but was considerably less in the relaxin-treated groups (p=0.046 for relaxin 30 mcg/kg/d compared to placebo by Fisher's exact test of the incidence densities). The corresponding Kaplan-Meier estimates for all-cause mortality demonstrated similar trends.

Safety Endpoints. Adverse events and serious adverse events were evenly distributed across study groups and represented the natural history of patients hospitalized with AHF (Table 3-4). There were no individual or pattern of adverse events suggesting a deleterious study drug effect.

Figure 21:
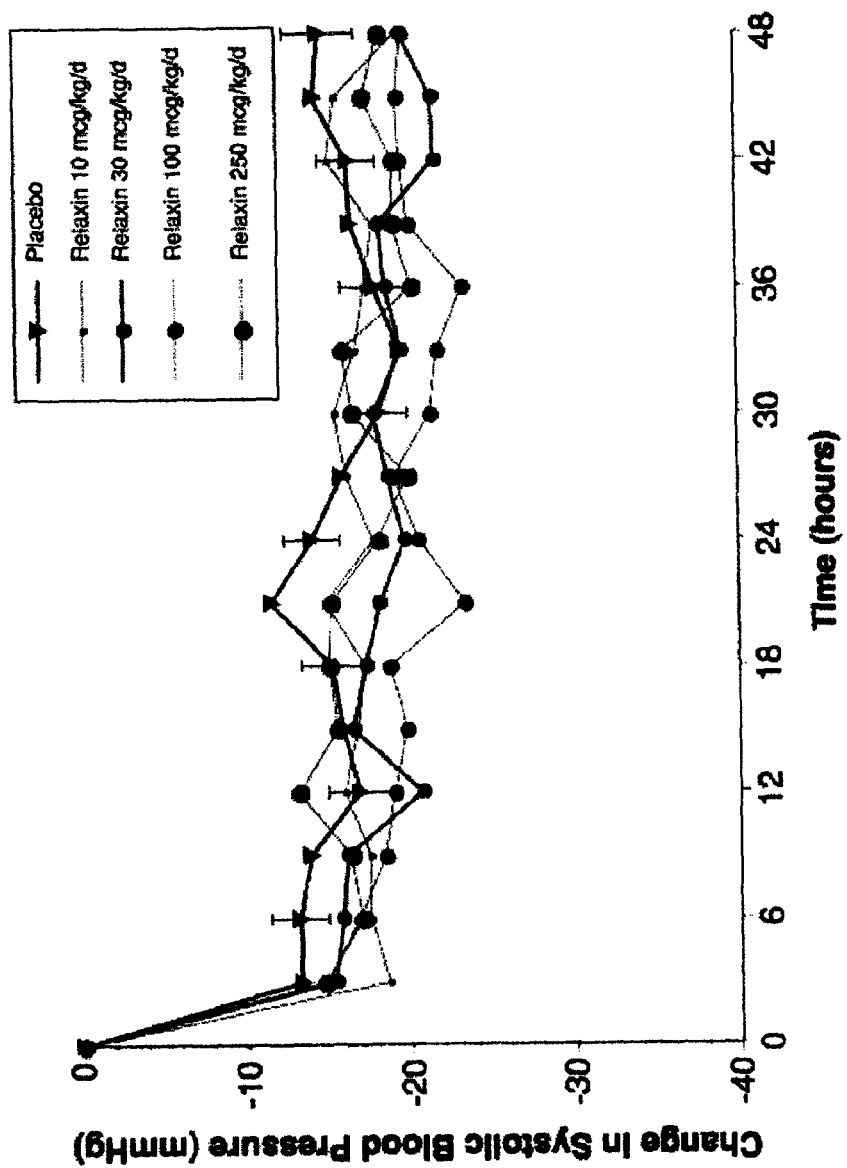
FIG. 21 shows the mean change in systolic blood pressure (mmHg) from baseline in relaxin and placebo treated AHF patients during infusion. The average decrease in blood pressure over all time points did not differ between any of the treatment groups and the placebo groups.
Figure 22:
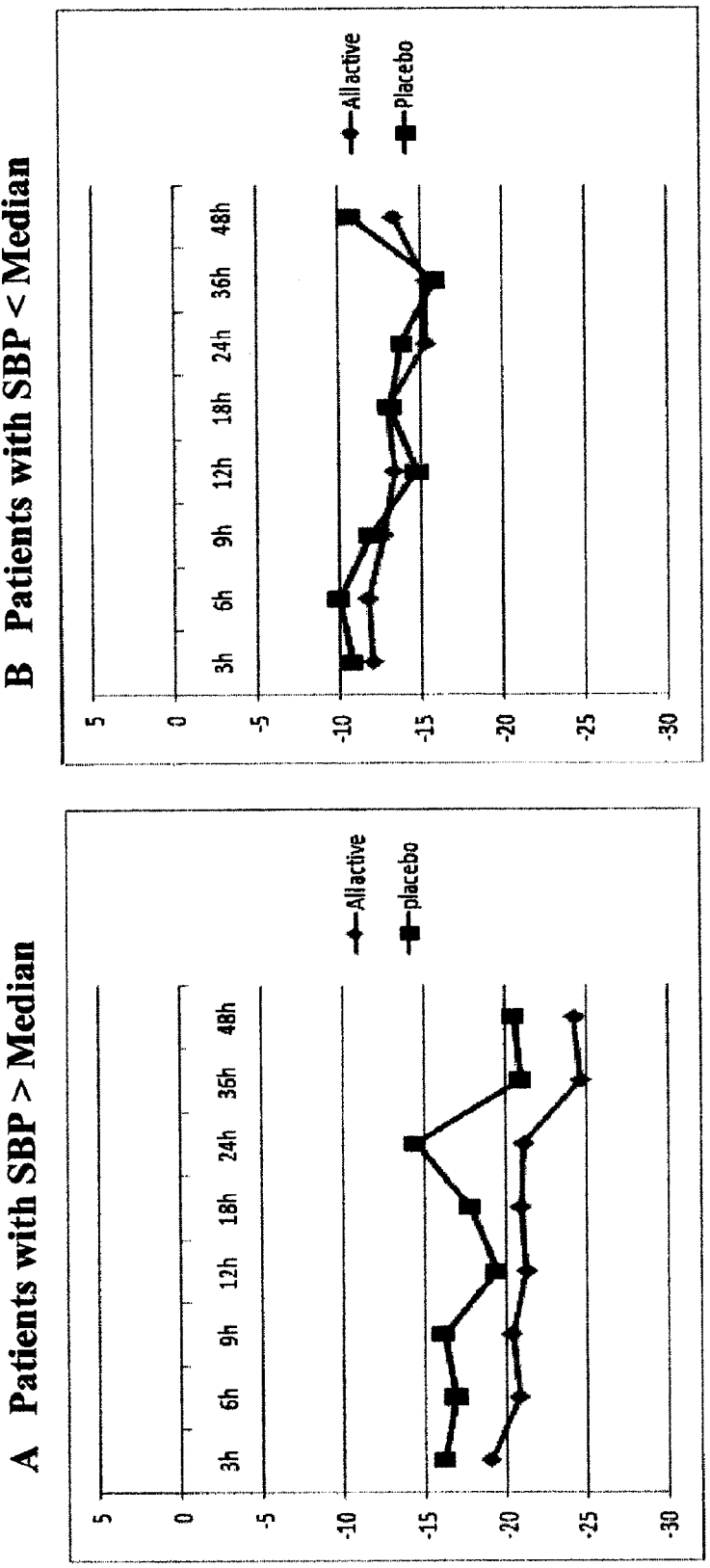
FIGS. 22A and 22B show that relaxin treatment reduces blood pressure in AHF patients in the study having a baseline systolic blood pressure (SBP) above the median of the group, but not in AHF patients having a baseline SBP below the median of the group. This indicates that relaxin treatment preferentially vasodilates vasoconstricted arteries, and does not cause deleterious hypotension when administered to normotensive patients.
Figure 23:
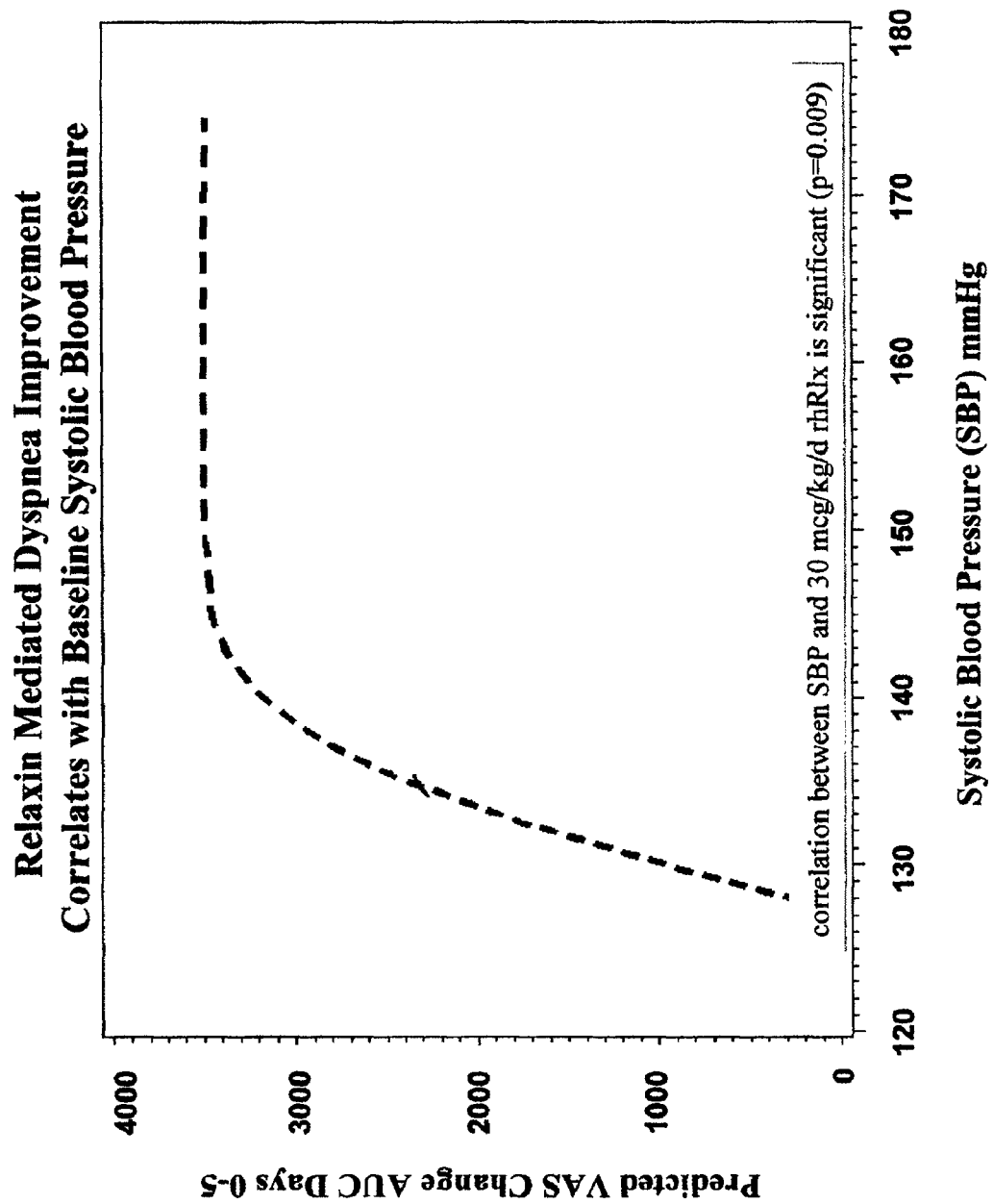
FIG. 23 shows that relaxin mediated improvement in dyspnea is correlated with a normal or elevated baseline systolic blood pressure (SBP).

Relaxin has known vasodilating activity and consequently, changes in blood pressure were carefully monitored. During the 48-hour infusion period, the placebo group had a 12-20 mmHg decrease from baseline in systolic blood pressure (SBP) and the relaxin-treated patients had similar reductions (FIG. 21). The average decrease in blood pressure over all time points did not differ between any of the treatment groups and the placebo group by repeated measures ANOVA (p-values for the average change in SBP comparing 10, 30, 100, and 250 mcg/kg/day with placebo were 0.41, 0.16, 0.13, and 0.32, respectively), although there was a trend in the 30 and 100 mcg/kg/d groups with a mean decrease of 3-4 mmHg compared to placebo. There were 36 adverse events of hypotension and/or decreases in SBP which met protocol-specified study drug stopping rules, two of which were serious adverse events (both in the relaxin 250 mcg/kg/d group). Protocol-specified study drug discontinuation due to blood pressure reduction occurred in 10.9% of patients across all groups, and was more frequent in relaxin-treated groups (20.0%, 9.5%, 7.9% and 16.3% with relaxin 10, 30, 100 and 250 mcg/kg/d, respectively) compared to placebo (3.3%) with no apparent dose-response. Most blood pressure reductions occurred during the first 6-12 hours of therapy. In no cases did the trough SBP fall below 80 mmHg. After discontinuation of study drug, SBP stabilized or rose in most of these patients with no therapy (1 of 2 placebo patients with SBP reductions; 18 of 23 relaxin-treated patients). In the placebo group, 1 patient (1.6%) received intravenous fluids for hypotension, while 5 patients from the four relaxin-treated groups (3.0%) received intravenous fluids and one asymptomatic patient also received dobutamine in the relaxin 250 mcg/kg/d group. None of the patients in the 10 or 30 mcg/kg/d groups required treatment of blood pressure reduction.

There were no differences in the incidence of renal failure reported as a serious adverse event among the study groups (Table 3-4). At Day 14, mean changes in creatinine from baseline were 0.08±0.46, 0.07±0.24, 0.13±0.49, 0.08±0.39 and 0.10±0.39 mg/dL (p-value for each group vs. placebo≧0.97). The proportion of patients at Day 14 with an increase of 0.3 mg/dL or more was 16.7%, 19.4%, 26.3%, 24.2% and 37.2% (p=0.03 for 250 mcg/kg/d vs. placebo). Persistent renal impairment (0.3 mg/dL or greater increase in creatinine at both Day 5 and 14) also trended to being greater in patients receiving relaxin 250 mcg/kg/d (p=0.19 vs. placebo).

As with many vasodilators, there was a transient and clinically insignificant decrease in hematocrit in all active treatment groups that occurred during study drug administration (change from baseline in mean hematocrit at 48 hours: +0.42% in placebo group and 0.57%, 1.45%, 0.25%, 0.64% in relaxin 10, 30, 100 and 250 mcg/kg/d groups, respectively; p=0.019 vs. placebo for relaxin 30 mcg/kg/d group), resolving by Day 5. There were no other clinical laboratory changes of note during the study.

TABLE 3-1

Baseline Patient Characteristics

| Group | Placebo | Relaxin (mcg/kg/d) | | | |
|---|---|---|---|---|---|
| | | 10 | 30 | 100 | 250 |
| Number of Subjects in Efficacy Analysis | 61 | 40 | 42 | 37 | 49 |
| Men, % | 65.6 | 52.5 | 42.9 | 51.4 | 61.2 |
| Age, yr | 68.4 (9.9) | 72.2 (11.0) | 71.6 (9.2) | 69.2 (11.6) | 70.7 (11.0) |
| Weight, kg | 80.7 (15.6) | 80.2 (16.9) | 79.9 (13.0) | 84.5 (25.0) | 80.2 (16.7) |
| Ischemic heart disease, % | 67.2 | 62.5 | 78.6 | 64.9 | 73.5 |
| Hypertension history, % | 82.0 | 87.5 | 90.5 | 81.1 | 87.8 |
| Diabetes history, % | 49.2 | 32.5 | 52.4 | 32.4 | 40.8 |
| Mitral regurgitation, % | 23.0 | 30.0 | 31.0 | 32.4 | 36.7 |
| Atrial fibrillation/flutter, % | 42.6 | 60.0 | 42.9 | 56.8 | 38.8 |
| Ejection fraction <40%, % | 44.2 | 48.4 | 53.6 | 68.0 | 55.6 |
| Hospitalized for AHF in prior year, % | 29.5 | 32.5 | 38.1 | 43.2 | 30.6 |
| NYHA class, % | | | | | |
| I | 3.3 | 0.0 | 0.0 | 0.0 | 4.1 |
| II | 26.2 | 35.0 | 14.3 | 21.6 | 10.2 |
| III | 37.7 | 42.5 | 40.5 | 35.1 | 44.9 |
| IV | 19.7 | 12.5 | 33.3 | 37.8 | 28.6 |
| NT-pro-BNP >2000 pg/mL, % | 75.4 | 70.0 | 83.3 | 70.3 | 71.4 |
| Troponin ≧0.1 ng/mL and <3 × ULN, % | 23.3 | 18.4 | 10.3 | 13.9 | 16.7 |
| SBP at screening, mmHg | 147.5 (20.3) | 145.4 (16.0) | 150.3 (19.5) | 146.5 (18.7) | 145.5 (20.5) |
| eGFR | 53.9 (16.8) | 56.5 (15.8) | 50.6 (14.1) | 53.4 (22.0) | 53.4 (15.2) |
| Serum creatinine, mg/dL | 1.4 (0.5) | 1.2 (0.5) | 1.3 (0.4) | 1.3 (0.4) | 1.3 (0.5) |
| BUN, mg/dL | 28.3 (12.4) | 25.2 (11.7) | 28.2 (10.7) | 25.7 (10.7) | 26.7 (10.8) |
| Sodium, meq/L | 140.7 (3.4) | 139.9 (3.2) | 140.4 (4.0) | 140.8 (4.1) | 139.9 (4.9) |
| Time from presentation to randomization, hr [median] | 9.0 (5.7) [6.4] | 7.5 (4.8) [6.0] | 7.6 (4.8) [6.1] | 9.0 (5.5) [7.5] | 8.4 (5.7) [6.6] |
| Time from randomization to drug administration, hr | 1.0 (1.1) | 0.9 (1.2) | 0.6 (0.5) | 0.7 (0.4) | 1.6 (3.6) |
| Medications 1 month prior to presentation, % | | | | | |
| ACE inhibitor or ARB | 75.4 | 55.0 | 73.8 | 75.7 | 69.4 |
| Beta-blocker | 60.7 | 67.5 | 69.0 | 59.5 | 63.3 |
| Aldosterone inhibitor | 27.9 | 27.5 | 28.6 | 29.7 | 38.8 |

Results expressed as mean (SD), unless otherwise noted. NYHA (New York Heart Association) class when last in stable condition;
eGFR by sMDRD, ml/min/1.73 m$^2$;
ULN, upper limit of normal.

TABLE 3-2

Effect Of Relaxin On Primary Treatment Targets

| | Placebo | Relaxin (mcg/kg/d) | | | |
|---|---|---|---|---|---|
| | | 10 | 30 | 100 | 250 |
| Number of Subjects in Efficacy Analysis | 61 | 40 | 42 | 37 | 49 |
| Short-term Outcomes: | | | | | |
| % moderately/markedly better dyspnea at 6, 12 and 24 hrs (Likert) | 23.0% | 27.5% p = 0.54 | 40.5% p = 0.044 | 13.5% p = 0.28 | 22.4% p = 0.86 |
| Dyspnea AUC Change from baseline to Day 5 (VAS; mm * hr) | 1679 ± 2556 | 2500 ± 2908 p = 0.15 | 2567 ± 2898 p = 0.11 | 2486 ± 2865 p = 0.16 | 2155 ± 2338 p = 0.31 |

TABLE 3-2-continued

Effect Of Relaxin On Primary Treatment Targets

| | Placebo | Relaxin (mcg/kg/d) 10 | 30 | 100 | 250 |
|---|---|---|---|---|---|
| Dyspnea AUC Change from baseline to Day 14 (VAS; mm * hr) | 4621 ± 9003 | 6366 ± 10078 p = 0.37 | 8214 ± 8712 p = 0.053 | 8227 ± 9707 p = 0.064 | 6856 ± 7923 p = 0.16 |
| Worsening HF through Day 5 (%)* | 21.3% | 20.0% p = 0.75 | 11.9% p = 0.29 | 13.5% p = 0.40 | 10.2% p = 0.15 |
| Length of Hospital Stay (days) | 12.0 ± 7.3 | 10.9 ± 8.5 p = 0.36 | 10.2 ± 6.1 p = 0.18 | 11.1 ± 6.6 p = 0.75 | 10.6 ± 6.6 p = 0.20 |
| Day 60 Outcomes | | | | | |
| Days alive out of hospital | 44.2 ± 14.2 | 47.0 ± 13.0 p = 0.40 | 47.9 ± 10.1 p = 0.16 | 48 ± 10.1 p = 0.40 | 47.6 ± 12.0 p = 0.048 |
| Cardiovascular death or Rehospitalization (KM %; [HR (95% CI)])† | 17.2% | 10.1% [0.55 (0.17-1.77)] p = 0.32 | 2.6% [0.13 (0.02-1.03)] p = 0.053 | 8.4% [0.46 (0.13-1.66)] p = 0.23 | 6.2% [0.32 (0.09-1.17)] p = 0.085 |
| All-cause death or Rehospitalization (KM %; [HR (95% CI)])† | 18.6% | 12.5% [0.63 (0.22-1.81)] p = 0.39 | 7.6% [0.36 (0.10-1.29)] p = 0.12 | 10.9% [0.56 (0.18-1.76)] p = 0.32 | 8.3% [0.41 (0.13-1.28)] p = 0.12 |
| Day 180 Outcomes | | | | | |
| Cardiovascular death (KM %; [HR (95% CI)])**, † | 14.3% | 2.5% [0.19 (0.00-1.49)] p = 0.15 | 0.0% [0.00 (0.00-0.98)] p = 0.046 | 2.9% [0.23 (0.01-1.79)] p = 0.17 | 6.2% [0.56 (0.09-2.47)] p = 0.53 |
| All-cause death (KM %; [HR (95% CI)])† | 15.8% | 5.0% [0.34 (0.07-1.62)] p = 0.18 | 8.7% [0.54 (0.14-2.03)] p = 0.36 | 5.5% [0.41 (0.09-1.91)] p = 0.25 | 10.7% [0.08 (0.26-2.47)] p = 0.70 |

Results expressed as mean ± SD;
*For Wilcoxon rank sum test of time to worsening HF through Day 5; subjects without worsening HF were assigned a value of 6 days;
**by Fisher's exact test comparing incidence densities;
†Analyses performed on safety population which included one additional patient (n = 38) in the 100 mcg/kg/d group. Rehospitalization included hospitalization for heart failure or renal failure;
KM, Kaplan-Meier estimates of event rate at specified time period;
HR, hazard ratio.

TABLE 3-3

Improvement in Signs of Heart Failure

| | Placebo | Relaxin (mcg/kg/d) 10 | 30 | 100 | 250 |
|---|---|---|---|---|---|
| Number of Subjects in Efficacy population | 61 | 40 | 42 | 37 | 49 |
| % of subjects at Day 5 with: | | | | | |
| No edema | 47.5 | 55.0 | 64.3† | 51.4* | 61.2† |
| No rales | 67.2 | 65.0 | 76.2 | 70.3 | 71.4 |
| JVP <6 cm | 67.2 | 72.5 | 78.6 | 73.0 | 76.6+ |
| Median total IV diuretic dose from randomization to Day 5 [mg; median (Q1-Q3)] | 170 (80-300) | 100 (40-200) | 100 (60-360) | 90+ (40-200) | 140 (60-340) |
| Median change in body weight from baseline to Day 14 [kg; median (Q1; Q3)] | −2.0 (−4.2-0.0) | −2.0 (−4.5-0.0) | −3.0 (−5.0-0.0) | −2.5 (−4.7-0.8) | −2.0 (−4.0-0.0) |

†p < 0.001;
*0.001 ≦ p ≦ 0.05; +, 0.05 < p ≦ 0.20 for Wilcoxon rank sum test of change in score from baseline (for signs), van Elteren extension of the Wilcoxon test (for diuretic dose), or ANOVA (for body weight). JVP, jugular venous pressure.

TABLE 3-4

Selected Adverse Events

| Group | Placebo | Relaxin (mcg/kg/d) 10 | 30 | 100 | 250 |
|---|---|---|---|---|---|
| Number of Subjects in Safety Groups | 61 | 40 | 42 | 38 | 49 |

TABLE 3-4-continued

Selected Adverse Events

| Group | Placebo | Relaxin (mcg/kg/d) 10 | 30 | 100 | 250 |
|---|---|---|---|---|---|
| Serious adverse events (SAEs) to Day 30 | | | | | |
| Patients with any SAEs to Day 30, n (%) | 10 (16.4%) | 7 (17.5%) | 7 (16.7%) | 3 (7.9%) | 8 (16.3%) |
| Total number of SAEs | 13 | 8 | 12 | 3 | 11 |
| Cardiac failure, n (%) | 5 (8.2%) | 2 (5.0%) | 1 (2.4%) | 0 | 2 (6.1%) |
| Ventricular fibrillation, n (%) | 0 | 1 (2.5%) | 0 | 0 | 0 |
| Noncardiac chest pain, n (%) | 0 | 2 (5.0%) | 0 | 0 | 1 (2.0%) |
| Hypotension, n (%) | 0 | 0 | 0 | 0 | 2 (4.1%) |
| Acute respiratory failure, n (%) | 0 | 0 | 0 | 1 (2.6%) | 0 |
| Pneumonia, n (%) | 1 (1.6%) | 0 | 3 (7.1%) | 0 | 0 |
| Bronchitis, n (%) | 0 | 0 | 1 (2.4%) | 0 | 1 (2.0%) |
| Urinary tract infection, n (%) | 0 | 0 | 1 (2.4%) | 0 | 1 (2.0%) |
| Cerebrovascular accident, n (%) | 1 (1.6%) | 0 | 2 (4.8%) | 0 | 0 |
| Renal failure, n (%) | 1 (1.6%) | 0 | 1 (2.4%) | 0 | 0 |
| Urinary retention, n (%) | 0 | 0 | 0 | 2 (5.3%) | 0 |
| Adverse events to Day 30 | | | | | |
| Patients with any adverse events to Day 30, n (%) | 45 (73.8%) | 32 (80.0%) | 25 (59.5%) | 24 (63.2%) | 25 (51.0%) |
| Patients with any AE from Day 15 to Day 30, n (%) | 6 (9.8%) | 4 (10.0%) | 5 (11.9%) | 2 (5.3%) | 3 (6.1%) |
| Renal impairment | | | | | |
| Patients with ≧25% increase in creatinine at Day 5 | 8 (13.3%) | 4 (10.0%) | 9 (22.0%) | 11 (29.7%)* | 12 (25.5%) |
| Patients with ≧0.3 mg/dL increase in creatinine at Day 5 | 11 (19.3%) | 3 (7.9%) | 7 (18.9%) | 9 (26.5%) | 10 (22.7%) |
| Patients with ≧0.3 mg/dL increase in creatinine at Day 5 and Day 14 | 4 (6.8%) | 3 (7.5%) | 3 (7.3%) | 4 (10.8%) | 7 (15.2%)+ |

*P < 0.05;
+p < 0.20.

Figure 12:
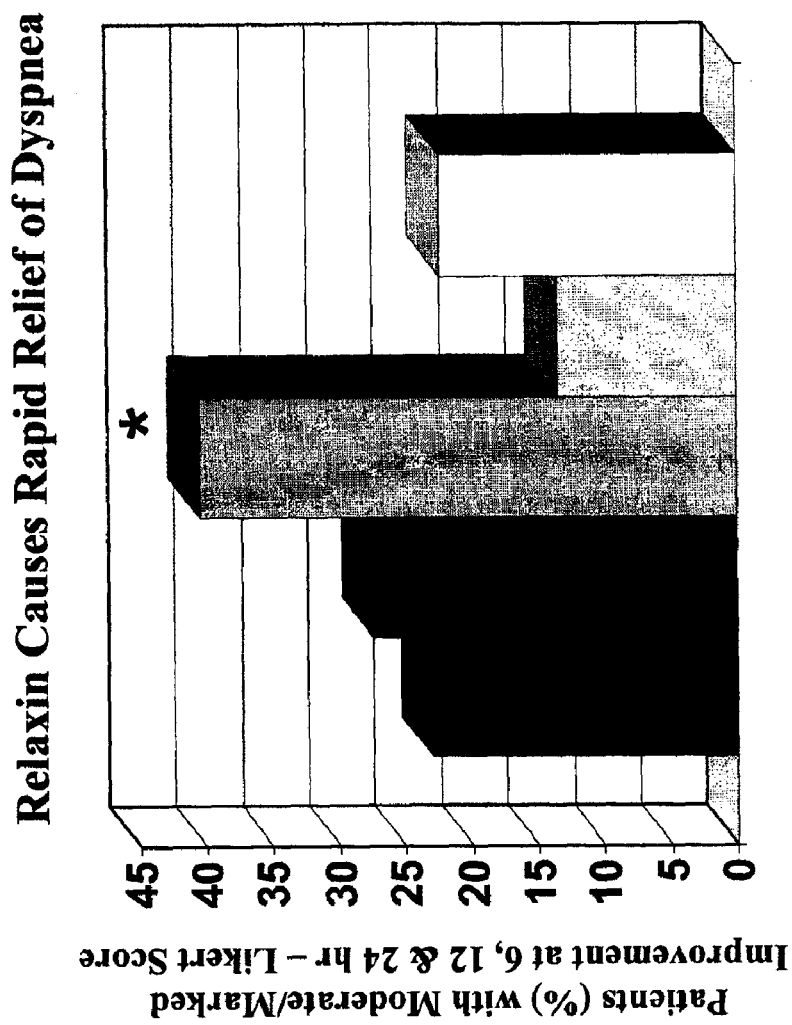
FIG. 12 depicts a graph showing that relaxin treatment caused rapid relief of dyspnea in AHF patients within 6, 12 and 24 hours of administration. In particular administration of 30 µ/kg/day of rhRlx resulted in a statistically significant improvement in dyspnea.
Figure 13:
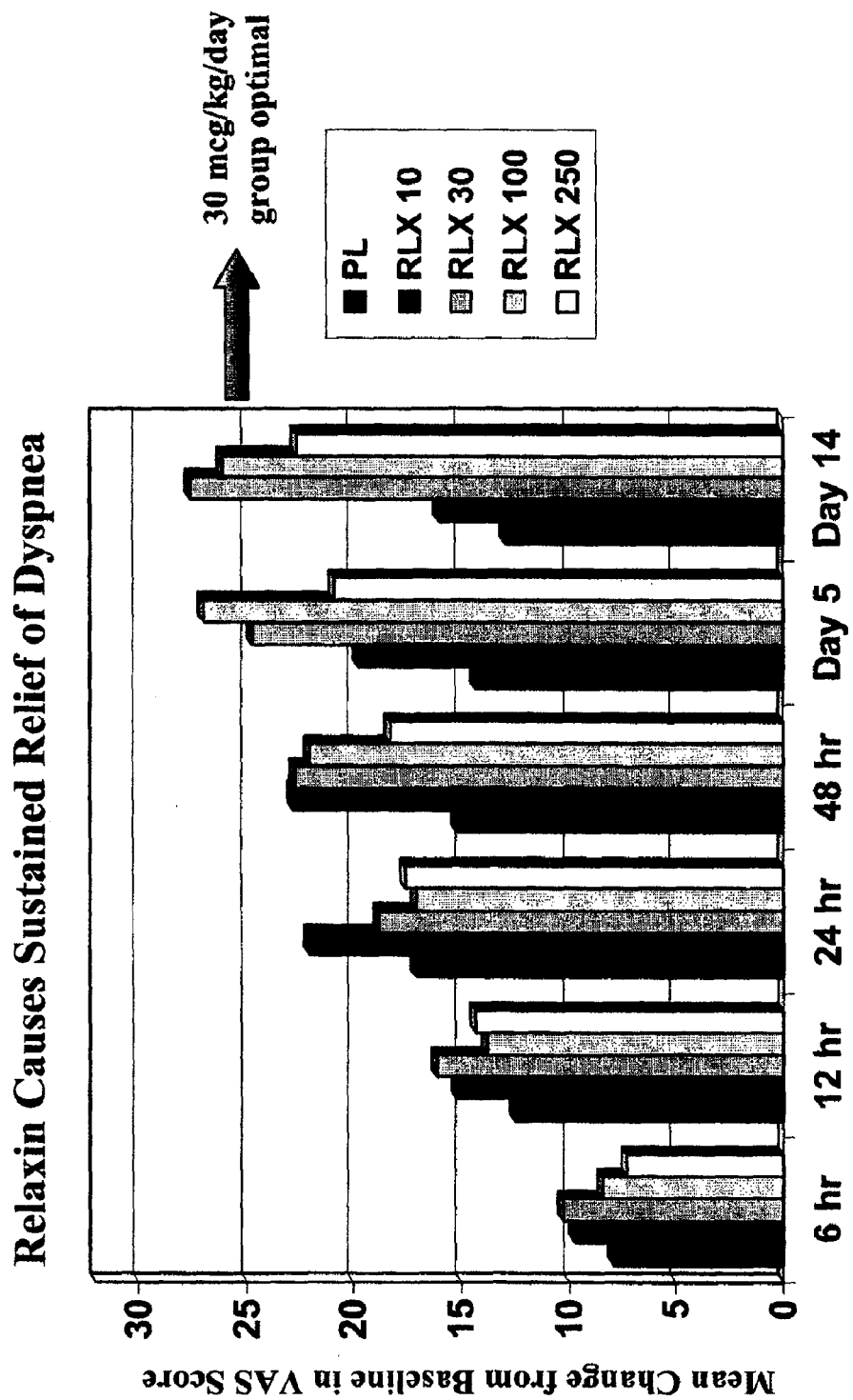
FIG. 13 depicts a graph showing that relaxin treatment caused sustained relief of dyspnea in AHF patients that lasted up to 14 days (i.e., the maximum period measured).
Figure 14:
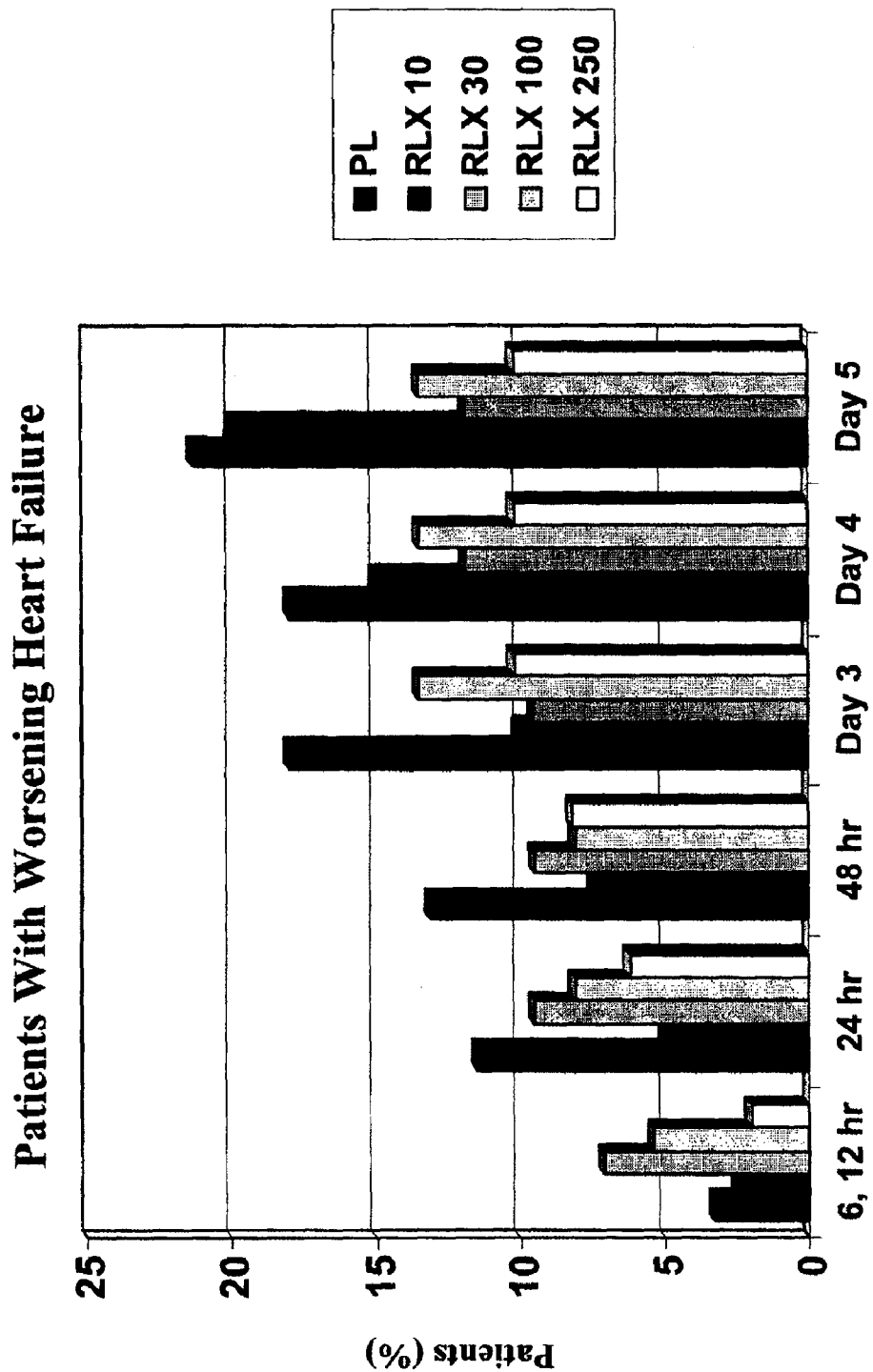
FIG. 14 depicts a graph showing that the placebo-treated patient group experienced a worsening of acute heart failure compared to the relaxin-treated groups.
Figure 15:
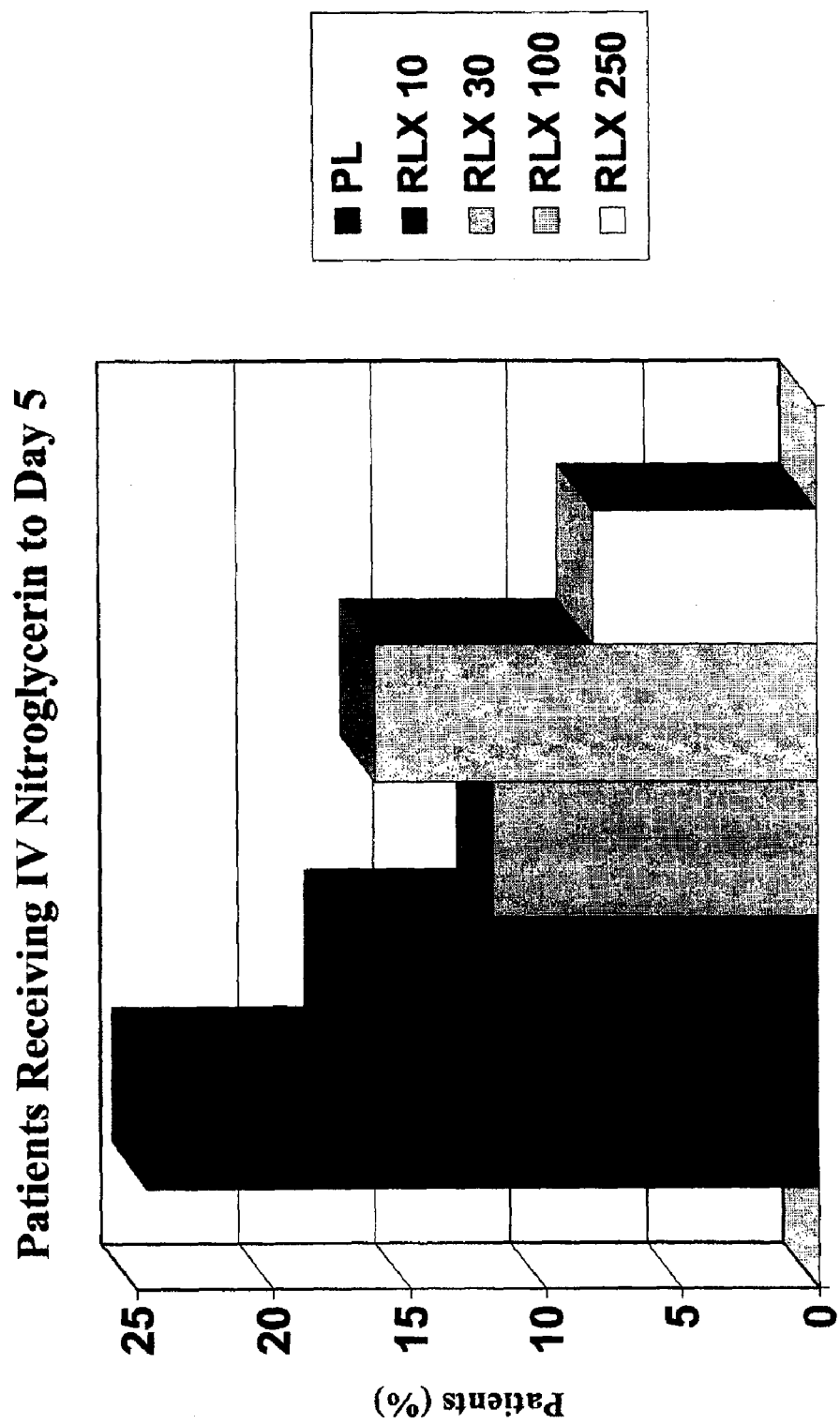
FIG. 15 shows that more AHF patients in the placebo group received N nitroglycerin by study day 5, than AHF patients in the relaxin-treated groups. Nitroglycerin administration is a hospital measure in the clinical study described herein.
Figure 16:
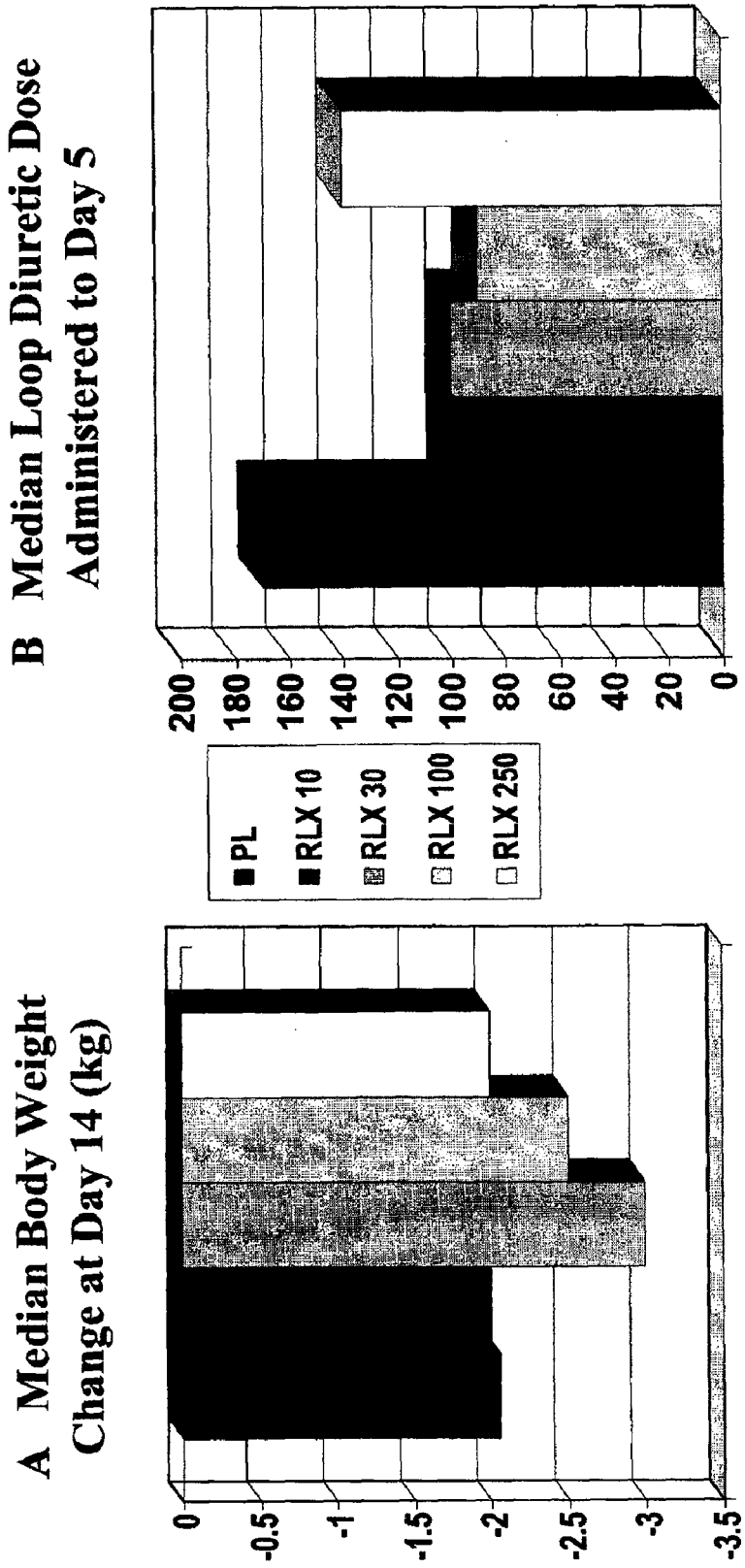
FIGS. 16A and 16B respectively show that AHF patients in several of the relaxin treated groups had a greater reduction in body weight reflecting diuresis, while receiving less diuretic (e.g., hospital measures and endpoints). This outcome indicates that relaxin treatment resulted in renal vasodilation.
Figure 17:
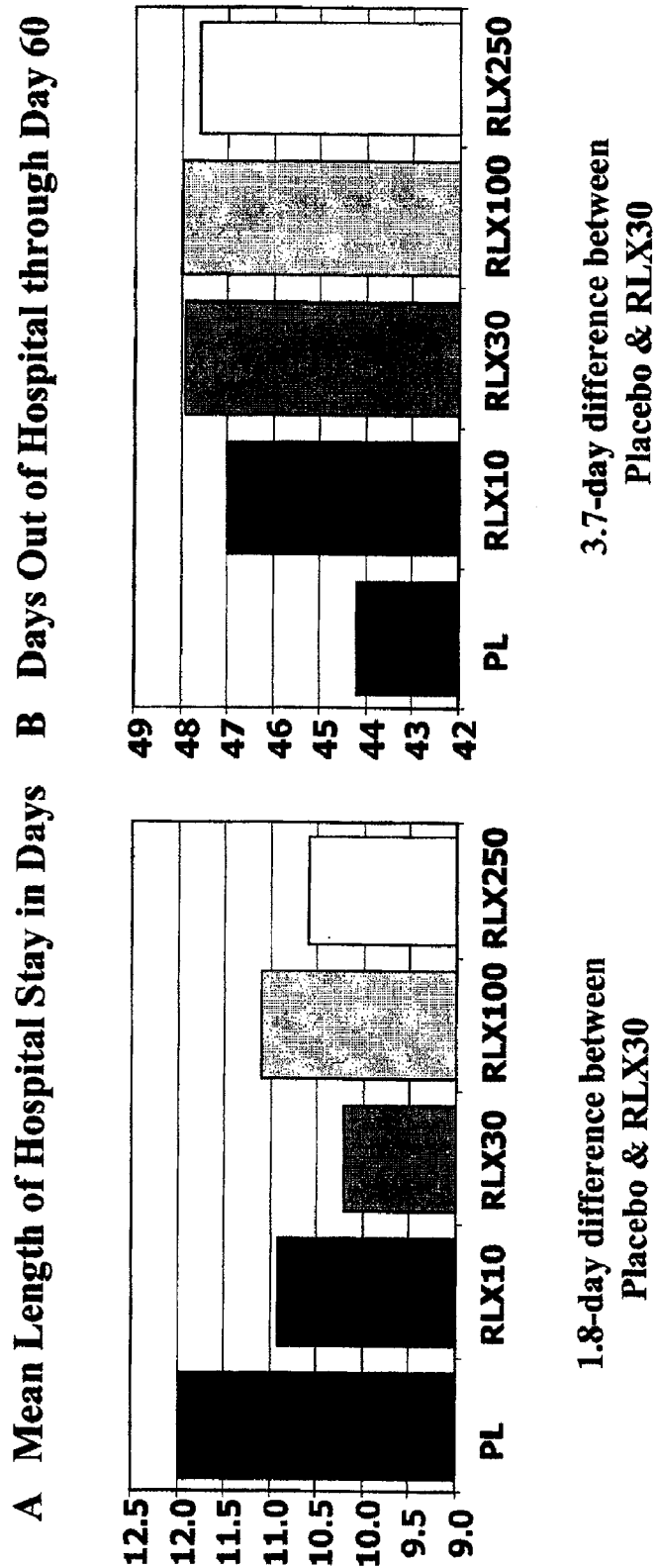
FIGS. 17A and 17B respectively show that relaxin treatment was associated with a reduction in the length of hospital stay and an increase in longevity out of the hospital.
Figure 18:
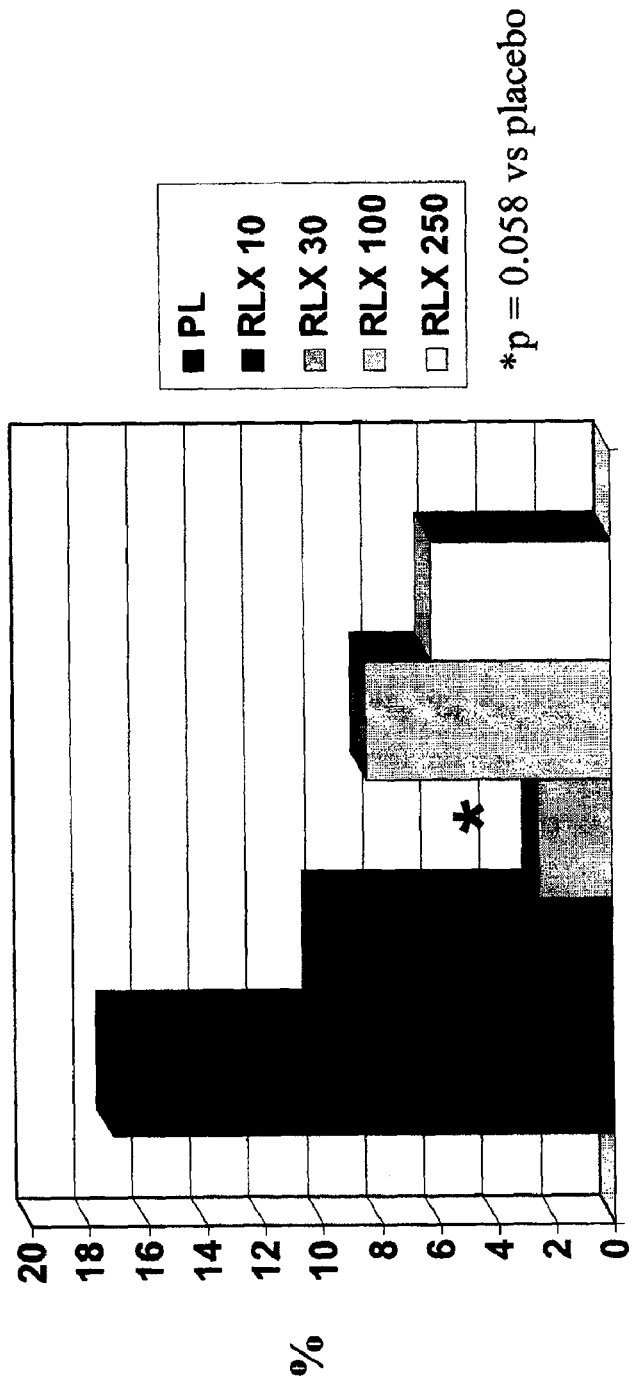
FIG. 18 depicts a graph shows the percent cardiovascular death (CV) or re-hospitalization on day 60 in AHF patients treated with relaxin as compared to AHF patients treated with placebo. A lower proportion of patients treated with relaxin had died as a result of worsened cardiovascular disease. Likewise a lower proportion of patients treated with relaxin required re-hospitalization.
Figure 19:
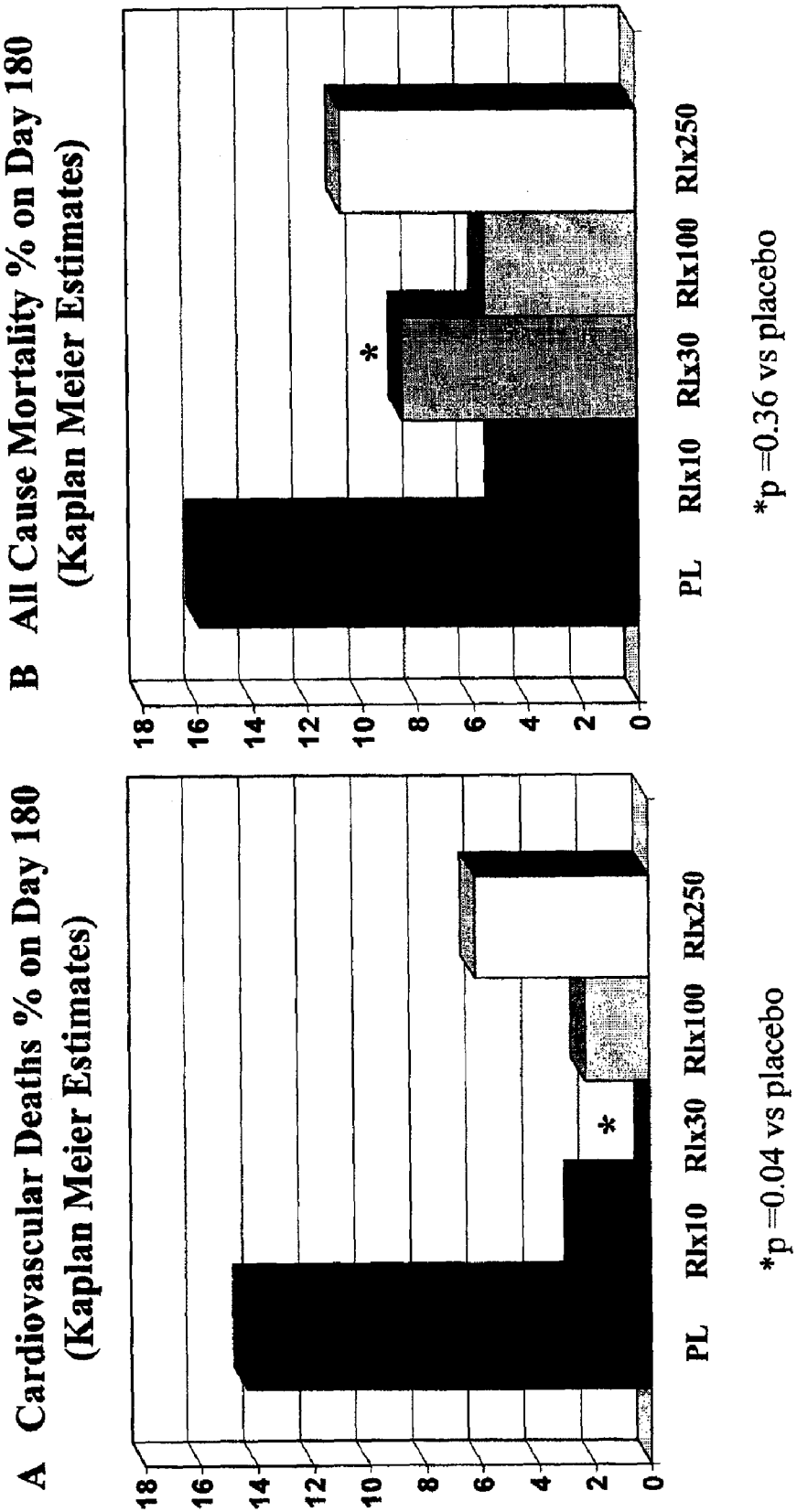
FIGS. 19A and 19B respectively show the percent cardiovascular (CV) death and all cause mortality in relaxin-treated AHF patients as compared to placebo-treated AHF patients within a 180 day time frame post treatment. As illustrated in the graphs, relaxin-treated patients fared dramatically better with a significant reduction in both the number of cardiovascular related deaths and in death by all causes as compared to patients receiving placebo.

Findings. As shown in FIGS. 6-11 of the interim analysis and FIGS. 12 and 13 of the final analysis, relaxin treatment resulted in measurable improvements in dyspnea. Although all patients received benefit from relaxin treatment, patients with NT-pro-BNP of greater than 2000, patients with systolic blood pressure greater than the median, and patients with creatinine clearance of less than the median, received the greatest benefit (FIGS. 7-11). Surprisingly, a low dosage of 30 μg/kg/day of relaxin provided the most rapid and marked relief of dyspnea as measured using a 7-point Likert score (FIG. 12). Across all relaxin-treated groups, the trends in VAS measurements (FIG. 13) of dyspnea also unexpectedly indicated that the beneficial effect of relaxin treatment was persistent (e.g., through day 14). Both instruments (VAS and Likert) are accepted measures of dyspnea in heart failure patients, although the categorical scale (Likert) appears more sensitive to early changes, while the ordinal scale (VAS) appears more sensitive to late changes.

Figure 20:
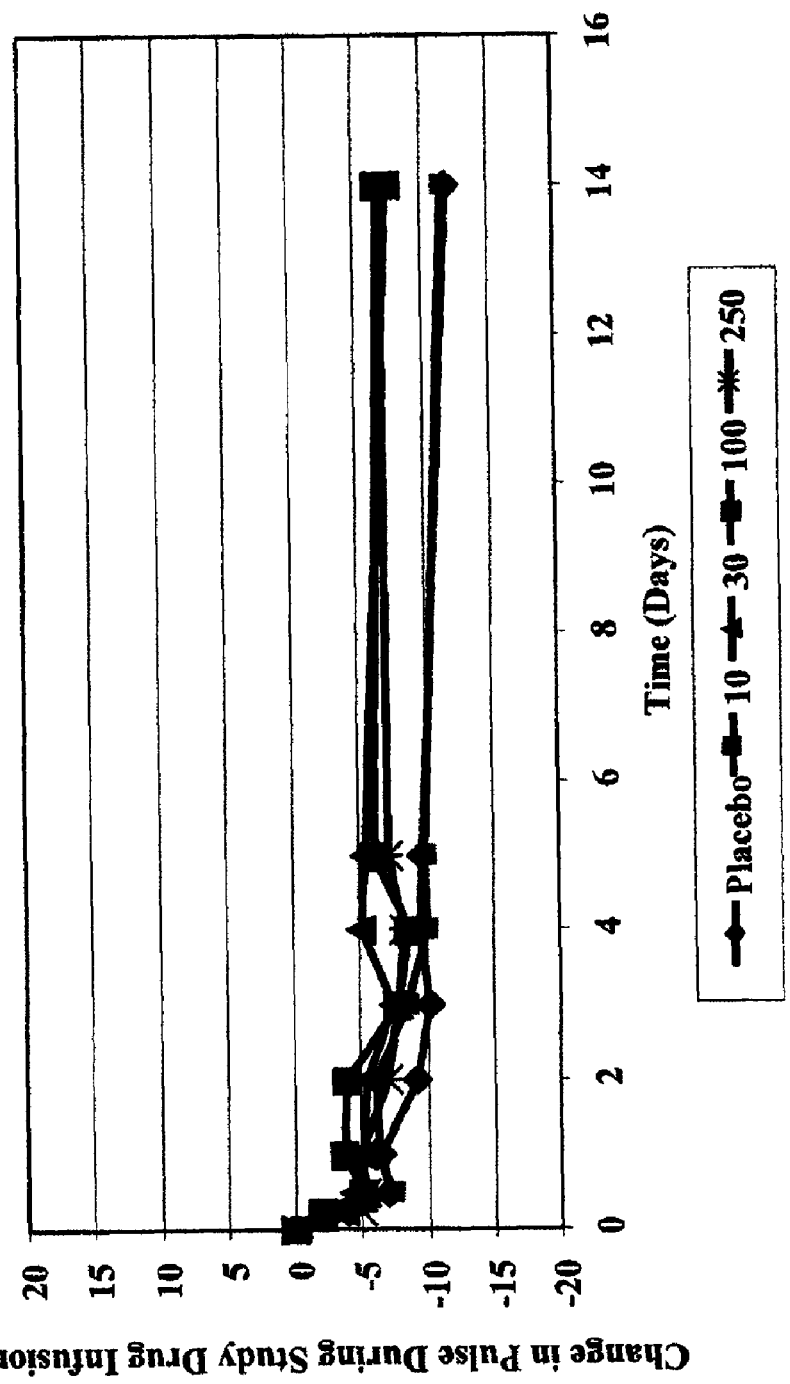
FIG. 20 shows the mean change in pulse from baseline in relaxin and placebo treated AHF patients through day 14. The differences between the groups are not significant, with all groups seeing a small reduction in pulse after hospital admission, indicating that relaxin treatment was not chronotropic.

The beneficial effect of relaxin included a reduction of acute cardiac decompensation events including not only dyspnea, but extra body weight due to retention of fluids, length of hospital stay, likelihood of hospital re-admission, need for loop diuretics, need for intravenous (IV) nitroglycerin, and an incidence of worsening heart failure (FIGS. 14-19). Specifically a decrease in the incidence of worsening of heart failure compared to placebo was found to be clinically relevant, while shorter hospital stays and a reduced incidence of re-hospitalization promises a positive impact in pharma-economics. In addition, there were no apparent adverse effects on renal function, and there were no safety or tolerability issues. Noteworthy in their absences were untoward heart rate elevations and symptomatic hypotension in relaxin-treated patients (see, FIGS. 20 and 21), which one of skill in the art may have expected of a chronotropic agent or an indiscriminate vasodilator.

Conclusion. This is the first prospective study to examine the effects of IV relaxin in patients with acute heart failure (AHF), presenting with systolic blood pressure greater than 125 mmHg and mild to moderate renal impairment. Treatment with relaxin was associated with significant improvement in dyspnea that was substantial in magnitude, rapid in onset (within 6 hours), and sustained to 14 days. Treatment with relaxin was associated with trends toward improvement in other important clinical endpoints, including signs of heart failure, in-hospital worsening of heart failure, length of stay, cardiovascular death or rehospitalization at 60 days, and 180-day cardiovascular mortality. These effects were most marked in the 30 mcg/kg/d relaxin group, although similar but smaller trends were seen with 10 and 100 mcg/kg/d doses of relaxin. There were no concerning safety signals for relaxin in AHF patients identified in this study.

Various modifications and variations of the present disclosure will be apparent to those skilled in the art without departing from the scope and spirit of the disclosure. Although the disclosure has been described in connection with specific preferred embodiments, it should be understood that the claims should not be unduly limited to such specific embodiments. Indeed, various modifications of the described modes for carrying out the disclosure, which are understood by those skilled in the art are intended to be within the scope of the claims.

We claim:

1. A method of treating dyspnea associated with acute heart failure comprising administering a pharmaceutically active H2 relaxin to a hypertensive or normotensive human subject in an amount therapeutically effective in reducing the dyspnea, wherein the relaxin is administered at an infusion rate of about 15 ug/kg/d.

2. A method of treating dyspnea associated with acute heart failure comprising administering a pharmaceutically active H2 relaxin to a hypertensive or normotensive human subject in an amount therapeutically effective in reducing the dyspnea, wherein the subject does not have known significant liver disease.

3. A method of treating dyspnea associated with acute heart failure comprising administering a pharmaceutically active H2 relaxin to a hypertensive or normotensive human subject in an amount therapeutically effective in reducing the dyspnea, wherein the subject has an estimated glomerular filtration rate of 30-75 mL/min/1.73 m$^2$.

4. A method of treating dyspnea associated with acute heart failure comprising administering a pharmaceutically active H2 relaxin to a hypertensive or normotensive human subject in an amount therapeutically effective in reducing the dyspnea wherein the subject is over the age of 65.

5. A method of treating dyspnea associated with acute heart failure comprising administering a pharmaceutically active H2 relaxin to a hypertensive or normotensive human subject in an amount therapeutically effective in reducing the dyspnea, wherein the subject is diabetic.

6. A method of treating dyspnea associated with acute heart failure comprising administering a pharmaceutically active H2 relaxin to a hypertensive or normotensive human subject in an amount therapeutically effective in reducing the dyspnea, wherein the subject is obese.

7. A method of treating dyspnea associated with acute heart failure comprising administering a pharmaceutically active H2 relaxin to a hypertensive or normotensive human subject in an amount therapeutically effective in reducing the dyspnea, wherein an additional cardiovascular drug is administered to the subject.

8. The method of claim 7, wherein the additional cardiovascular drug is chosen from a nitrate, an aldosterone inhibitor, an inotrope, an angiotensin receptor blocker, an angiotensin converting enzyme inhibitor, a beta blocker, an HMG Co-A reductase inhibitor, a diuretic, an endothelin-1 blocker, a vasopressin receptor antagonist, a natriuretic peptide and a calcium channel blocker.

9. The method of claim 8, wherein the nitrate is chosen from nitroglycerin, isosorbate mononitrate, isosorbate dinitrate.

10. The method of claim 8, wherein the inotrope is digoxin or digitalis.

11. The method of claim 8, wherein the inotrope is chosen from dopamine, dobutamine, milrinone or a phosphodiesterase-III inhibitor.

12. A method of treating dyspnea associated with acute heart failure comprising administering a pharmaceutically active H2 relaxin to a hypertensive or normotensive human subject in an amount therapeutically effective in reducing the dyspnea, further comprising reducing the 30-day risk of death or rehospitalization compared to treatment of acute heart failure without relaxin.

13. The method of claim 12, wherein the 30-day risk of death or rehospitalization is reduced by at least about 50%.

14. The method of claim 12, wherein the rehospitalization is due to a cardiovascular cause.

15. The method of claim 14, wherein the cardiovascular cause is heart failure.

16. A method of treating dyspnea associated with acute heart failure comprising administering a pharmaceutically active H2 relaxin to a hypertensive or normotensive human subject in an amount therapeutically effective in reducing the dyspnea, further comprising reducing the 30-day, the 60-day or the 180 day worsening of heart failure.

* * * * *